US009969806B2

(12) United States Patent
Tanko et al.

(10) Patent No.: US 9,969,806 B2
(45) Date of Patent: May 15, 2018

(54) ADMINISTRATION OF BIMAGRUMAB FOR IMPROVING MUSCLE MASS AND FUNCTION AFTER HIP FRACTURE SURGERY

(71) Applicants: Laszlo Tanko, Riehen (CH); Dimitris Papanicolaou, Tenafly, NJ (US); Jörg Goldhahn, Walbach (CH)

(72) Inventors: Laszlo Tanko, Riehen (CH); Dimitris Papanicolaou, Tenafly, NJ (US); Jörg Goldhahn, Walbach (CH)

(73) Assignee: Novartis AG, Basel (CH)

( * ) Notice: Subject to any disclaimer, the term of this patent is extended or adjusted under 35 U.S.C. 154(b) by 0 days. days.

(21) Appl. No.: 15/304,010

(22) PCT Filed: Apr. 24, 2015

(86) PCT No.: PCT/IB2015/052990
§ 371 (c)(1),
(2) Date: Oct. 13, 2016

(87) PCT Pub. No.: WO2015/162590
PCT Pub. Date: Oct. 29, 2015

(65) Prior Publication Data
US 2017/0029513 A1 Feb. 2, 2017

Related U.S. Application Data

(60) Provisional application No. 61/983,565, filed on Apr. 24, 2014.

(51) Int. Cl.
*C07K 16/28* (2006.01)
*A61K 39/395* (2006.01)

(52) U.S. Cl.
CPC ...... *C07K 16/2863* (2013.01); *A61K 39/3955* (2013.01); *C07K 2317/21* (2013.01); *C07K 2317/55* (2013.01); *C07K 2317/565* (2013.01); *C07K 2317/76* (2013.01)

(58) Field of Classification Search
CPC ............ C07K 16/2863; C07K 2317/21; C07K 2317/55; C07K 2317/565; C07K 2317/76; A61K 39/3955
See application file for complete search history.

(56) References Cited

U.S. PATENT DOCUMENTS 7,807,159 B2 * 10/2010 Chin ...................... C07K 16/22
424/133.1

FOREIGN PATENT DOCUMENTS

| WO | WO2006/083182 A1 | 8/2006 |
| WO | WO2010/125003 A1 | 11/2010 |
| WO | WO2011/151432 A1 | 12/2011 |

OTHER PUBLICATIONS

Murphy KT, et al. American Journal of Physiology—Regulatory, Integrative and Comparative Physiology. Sep. 1, 2011. 301(3):R716-R726. Available online at—DOI: 10.1152/ajpregu.00121.2011.*
Lach-Trifilieff E, et al. Mol. Cell Biol. 34(4):606-618. Feb. 2014. Available online at—doi: 10.1128/MCB.01307-13.*
Siriett V, et al. Journal of Cellular Physiology. 209:866-873. 2006. Available online at—DOI: 10.1002/jcp.20778.*
Han HQ, et al. The International Journal of Biochemistry and Cell Biology. 45(10):2333-2347. Oct. 2013. Available online at—doi: 10.1016/j.biocel.2013.05.019.*
Estelle Lach-Trifilieff et al., "An Antibody Blocking Activin Type II Receptors Induces Strong Skeletal Muscle Hypertrophy and Protects from Atrophy", Molecular and Cellular Biology, American Society for Microbiology, Washington, vol. 34, No. 4, Feb. 1, 2014 (Feb. 1, 2014), pp. 606-618.
Fei Gao et al., Myostatin acts as an autocrine/paracrine negative regulator in myoblast differentiation from human induced pluripotent stem cells, Biochemical and Biophysical Research Communications, Jan. 4, 2013, pp. 309-314, vol. 431, Elsevier, Department of Immunology, Kyoto Prefectural University of Medicine, Kyoto, Japan Department of Cardiac Support, Kyoto Prefectural University of Medicine, Kyoto, Japan.
Benjamin T. Wall et al., Skeletal muscle atrophy during short-term disuse: Implications for age-related sarcopenia, Ageing Research Reviews, Aug. 12, 2013, pp. 898-906, vol. 12, Elsevier, Department of Human Movement Sciences, Nutrim School for Nutrition, Toxicology and Metabolism, Maastricht University Medical Centre, Maastricht, The Netherlands.
Stefano Ciciliot et al., Muscle type and fiber type specificity in muscle wasting, The International Journal of Biochemistry & Cell Biology, May 21, 2013, pp. 2191-2199, vol. 45, Elsevier, Venetian Institute of Molecular Medicine (VIMM), Padova, Italy, Department of Biomedical Sciences, University of Padova, Padova, Italy, Consiglio Nazionale delle Ricerche (CNR), Institute of Neuroscience, Padova, Italy.
RL Lalonde et al., Model-based Drug Development, Clinical Pharmacology & Therapeutics, May 23, 2007, pp. 21-32, vol. 82, No. 01, nature publishing group, Department of Clinical Pharmacology, Pfizer Global Research and Development, Groton, Ann Arbor, Sandwich, New York, La Jolla, Tokyo; 2Department of Statistics, Pfizer Global Research and Development, Groton, Ann Arbor, Sandwich, New York, La Jolla, Tokyo.
Leonard V. Sacks et al., Scientific and Regulatory Reasons for Delay and Denial of FDA Approval of Initial Applications for New Drugs, 2000-2012, JAMA, Jan. 2014, pp. 378-384, vol. 311, No. 4,American Medical Association,Office of Medical Policy, Center for Drug Evaluation and Research, US Food and Drug Administration, Silver Spring, Maryland.

*Primary Examiner* — Robert S Landsman
(74) *Attorney, Agent, or Firm* — Leslie Fischer

(57) ABSTRACT

The disclosure relates to uses and regimens for accelerating/improving physical recovery in a patient with disuse atrophy triggered by reduced mobility due to a hip fracture and consequent major surgery, which employ a therapeutically effective amount of a myostatin antagonist, e.g., a myostatin binding molecule, e.g., a myostatin antibody or an ActRII receptor binding molecule, an ActRII receptor antibody, such as the bimagrumab antibody.

11 Claims, 8 Drawing Sheets

(56) References Cited

OTHER PUBLICATIONS

John Carroll, Novartis' 'breakthrough' muscle drug bimagrumab flunks a late-stage trial, Fierce Biotech, Apr. 21, 2016, pp. 1-3, Fierce Pharma, Newton, MA.
Se-Jin Lee et al., Regulation of myostatin activity and muscle growth, PNAS, Jul. 31, 2001, pp. 9306-9311, vol. 98, No.16, Baltimore, MD.
Reardon et al., "Myostatin, insulin-like growth factor-1, and leukemia inhibitory factor mRNAs are upregulated in chronic human disuse muscle atrophy", Muscle Nerve, Jul. 1, 2001, vol. 24, No. 7, pp. 893-899.

* cited by examiner

SEQUENCE LISTING

```
<160> NUMBER OF SEQ ID NOS: 194

<210> SEQ ID NO 1
<211> LENGTH: 10
<212> TYPE: PRT
<213> ORGANISM: Artificial
<220> FEATURE:
```

<223> OTHER INFORMATION: CDR

<400> SEQUENCE: 1

Gly Tyr Thr Phe Thr Ser Ser Tyr Ile Asn
1               5                   10

<210> SEQ ID NO 2
<211> LENGTH: 10
<212> TYPE: PRT
<213> ORGANISM: Artificial
<220> FEATURE:
<223> OTHER INFORMATION: CDR

<400> SEQUENCE: 2

Gly Tyr Thr Phe Thr Ser Ser Tyr Ile Asn
1               5                   10

<210> SEQ ID NO 3
<211> LENGTH: 10
<212> TYPE: PRT
<213> ORGANISM: Artificial
<220> FEATURE:
<223> OTHER INFORMATION: CDR

<400> SEQUENCE: 3

Gly Tyr Thr Phe Thr Ser Ser Tyr Ile Asn
1               5                   10

<210> SEQ ID NO 4
<211> LENGTH: 10
<212> TYPE: PRT
<213> ORGANISM: Artificial
<220> FEATURE:
<223> OTHER INFORMATION: CDR

<400> SEQUENCE: 4

Gly Tyr Thr Phe Thr Ser Ser Tyr Ile Asn
1               5                   10

<210> SEQ ID NO 5
<211> LENGTH: 10
<212> TYPE: PRT
<213> ORGANISM: Artificial
<220> FEATURE:
<223> OTHER INFORMATION: CDR

<400> SEQUENCE: 5

Gly Tyr Thr Phe Thr Ser Ser Tyr Ile Asn
1               5                   10

<210> SEQ ID NO 6
<211> LENGTH: 10
<212> TYPE: PRT
<213> ORGANISM: Artificial
<220> FEATURE:
<223> OTHER INFORMATION: CDR

<400> SEQUENCE: 6

Gly Tyr Thr Phe Thr Ser Ser Tyr Ile Asn
1               5                   10

<210> SEQ ID NO 7
<211> LENGTH: 10
<212> TYPE: PRT
<213> ORGANISM: Artificial
<220> FEATURE:
<223> OTHER INFORMATION: CDR

<400> SEQUENCE: 7

Gly Tyr Thr Phe Thr Ser Ser Tyr Ile Asn
1               5                   10

<210> SEQ ID NO 8
<211> LENGTH: 10
<212> TYPE: PRT
<213> ORGANISM: Artificial
<220> FEATURE:
<223> OTHER INFORMATION: CDR

<400> SEQUENCE: 8

Gly Tyr Thr Phe Thr Ser Ser Tyr Ile Asn
1               5                   10

<210> SEQ ID NO 9
<211> LENGTH: 10
<212> TYPE: PRT
<213> ORGANISM: Artificial
<220> FEATURE:
<223> OTHER INFORMATION: CDR

<400> SEQUENCE: 9

Gly Tyr Thr Phe Thr Ser Ser Tyr Ile Asn
1               5                   10

<210> SEQ ID NO 10
<211> LENGTH: 10
<212> TYPE: PRT
<213> ORGANISM: Artificial
<220> FEATURE:
<223> OTHER INFORMATION: CDR

<400> SEQUENCE: 10

Gly Tyr Thr Phe Thr Ser Ser Tyr Ile Asn
1               5                   10

<210> SEQ ID NO 11
<211> LENGTH: 10
<212> TYPE: PRT
<213> ORGANISM: Artificial
<220> FEATURE:
<223> OTHER INFORMATION: CDR

<400> SEQUENCE: 11

Gly Tyr Thr Phe Thr Ser Ser Tyr Ile Asn
1               5                   10

<210> SEQ ID NO 12
<211> LENGTH: 10
<212> TYPE: PRT
<213> ORGANISM: Artificial
<220> FEATURE:
<223> OTHER INFORMATION: CDR

<400> SEQUENCE: 12

Gly Tyr Thr Phe Thr Ser Ser Tyr Ile Asn
1               5                   10

<210> SEQ ID NO 13
<211> LENGTH: 10
<212> TYPE: PRT
<213> ORGANISM: Artificial
<220> FEATURE:
<223> OTHER INFORMATION: CDR

```
<400> SEQUENCE: 13

Gly Tyr Thr Phe Thr Ser Ser Tyr Ile Asn
1               5                   10

<210> SEQ ID NO 14
<211> LENGTH: 10
<212> TYPE: PRT
<213> ORGANISM: Artificial
<220> FEATURE:
<223> OTHER INFORMATION: CDR

<400> SEQUENCE: 14

Gly Tyr Thr Phe Thr Ser Ser Tyr Ile Asn
1               5                   10

<210> SEQ ID NO 15
<211> LENGTH: 17
<212> TYPE: PRT
<213> ORGANISM: Artificial
<220> FEATURE:
<223> OTHER INFORMATION: CDR

<400> SEQUENCE: 15

Thr Ile Asn Pro Val Ser Gly Asn Thr Ser Tyr Ala Gln Lys Phe Gln
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: CDR

<400> SEQUENCE: 16

Thr Ile Asn Pro Val Ser Gly Asn Thr Ser Tyr Ala Gln Lys Phe Gln
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: CDR

<400> SEQUENCE: 17

Thr Ile Asn Pro Val Ser Gly Asn Thr Ser Tyr Ala Gln Lys Phe Gln
1               5                   10                  15

Gly

<210> SEQ ID NO 18
<211> LENGTH: 17
<212> TYPE: PRT
<213> ORGANISM: Artificial
<220> FEATURE:
<223> OTHER INFORMATION: CDR

<400> SEQUENCE: 18

Thr Ile Asn Pro Val Ser Gly Asn Thr Ser Tyr Ala Gln Lys Phe Gln
1               5                   10                  15

Gly
```

```
<210> SEQ ID NO 19
<211> LENGTH: 17
<212> TYPE: PRT
<213> ORGANISM: Artificial
<220> FEATURE:
<223> OTHER INFORMATION: CDR

<400> SEQUENCE: 19

Met Ile Asn Ala Pro Ile Gly Thr Thr Arg Tyr Ala Gln Lys Phe Gln
1               5                   10                  15

Gly

<210> SEQ ID NO 20
<211> LENGTH: 17
<212> TYPE: PRT
<213> ORGANISM: Artificial
<220> FEATURE:
<223> OTHER INFORMATION: CDR

<400> SEQUENCE: 20

Gln Ile Asn Ala Ala Ser Gly Met Thr Arg Tyr Ala Gln Lys Phe Gln
1               5                   10                  15

Gly

<210> SEQ ID NO 21
<211> LENGTH: 17
<212> TYPE: PRT
<213> ORGANISM: Artificial
<220> FEATURE:
<223> OTHER INFORMATION: CDR

<400> SEQUENCE: 21

Met Ile Asn Ala Pro Ile Gly Thr Thr Arg Tyr Ala Gln Lys Phe Gln
1               5                   10                  15

Gly

<210> SEQ ID NO 22
<211> LENGTH: 17
<212> TYPE: PRT
<213> ORGANISM: Artificial
<220> FEATURE:
<223> OTHER INFORMATION: CDR

<400> SEQUENCE: 22

Thr Ile Asn Pro Val Ser Gly Asn Thr Arg Tyr Ala Gln Lys Phe Gln
1               5                   10                  15

Gly

<210> SEQ ID NO 23
<211> LENGTH: 17
<212> TYPE: PRT
<213> ORGANISM: Artificial
<220> FEATURE:
<223> OTHER INFORMATION: CDR

<400> SEQUENCE: 23

Thr Ile Asn Pro Val Ser Gly Ser Thr Ser Tyr Ala Gln Lys Phe Gln
1               5                   10                  15

Gly

<210> SEQ ID NO 24
<211> LENGTH: 17
<212> TYPE: PRT
<213> ORGANISM: Artificial
```

```
<220> FEATURE:
<223> OTHER INFORMATION: CDR

<400> SEQUENCE: 24

Gln Ile Asn Ala Ala Ser Gly Met Thr Arg Tyr Ala Gln Lys Phe Gln
1               5                   10                  15
Gly

<210> SEQ ID NO 25
<211> LENGTH: 17
<212> TYPE: PRT
<213> ORGANISM: Artificial
<220> FEATURE:
<223> OTHER INFORMATION: CDR

<400> SEQUENCE: 25

Asn Ile Asn Ala Ala Ala Gly Ile Thr Leu Tyr Ala Gln Lys Phe Gln
1               5                   10                  15
Gly

<210> SEQ ID NO 26
<211> LENGTH: 17
<212> TYPE: PRT
<213> ORGANISM: Artificial
<220> FEATURE:
<223> OTHER INFORMATION: CDR

<400> SEQUENCE: 26

Thr Ile Asn Pro Pro Thr Gly Gly Thr Tyr Tyr Ala Gln Lys Phe Gln
1               5                   10                  15
Gly

<210> SEQ ID NO 27
<211> LENGTH: 17
<212> TYPE: PRT
<213> ORGANISM: Artificial
<220> FEATURE:
<223> OTHER INFORMATION: CDR

<400> SEQUENCE: 27

Gly Ile Asn Pro Pro Ala Gly Thr Thr Ser Tyr Ala Gln Lys Phe Gln
1               5                   10                  15
Gly

<210> SEQ ID NO 28
<211> LENGTH: 17
<212> TYPE: PRT
<213> ORGANISM: Artificial
<220> FEATURE:
<223> OTHER INFORMATION: CDR

<400> SEQUENCE: 28

Asn Ile Asn Pro Ala Thr Gly His Ala Asp Tyr Ala Gln Lys Phe Gln
1               5                   10                  15
Gly

<210> SEQ ID NO 29
<211> LENGTH: 6
<212> TYPE: PRT
<213> ORGANISM: Artificial
<220> FEATURE:
<223> OTHER INFORMATION: CDR

<400> SEQUENCE: 29
```

Gly Gly Trp Phe Asp Tyr
1               5

<210> SEQ ID NO 30
<211> LENGTH: 6
<212> TYPE: PRT
<213> ORGANISM: Artificial
<220> FEATURE:
<223> OTHER INFORMATION: CDR

<400> SEQUENCE: 30

Gly Gly Trp Phe Asp Tyr
1               5

<210> SEQ ID NO 31
<211> LENGTH: 6
<212> TYPE: PRT
<213> ORGANISM: Artificial
<220> FEATURE:
<223> OTHER INFORMATION: CDR

<400> SEQUENCE: 31

Gly Gly Trp Phe Asp Tyr
1               5

<210> SEQ ID NO 32
<211> LENGTH: 6
<212> TYPE: PRT
<213> ORGANISM: Artificial
<220> FEATURE:
<223> OTHER INFORMATION: CDR

<400> SEQUENCE: 32

Gly Gly Trp Phe Asp Tyr
1               5

<210> SEQ ID NO 33
<211> LENGTH: 6
<212> TYPE: PRT
<213> ORGANISM: Artificial
<220> FEATURE:
<223> OTHER INFORMATION: CDR

<400> SEQUENCE: 33

Gly Gly Trp Phe Asp Tyr
1               5

<210> SEQ ID NO 34
<211> LENGTH: 6
<212> TYPE: PRT
<213> ORGANISM: Artificial
<220> FEATURE:
<223> OTHER INFORMATION: CDR

<400> SEQUENCE: 34

Gly Gly Trp Phe Asp Tyr
1               5

<210> SEQ ID NO 35
<211> LENGTH: 6
<212> TYPE: PRT
<213> ORGANISM: Artificial
<220> FEATURE:
<223> OTHER INFORMATION: CDR

<400> SEQUENCE: 35

```
Gly Gly Trp Phe Asp Tyr
1               5

<210> SEQ ID NO 36
<211> LENGTH: 6
<212> TYPE: PRT
<213> ORGANISM: Artificial
<220> FEATURE:
<223> OTHER INFORMATION: CDR

<400> SEQUENCE: 36

Gly Gly Trp Phe Asp Tyr
1               5

<210> SEQ ID NO 37
<211> LENGTH: 6
<212> TYPE: PRT
<213> ORGANISM: Artificial
<220> FEATURE:
<223> OTHER INFORMATION: CDR

<400> SEQUENCE: 37

Gly Gly Trp Phe Asp Tyr
1               5

<210> SEQ ID NO 38
<211> LENGTH: 6
<212> TYPE: PRT
<213> ORGANISM: Artificial
<220> FEATURE:
<223> OTHER INFORMATION: CDR

<400> SEQUENCE: 38

Gly Gly Trp Phe Asp Tyr
1               5

<210> SEQ ID NO 39
<211> LENGTH: 6
<212> TYPE: PRT
<213> ORGANISM: Artificial
<220> FEATURE:
<223> OTHER INFORMATION: CDR

<400> SEQUENCE: 39

Gly Gly Trp Phe Asp Tyr
1               5

<210> SEQ ID NO 40
<211> LENGTH: 6
<212> TYPE: PRT
<213> ORGANISM: Artificial
<220> FEATURE:
<223> OTHER INFORMATION: CDR

<400> SEQUENCE: 40

Gly Gly Trp Phe Asp Tyr
1               5

<210> SEQ ID NO 41
<211> LENGTH: 6
<212> TYPE: PRT
<213> ORGANISM: Artificial
<220> FEATURE:
<223> OTHER INFORMATION: CDR

<400> SEQUENCE: 41

Gly Gly Trp Phe Asp Tyr
```

```
1               5

<210> SEQ ID NO 42
<211> LENGTH: 6
<212> TYPE: PRT
<213> ORGANISM: Artificial
<220> FEATURE:
<223> OTHER INFORMATION: CDR

<400> SEQUENCE: 42

Gly Gly Trp Phe Asp Tyr
1               5

<210> SEQ ID NO 43
<211> LENGTH: 14
<212> TYPE: PRT
<213> ORGANISM: Artificial
<220> FEATURE:
<223> OTHER INFORMATION: CDR

<400> SEQUENCE: 43

Thr Gly Thr Ser Ser Asp Val Gly Ser Tyr Asn Tyr Val Asn
1               5                   10

<210> SEQ ID NO 44
<211> LENGTH: 14
<212> TYPE: PRT
<213> ORGANISM: Artificial
<220> FEATURE:
<223> OTHER INFORMATION: CDR

<400> SEQUENCE: 44

Thr Gly Thr Ser Ser Asp Val Gly Ser Tyr Asn Tyr Val Asn
1               5                   10

<210> SEQ ID NO 45
<211> LENGTH: 14
<212> TYPE: PRT
<213> ORGANISM: Artificial
<220> FEATURE:
<223> OTHER INFORMATION: CDR

<400> SEQUENCE: 45

Thr Gly Thr Ser Ser Asp Val Gly Ser Tyr Asn Tyr Val Asn
1               5                   10

<210> SEQ ID NO 46
<211> LENGTH: 14
<212> TYPE: PRT
<213> ORGANISM: Artificial
<220> FEATURE:
<223> OTHER INFORMATION: CDR

<400> SEQUENCE: 46

Thr Gly Thr Ser Ser Asp Val Gly Ser Tyr Asn Tyr Val Asn
1               5                   10

<210> SEQ ID NO 47
<211> LENGTH: 14
<212> TYPE: PRT
<213> ORGANISM: Artificial
<220> FEATURE:
<223> OTHER INFORMATION: CDR

<400> SEQUENCE: 47

Thr Gly Thr Ser Ser Asp Val Gly Ser Tyr Asn Tyr Val Asn
1               5                   10
```

```
<210> SEQ ID NO 48
<211> LENGTH: 14
<212> TYPE: PRT
<213> ORGANISM: Artificial
<220> FEATURE:
<223> OTHER INFORMATION: CDR

<400> SEQUENCE: 48

Thr Gly Thr Ser Ser Asp Val Gly Ser Tyr Asn Tyr Val Asn
1               5                   10

<210> SEQ ID NO 49
<211> LENGTH: 14
<212> TYPE: PRT
<213> ORGANISM: Artificial
<220> FEATURE:
<223> OTHER INFORMATION: CDR

<400> SEQUENCE: 49

Thr Gly Thr Ser Ser Asp Val Gly Ser Tyr Asn Tyr Val Asn
1               5                   10

<210> SEQ ID NO 50
<211> LENGTH: 14
<212> TYPE: PRT
<213> ORGANISM: Artificial
<220> FEATURE:
<223> OTHER INFORMATION: CDR

<400> SEQUENCE: 50

Thr Gly Thr Ser Ser Asp Val Gly Ser Tyr Asn Tyr Val Asn
1               5                   10

<210> SEQ ID NO 51
<211> LENGTH: 14
<212> TYPE: PRT
<213> ORGANISM: Artificial
<220> FEATURE:
<223> OTHER INFORMATION: CDR

<400> SEQUENCE: 51

Thr Gly Thr Ser Ser Asp Val Gly Ser Tyr Asn Tyr Val Asn
1               5                   10

<210> SEQ ID NO 52
<211> LENGTH: 14
<212> TYPE: PRT
<213> ORGANISM: Artificial
<220> FEATURE:
<223> OTHER INFORMATION: CDR

<400> SEQUENCE: 52

Thr Gly Thr Ser Ser Asp Val Gly Ser Tyr Asn Tyr Val Asn
1               5                   10

<210> SEQ ID NO 53
<211> LENGTH: 14
<212> TYPE: PRT
<213> ORGANISM: Artificial
<220> FEATURE:
<223> OTHER INFORMATION: CDR

<400> SEQUENCE: 53

Thr Gly Thr Ser Ser Asp Val Gly Ser Tyr Asn Tyr Val Asn
1               5                   10
```

```
<210> SEQ ID NO 54
<211> LENGTH: 14
<212> TYPE: PRT
<213> ORGANISM: Artificial
<220> FEATURE:
<223> OTHER INFORMATION: CDR

<400> SEQUENCE: 54

Thr Gly Thr Ser Ser Asp Val Gly Ser Tyr Asn Tyr Val Asn
1               5                   10

<210> SEQ ID NO 55
<211> LENGTH: 14
<212> TYPE: PRT
<213> ORGANISM: Artificial
<220> FEATURE:
<223> OTHER INFORMATION: CDR

<400> SEQUENCE: 55

Thr Gly Thr Ser Ser Asp Val Gly Ser Tyr Asn Tyr Val Asn
1               5                   10

<210> SEQ ID NO 56
<211> LENGTH: 14
<212> TYPE: PRT
<213> ORGANISM: Artificial
<220> FEATURE:
<223> OTHER INFORMATION: CDR

<400> SEQUENCE: 56

Thr Gly Thr Ser Ser Asp Val Gly Ser Tyr Asn Tyr Val Asn
1               5                   10

<210> SEQ ID NO 57
<211> LENGTH: 11
<212> TYPE: PRT
<213> ORGANISM: Artificial
<220> FEATURE:
<223> OTHER INFORMATION: CDR

<400> SEQUENCE: 57

Leu Met Ile Tyr Gly Val Ser Lys Arg Pro Ser
1               5                   10

<210> SEQ ID NO 58
<211> LENGTH: 11
<212> TYPE: PRT
<213> ORGANISM: Artificial
<220> FEATURE:
<223> OTHER INFORMATION: CDR

<400> SEQUENCE: 58

Leu Met Ile Tyr Gly Val Ser Lys Arg Pro Ser
1               5                   10

<210> SEQ ID NO 59
<211> LENGTH: 11
<212> TYPE: PRT
<213> ORGANISM: Artificial
<220> FEATURE:
<223> OTHER INFORMATION: CDR

<400> SEQUENCE: 59

Leu Met Ile Tyr Gly Val Ser Lys Arg Pro Ser
1               5                   10
```

```
<210> SEQ ID NO 60
<211> LENGTH: 11
<212> TYPE: PRT
<213> ORGANISM: Artificial
<220> FEATURE:
<223> OTHER INFORMATION: CDR

<400> SEQUENCE: 60

Leu Met Ile Tyr Gly Val Ser Lys Arg Pro Ser
1               5                   10

<210> SEQ ID NO 61
<211> LENGTH: 11
<212> TYPE: PRT
<213> ORGANISM: Artificial
<220> FEATURE:
<223> OTHER INFORMATION: CDR

<400> SEQUENCE: 61

Leu Met Ile Tyr Gly Val Ser Lys Arg Pro Ser
1               5                   10

<210> SEQ ID NO 62
<211> LENGTH: 11
<212> TYPE: PRT
<213> ORGANISM: Artificial
<220> FEATURE:
<223> OTHER INFORMATION: CDR

<400> SEQUENCE: 62

Leu Met Ile Tyr Gly Val Ser Lys Arg Pro Ser
1               5                   10

<210> SEQ ID NO 63
<211> LENGTH: 11
<212> TYPE: PRT
<213> ORGANISM: Artificial
<220> FEATURE:
<223> OTHER INFORMATION: CDR

<400> SEQUENCE: 63

Leu Met Ile Tyr Gly Val Ser Lys Arg Pro Ser
1               5                   10

<210> SEQ ID NO 64
<211> LENGTH: 11
<212> TYPE: PRT
<213> ORGANISM: Artificial
<220> FEATURE:
<223> OTHER INFORMATION: CDR

<400> SEQUENCE: 64

Leu Met Ile Tyr Gly Val Ser Lys Arg Pro Ser
1               5                   10

<210> SEQ ID NO 65
<211> LENGTH: 11
<212> TYPE: PRT
<213> ORGANISM: Artificial
<220> FEATURE:
<223> OTHER INFORMATION: CDR

<400> SEQUENCE: 65

Leu Met Ile Tyr Gly Val Ser Lys Arg Pro Ser
1               5                   10

<210> SEQ ID NO 66
```

```
<211> LENGTH: 11
<212> TYPE: PRT
<213> ORGANISM: Artificial
<220> FEATURE:
<223> OTHER INFORMATION: CDR

<400> SEQUENCE: 66

Leu Met Ile Tyr Gly Val Ser Lys Arg Pro Ser
1               5                   10

<210> SEQ ID NO 67
<211> LENGTH: 11
<212> TYPE: PRT
<213> ORGANISM: Artificial
<220> FEATURE:
<223> OTHER INFORMATION: CDR

<400> SEQUENCE: 67

Leu Met Ile Tyr Gly Val Ser Lys Arg Pro Ser
1               5                   10

<210> SEQ ID NO 68
<211> LENGTH: 11
<212> TYPE: PRT
<213> ORGANISM: Artificial
<220> FEATURE:
<223> OTHER INFORMATION: CDR

<400> SEQUENCE: 68

Leu Met Ile Tyr Gly Val Ser Lys Arg Pro Ser
1               5                   10

<210> SEQ ID NO 69
<211> LENGTH: 11
<212> TYPE: PRT
<213> ORGANISM: Artificial
<220> FEATURE:
<223> OTHER INFORMATION: CDR

<400> SEQUENCE: 69

Leu Met Ile Tyr Gly Val Ser Lys Arg Pro Ser
1               5                   10

<210> SEQ ID NO 70
<211> LENGTH: 11
<212> TYPE: PRT
<213> ORGANISM: Artificial
<220> FEATURE:
<223> OTHER INFORMATION: CDR

<400> SEQUENCE: 70

Leu Met Ile Tyr Gly Val Ser Lys Arg Pro Ser
1               5                   10

<210> SEQ ID NO 71
<211> LENGTH: 9
<212> TYPE: PRT
<213> ORGANISM: Artificial
<220> FEATURE:
<223> OTHER INFORMATION: CDR

<400> SEQUENCE: 71

Gln Ala Trp Thr Ser Lys Met Ala Gly
1               5

<210> SEQ ID NO 72
<211> LENGTH: 9
```

```
<212> TYPE: PRT
<213> ORGANISM: Artificial
<220> FEATURE:
<223> OTHER INFORMATION: CDR

<400> SEQUENCE: 72

Ser Ser Tyr Thr Arg Met Gly His Pro
1               5

<210> SEQ ID NO 73
<211> LENGTH: 10
<212> TYPE: PRT
<213> ORGANISM: Artificial
<220> FEATURE:
<223> OTHER INFORMATION: CDR

<400> SEQUENCE: 73

Ala Thr Tyr Gly Lys Gly Val Thr Pro Pro
1               5                   10

<210> SEQ ID NO 74
<211> LENGTH: 10
<212> TYPE: PRT
<213> ORGANISM: Artificial
<220> FEATURE:
<223> OTHER INFORMATION: CDR

<400> SEQUENCE: 74

Gly Thr Phe Ala Gly Gly Ser Tyr Tyr Gly
1               5                   10

<210> SEQ ID NO 75
<211> LENGTH: 9
<212> TYPE: PRT
<213> ORGANISM: Artificial
<220> FEATURE:
<223> OTHER INFORMATION: CDR

<400> SEQUENCE: 75

Gln Ala Trp Thr Ser Lys Met Ala Gly
1               5

<210> SEQ ID NO 76
<211> LENGTH: 9
<212> TYPE: PRT
<213> ORGANISM: Artificial
<220> FEATURE:
<223> OTHER INFORMATION: CDR

<400> SEQUENCE: 76

Gln Ala Trp Thr Ser Lys Met Ala Gly
1               5

<210> SEQ ID NO 77
<211> LENGTH: 10
<212> TYPE: PRT
<213> ORGANISM: Artificial
<220> FEATURE:
<223> OTHER INFORMATION: CDR

<400> SEQUENCE: 77

Gly Thr Phe Ala Gly Gly Ser Tyr Tyr Gly
1               5                   10

<210> SEQ ID NO 78
<211> LENGTH: 10
<212> TYPE: PRT
```

<213> ORGANISM: Artificial
<220> FEATURE:
<223> OTHER INFORMATION: CDR

<400> SEQUENCE: 78

Gly Thr Phe Ala Gly Gly Ser Tyr Tyr Gly
1               5                   10

<210> SEQ ID NO 79
<211> LENGTH: 10
<212> TYPE: PRT
<213> ORGANISM: Artificial
<220> FEATURE:
<223> OTHER INFORMATION: CDR

<400> SEQUENCE: 79

Gly Thr Phe Ala Gly Gly Ser Tyr Tyr Gly
1               5                   10

<210> SEQ ID NO 80
<211> LENGTH: 10
<212> TYPE: PRT
<213> ORGANISM: Artificial
<220> FEATURE:
<223> OTHER INFORMATION: CDR

<400> SEQUENCE: 80

Gly Thr Phe Ala Gly Gly Ser Tyr Tyr Gly
1               5                   10

<210> SEQ ID NO 81
<211> LENGTH: 10
<212> TYPE: PRT
<213> ORGANISM: Artificial
<220> FEATURE:
<223> OTHER INFORMATION: CDR

<400> SEQUENCE: 81

Gly Thr Phe Ala Gly Gly Ser Tyr Tyr Gly
1               5                   10

<210> SEQ ID NO 82
<211> LENGTH: 10
<212> TYPE: PRT
<213> ORGANISM: Artificial
<220> FEATURE:
<223> OTHER INFORMATION: CDR

<400> SEQUENCE: 82

Gly Thr Phe Ala Gly Gly Ser Tyr Tyr Gly
1               5                   10

<210> SEQ ID NO 83
<211> LENGTH: 10
<212> TYPE: PRT
<213> ORGANISM: Artificial
<220> FEATURE:
<223> OTHER INFORMATION: CDR

<400> SEQUENCE: 83

Gly Thr Phe Ala Gly Gly Ser Tyr Tyr Gly
1               5                   10

<210> SEQ ID NO 84
<211> LENGTH: 10
<212> TYPE: PRT
<213> ORGANISM: Artificial

<220> FEATURE:
<223> OTHER INFORMATION: CDR

<400> SEQUENCE: 84

Gly Thr Phe Ala Gly Gly Ser Tyr Tyr Gly
1               5                   10

<210> SEQ ID NO 85
<211> LENGTH: 112
<212> TYPE: PRT
<213> ORGANISM: Artificial
<220> FEATURE:
<223> OTHER INFORMATION: VL

<400> SEQUENCE: 85

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ala Trp Thr Ser Lys
                85                  90                  95

Met Ala Gly Val Phe Gly Gly Thr Lys Leu Thr Val Leu Gly Gln
            100                 105                 110

<210> SEQ ID NO 86
<211> LENGTH: 112
<212> TYPE: PRT
<213> ORGANISM: Artificial
<220> FEATURE:
<223> OTHER INFORMATION: VL

<400> SEQUENCE: 86

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Met
                85                  90                  95

Gly His Pro Val Phe Gly Gly Thr Lys Leu Thr Val Leu Gly Gln
            100                 105                 110

<210> SEQ ID NO 87
<211> LENGTH: 113
<212> TYPE: PRT
<213> ORGANISM: Artificial
<220> FEATURE:
<223> OTHER INFORMATION: VL

<400> SEQUENCE: 87

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Ala Thr Tyr Gly Lys Gly
                85                  90                  95

Val Thr Pro Pro Val Phe Gly Gly Gly Thr Lys Leu Thr Val Leu Gly
            100                 105                 110

Gln

<210> SEQ ID NO 88
<211> LENGTH: 113
<212> TYPE: PRT
<213> ORGANISM: Artificial
<220> FEATURE:
<223> OTHER INFORMATION: VL

<400> SEQUENCE: 88

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
        50                  55                  60

Ser Gly Ser Lys Ser Gly Asn Thr Ala Ser Leu Thr Ile Ser Gly Leu
65              70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 89
<211> LENGTH: 112
<212> TYPE: PRT
<213> ORGANISM: Artificial
<220> FEATURE:
<223> OTHER INFORMATION: VL

<400> SEQUENCE: 89

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
        50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ala Trp Thr Ser Lys
                 85                  90                  95

Met Ala Gly Val Phe Gly Gly Gly Thr Lys Leu Thr Val Leu Gly Gln
            100                 105                 110

<210> SEQ ID NO 90
<211> LENGTH: 112
<212> TYPE: PRT
<213> ORGANISM: Artificial
<220> FEATURE:
<223> OTHER INFORMATION: VL

<400> SEQUENCE: 90

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
             35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ala Trp Thr Ser Lys
                 85                  90                  95

Met Ala Gly Val Phe Gly Gly Gly Thr Lys Leu Thr Val Leu Gly Gln
            100                 105                 110

<210> SEQ ID NO 91
<211> LENGTH: 113
<212> TYPE: PRT
<213> ORGANISM: Artificial
<220> FEATURE:
<223> OTHER INFORMATION: VL

<400> SEQUENCE: 91

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
             35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
            100                 105                 110

Gln

<210> SEQ ID NO 92
<211> LENGTH: 113
<212> TYPE: PRT
<213> ORGANISM: Artificial
<220> FEATURE:
```

<223> OTHER INFORMATION: VL

<400> SEQUENCE: 92

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 93
<211> LENGTH: 113
<212> TYPE: PRT
<213> ORGANISM: Artificial
<220> FEATURE:
<223> OTHER INFORMATION: VL

<400> SEQUENCE: 93

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 94
<211> LENGTH: 113
<212> TYPE: PRT
<213> ORGANISM: Artificial
<220> FEATURE:
<223> OTHER INFORMATION: VL

<400> SEQUENCE: 94

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

```
Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln

<210> SEQ ID NO 95
<211> LENGTH: 113
<212> TYPE: PRT
<213> ORGANISM: Artificial
<220> FEATURE:
<223> OTHER INFORMATION: VL

<400> SEQUENCE: 95

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln

<210> SEQ ID NO 96
<211> LENGTH: 113
<212> TYPE: PRT
<213> ORGANISM: Artificial
<220> FEATURE:
<223> OTHER INFORMATION: VL

<400> SEQUENCE: 96

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln
```

<210> SEQ ID NO 97
<211> LENGTH: 113
<212> TYPE: PRT
<213> ORGANISM: Artificial
<220> FEATURE:
<223> OTHER INFORMATION: VL

<400> SEQUENCE: 97

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 98
<211> LENGTH: 113
<212> TYPE: PRT
<213> ORGANISM: Artificial
<220> FEATURE:
<223> OTHER INFORMATION: VL

<400> SEQUENCE: 98

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 99
<211> LENGTH: 115
<212> TYPE: PRT
<213> ORGANISM: Artificial
<220> FEATURE:
<223> OTHER INFORMATION: VH

<400> SEQUENCE: 99

Gln Val Gln Leu Val Gln Ser Gly Ala Glu Val Lys Lys Pro Gly Ala
1               5                   10                  15

```
Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
            35                  40                  45

Gly Thr Ile Asn Pro Val Ser Gly Asn Thr Ser Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 100
<211> LENGTH: 115
<212> TYPE: PRT
<213> ORGANISM: Artificial
<220> FEATURE:
<223> OTHER INFORMATION: VH

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
            35                  40                  45

Gly Thr Ile Asn Pro Val Ser Gly Asn Thr Ser Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 101
<211> LENGTH: 115
<212> TYPE: PRT
<213> ORGANISM: Artificial
<220> FEATURE:
<223> OTHER INFORMATION: VH

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
            35                  40                  45

Gly Thr Ile Asn Pro Val Ser Gly Asn Thr Ser Tyr Ala Gln Lys Phe
 50                  55                  60

Gln Gly Arg Val Thr Met Thr Arg Asp Thr Ser Ile Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Arg Gly Gly Trp Phe Asp Tyr Trp Gly Gln Gly Thr Leu Val Thr
                100                 105                 110

Val Ser Ser
        115

<210> SEQ ID NO 102
<211> LENGTH: 115
<212> TYPE: PRT
<213> ORGANISM: Artificial
<220> FEATURE:
<223> OTHER INFORMATION: VH

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Thr Ile Asn Pro Val Ser Gly Asn Thr Ser Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Gly Trp Phe Asp Tyr Trp Gly Gln Gly Thr Leu Val Thr
                100                 105                 110

Val Ser Ser
        115

<210> SEQ ID NO 103
<211> LENGTH: 115
<212> TYPE: PRT
<213> ORGANISM: Artificial
<220> FEATURE:
<223> OTHER INFORMATION: VH

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Met Ile Asn Ala Pro Ile Gly Thr Thr Arg Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Gly Gly Trp Phe Asp Tyr Trp Gly Gln Gly Thr Leu Val Thr
                100                 105                 110

Val Ser Ser
        115
```

<210> SEQ ID NO 104
<211> LENGTH: 115
<212> TYPE: PRT
<213> ORGANISM: Artificial
<220> FEATURE:
<223> OTHER INFORMATION: VH

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Gln Ile Asn Ala Ala Ser Gly Met Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 105
<211> LENGTH: 115
<212> TYPE: PRT
<213> ORGANISM: Artificial
<220> FEATURE:
<223> OTHER INFORMATION: VH

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Met Ile Asn Ala Pro Ile Gly Thr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 106
<211> LENGTH: 115
<212> TYPE: PRT
<213> ORGANISM: Artificial
<220> FEATURE:
<223> OTHER INFORMATION: VH

<400> SEQUENCE: 106

Gln Val Gln Leu Val Gln Ser Gly Ala Glu Val Lys Lys Pro Gly Ala

```
                1               5                   10                  15
            Ser Val Lys Val Ser Cys Lys Ala Ser Gly Tyr Thr Phe Thr Ser Ser
                            20                  25                  30

Tyr Ile Asn Trp Val Arg Gln Ala Pro Gly Gln Gly Leu Glu Trp Met
                        35                  40                  45

Gly Thr Ile Asn Pro Val Ser Gly Asn Thr Arg Tyr Ala Gln Lys Phe
                    50                  55                  60

Gln Gly Arg Val Thr Met Thr Arg Asp Thr Ser Ile Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Gly Gly Trp Phe Asp Tyr Trp Gly Gln Gly Thr Leu Val Thr
                        100                 105                 110

Val Ser Ser
                    115

<210> SEQ ID NO 107
<211> LENGTH: 115
<212> TYPE: PRT
<213> ORGANISM: Artificial
<220> FEATURE:
<223> OTHER INFORMATION: VH

<400> SEQUENCE: 107

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Ser Ser
                            20                  25                  30

Tyr Ile Asn Trp Val Arg Gln Ala Pro Gly Gln Gly Leu Glu Trp Met
                        35                  40                  45

Gly Thr Ile Asn Pro Val Ser Gly Ser Thr Ser Tyr Ala Gln Lys Phe
                    50                  55                  60

Gln Gly Arg Val Thr Met Thr Arg Asp Thr Ser Ile Ser Thr Ala Tyr
            65                  70                  75                  80

Met Glu Leu Ser Ser Leu Arg Ser Glu Asp Thr Ala Val Tyr Tyr Cys
                            85                  90                  95

Ala Arg Gly Gly Trp Phe Asp Tyr Trp Gly Gln Gly Thr Leu Val Thr
                        100                 105                 110

Val Ser Ser
                    115

<210> SEQ ID NO 108
<211> LENGTH: 115
<212> TYPE: PRT
<213> ORGANISM: Artificial
<220> FEATURE:
<223> OTHER INFORMATION: VH

<400> SEQUENCE: 108

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Ser Ser
                            20                  25                  30

Tyr Ile Asn Trp Val Arg Gln Ala Pro Gly Gln Gly Leu Glu Trp Met
                        35                  40                  45

Gly Gln Ile Asn Ala Ala Ser Gly Met Thr Arg Tyr Ala Gln Lys Phe
                    50                  55                  60
```

-continued

```
Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 109
<211> LENGTH: 115
<212> TYPE: PRT
<213> ORGANISM: Artificial
<220> FEATURE:
<223> OTHER INFORMATION: VH

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
             35                  40                  45

Gly Asn Ile Asn Ala Ala Gly Ile Thr Leu Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 110
<211> LENGTH: 115
<212> TYPE: PRT
<213> ORGANISM: Artificial
<220> FEATURE:
<223> OTHER INFORMATION: VH

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
             35                  40                  45

Gly Thr Ile Asn Pro Pro Thr Gly Gly Thr Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Trp Phe Asp Tyr Trp Gly Gln Gly Thr Leu Val Thr
            100                 105                 110

Val Ser Ser
        115
```

<210> SEQ ID NO 111
<211> LENGTH: 115
<212> TYPE: PRT
<213> ORGANISM: Artificial
<220> FEATURE:
<223> OTHER INFORMATION: VH

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gly Ile Asn Pro Ala Gly Thr Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 112
<211> LENGTH: 115
<212> TYPE: PRT
<213> ORGANISM: Artificial
<220> FEATURE:
<223> OTHER INFORMATION: VH

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Asn Ile Asn Pro Ala Thr Gly His Ala Asp Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 113
<211> LENGTH: 336
<212> TYPE: DNA
<213> ORGANISM: Artificial
<220> FEATURE:
<223> OTHER INFORMATION: VL

<400> SEQUENCE: 113

```
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc caggcttgga cttctaagat ggctggtgtg   300
tttggcggcg gcacgaagtt aaccgttctt ggccag                             336
```

<210> SEQ ID NO 114
<211> LENGTH: 336
<212> TYPE: DNA
<213> ORGANISM: Artificial
<220> FEATURE:
<223> OTHER INFORMATION: VL

<400> SEQUENCE: 114

```
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc tcttcttata ctcgtatggg tcatcctgtg   300
tttggcggcg gcacgaagtt aaccgttctt ggccag                             336
```

<210> SEQ ID NO 115
<211> LENGTH: 339
<212> TYPE: DNA
<213> ORGANISM: Artificial
<220> FEATURE:
<223> OTHER INFORMATION: VL

<400> SEQUENCE: 115

```
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc gctacttatg gtaagggtgt tactcctcct   300
gtgtttggcg gcggcacgaa gttaaccgtt cttggccag                          339
```

<210> SEQ ID NO 116
<211> LENGTH: 339
<212> TYPE: DNA
<213> ORGANISM: Artificial
<220> FEATURE:
<223> OTHER INFORMATION: VL

<400> SEQUENCE: 116

```
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339
```

```
<210> SEQ ID NO 117
<211> LENGTH: 336
<212> TYPE: DNA
<213> ORGANISM: Artificial
<220> FEATURE:
<223> OTHER INFORMATION: VL

<400> SEQUENCE: 117
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc caggcttgga cttctaagat ggctggtgtg   300
tttggcggcg gcacgaagtt aaccgttctt ggccag                             336

<210> SEQ ID NO 118
<211> LENGTH: 336
<212> TYPE: DNA
<213> ORGANISM: Artificial
<220> FEATURE:
<223> OTHER INFORMATION: VL

<400> SEQUENCE: 118
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc caggcttgga cttctaagat ggctggtgtg   300
tttggcggcg gcacgaagtt aaccgttctt ggccag                             336

<210> SEQ ID NO 119
<211> LENGTH: 339
<212> TYPE: DNA
<213> ORGANISM: Artificial
<220> FEATURE:
<223> OTHER INFORMATION: VL

<400> SEQUENCE: 119
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339

<210> SEQ ID NO 120
<211> LENGTH: 339
<212> TYPE: DNA
<213> ORGANISM: Artificial
<220> FEATURE:
<223> OTHER INFORMATION: VL

<400> SEQUENCE: 120
gatatcgcac tgacccagcc agcttcagtg agcggctcac caggtcagag cattaccatc    60
tcgtgtacgg gtactagcag cgatgttggt tcttataatt atgtgaattg gtaccagcag   120
```

| | |
|---|---:|
| catcccggga aggcgccgaa acttatgatt tatggtgttt ctaagcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc ggtacttttg ctggtggttc ttattatggt | 300 |
| gtgtttggcg gcggcacgaa gttaaccgtt cttggccag | 339 |

<210> SEQ ID NO 121
<211> LENGTH: 339
<212> TYPE: DNA
<213> ORGANISM: Artificial
<220> FEATURE:
<223> OTHER INFORMATION: VL

<400> SEQUENCE: 121

| | |
|---|---:|
| gatatcgcac tgacccagcc agcttcagtg agcggctcac caggtcagag cattaccatc | 60 |
| tcgtgtacgg gtactagcag cgatgttggt tcttataatt atgtgaattg gtaccagcag | 120 |
| catcccggga aggcgccgaa acttatgatt tatggtgttt ctaagcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc ggtacttttg ctggtggttc ttattatggt | 300 |
| gtgtttggcg gcggcacgaa gttaaccgtt cttggccag | 339 |

<210> SEQ ID NO 122
<211> LENGTH: 339
<212> TYPE: DNA
<213> ORGANISM: Artificial
<220> FEATURE:
<223> OTHER INFORMATION: VL

<400> SEQUENCE: 122

| | |
|---|---:|
| gatatcgcac tgacccagcc agcttcagtg agcggctcac caggtcagag cattaccatc | 60 |
| tcgtgtacgg gtactagcag cgatgttggt tcttataatt atgtgaattg gtaccagcag | 120 |
| catcccggga aggcgccgaa acttatgatt tatggtgttt ctaagcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc ggtacttttg ctggtggttc ttattatggt | 300 |
| gtgtttggcg gcggcacgaa gttaaccgtt cttggccag | 339 |

<210> SEQ ID NO 123
<211> LENGTH: 339
<212> TYPE: DNA
<213> ORGANISM: Artificial
<220> FEATURE:
<223> OTHER INFORMATION: VL

<400> SEQUENCE: 123

| | |
|---|---:|
| gatatcgcac tgacccagcc agcttcagtg agcggctcac caggtcagag cattaccatc | 60 |
| tcgtgtacgg gtactagcag cgatgttggt tcttataatt atgtgaattg gtaccagcag | 120 |
| catcccggga aggcgccgaa acttatgatt tatggtgttt ctaagcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc ggtacttttg ctggtggttc ttattatggt | 300 |
| gtgtttggcg gcggcacgaa gttaaccgtt cttggccag | 339 |

<210> SEQ ID NO 124
<211> LENGTH: 339
<212> TYPE: DNA
<213> ORGANISM: Artificial

<220> FEATURE:
<223> OTHER INFORMATION: VL

<400> SEQUENCE: 124

```
gatatcgcac tgacccagcc agcttcagtg agcggctcac caggtcagag cattaccatc    60
tcgtgtactg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339
```

<210> SEQ ID NO 125
<211> LENGTH: 339
<212> TYPE: DNA
<213> ORGANISM: Artificial
<220> FEATURE:
<223> OTHER INFORMATION: VL

<400> SEQUENCE: 125

```
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339
```

<210> SEQ ID NO 126
<211> LENGTH: 339
<212> TYPE: DNA
<213> ORGANISM: Artificial
<220> FEATURE:
<223> OTHER INFORMATION: VL

<400> SEQUENCE: 126

```
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339
```

<210> SEQ ID NO 127
<211> LENGTH: 345
<212> TYPE: DNA
<213> ORGANISM: Artificial
<220> FEATURE:
<223> OTHER INFORMATION: VH

<400> SEQUENCE: 127

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcact atcaatccgg tttctggcaa tacgtcttac   180
gcgcagaagt tcagggccg ggtgaccatg acccgtgata ccagcattag caccgcgtat   240
```

```
atggaactga gcagcctgcg tagcgaagat acggccgtgt attattgcgc gcgtggtggt      300
tggtttgatt attggggcca aggcaccctg gtgacggtta gctca                     345
```

<210> SEQ ID NO 128
<211> LENGTH: 345
<212> TYPE: DNA
<213> ORGANISM: Artificial
<220> FEATURE:
<223> OTHER INFORMATION: VH

<400> SEQUENCE: 128

```
caggtgcaat tggttcagag cggcgcggaa gtgaaaaaac cgggcgcgag cgtgaaagtg      60
agctgcaaag cctccggata tacctttact tcttcttata ttaattgggt ccgccaagcc      120
cctgggcagg gtctcgagtg gatgggcact atcaatccgg tttctggcaa tacgtcttac      180
gcgcagaagt ttcagggccg ggtgaccatg acccgtgata ccagcattag caccgcgtat      240
atggaactga gcagcctgcg tagcgaagat acggccgtgt attattgcgc gcgtggtggt      300
tggtttgatt attggggcca aggcaccctg gtgacggtta gctca                     345
```

<210> SEQ ID NO 129
<211> LENGTH: 345
<212> TYPE: DNA
<213> ORGANISM: Artificial
<220> FEATURE:
<223> OTHER INFORMATION: VH

<400> SEQUENCE: 129

```
caggtgcaat tggttcagag cggcgcggaa gtgaaaaaac cgggcgcgag cgtgaaagtg      60
agctgcaaag cctccggata tacctttact tcttcttata ttaattgggt ccgccaagcc      120
cctgggcagg gtctcgagtg gatgggcact atcaatccgg tttctggcaa tacgtcttac      180
gcgcagaagt ttcagggccg ggtgaccatg acccgtgata ccagcattag caccgcgtat      240
atggaactga gcagcctgcg tagcgaagat acggccgtgt attattgcgc gcgtggtggt      300
tggtttgatt attggggcca aggcaccctg gtgacggtta gctca                     345
```

<210> SEQ ID NO 130
<211> LENGTH: 345
<212> TYPE: DNA
<213> ORGANISM: Artificial
<220> FEATURE:
<223> OTHER INFORMATION: VH

<400> SEQUENCE: 130

```
caggtgcaat tggttcagag cggcgcggaa gtgaaaaaac cgggcgcgag cgtgaaagtg      60
agctgcaaag cctccggata tacctttact tcttcttata ttaattgggt ccgccaagcc      120
cctgggcagg gtctcgagtg gatgggcact atcaatccgg tttctggcaa tacgtcttac      180
gcgcagaagt ttcagggccg ggtgaccatg acccgtgata ccagcattag caccgcgtat      240
atggaactga gcagcctgcg tagcgaagat acggccgtgt attattgcgc gcgtggtggt      300
tggtttgatt attggggcca aggcaccctg gtgacggtta gctca                     345
```

<210> SEQ ID NO 131
<211> LENGTH: 345
<212> TYPE: DNA
<213> ORGANISM: Artificial
<220> FEATURE:
<223> OTHER INFORMATION: VH

<400> SEQUENCE: 131

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcatg attaatgctc ctattggtac tactcgttat   180
gctcagaagt ttcagggtcg ggtgaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                  345
```

<210> SEQ ID NO 132
<211> LENGTH: 345
<212> TYPE: DNA
<213> ORGANISM: Artificial
<220> FEATURE:
<223> OTHER INFORMATION: VH

<400> SEQUENCE: 132

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggccag attaatgctg cttctggtat gactcgttat   180
gctcagaagt ttcagggtcg ggtgaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                  345
```

<210> SEQ ID NO 133
<211> LENGTH: 345
<212> TYPE: DNA
<213> ORGANISM: Artificial
<220> FEATURE:
<223> OTHER INFORMATION: VH

<400> SEQUENCE: 133

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcatg attaatgctc ctattggtac tactcgttat   180
gctcagaagt ttcagggtcg ggtgaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                  345
```

<210> SEQ ID NO 134
<211> LENGTH: 345
<212> TYPE: DNA
<213> ORGANISM: Artificial
<220> FEATURE:
<223> OTHER INFORMATION: VH

<400> SEQUENCE: 134

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcact atcaatccgg tttctggcaa tacgcgttac   180
gcgcagaagt ttcagggccg ggtgaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                  345
```

<210> SEQ ID NO 135
<211> LENGTH: 345
<212> TYPE: DNA
<213> ORGANISM: Artificial
<220> FEATURE:
<223> OTHER INFORMATION: VH

<400> SEQUENCE: 135

| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggcact atcaatccgg tttctggctc tacgtcttac | 180 |
| gcgcagaagt ttcagggccg ggtgaccatg acccgtgata ccagcattag caccgcgtat | 240 |
| atggaactga gcagcctgcg tagcgaagat acggccgtgt attattgcgc gcgtggtggt | 300 |
| tggtttgatt attggggcca aggcaccctg gtgacggtta gctca | 345 |

<210> SEQ ID NO 136
<211> LENGTH: 345
<212> TYPE: DNA
<213> ORGANISM: Artificial
<220> FEATURE:
<223> OTHER INFORMATION: VH

<400> SEQUENCE: 136

| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggccag attaatgctg cttctggtat gactcgttat | 180 |
| gctcagaagt ttcagggtcg ggtcaccatg acccgtgata ccagcattag caccgcgtat | 240 |
| atggaactga gcagcctgcg tagcgaagat acggccgtgt attattgcgc gcgtggtggt | 300 |
| tggtttgatt attggggcca aggcaccctg gtgacggtta gctca | 345 |

<210> SEQ ID NO 137
<211> LENGTH: 345
<212> TYPE: DNA
<213> ORGANISM: Artificial
<220> FEATURE:
<223> OTHER INFORMATION: VH

<400> SEQUENCE: 137

| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggcaat attaatgctg ctgctggtat tactctttat | 180 |
| gctcagaagt ttcagggtcg ggtcaccatg acccgtgata ccagcattag caccgcgtat | 240 |
| atggaactga gcagcctgcg tagcgaagat acggccgtgt attattgcgc gcgtggtggt | 300 |
| tggtttgatt attggggcca aggcaccctg gtgacggtta gctca | 345 |

<210> SEQ ID NO 138
<211> LENGTH: 345
<212> TYPE: DNA
<213> ORGANISM: Artificial
<220> FEATURE:
<223> OTHER INFORMATION: VH

<400> SEQUENCE: 138

| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |

```
cctgggcagg gtctcgagtg gatgggcact attaatcctc ctactggagg tacttattat    180
gctcagaagt ttcagggtcg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                    345
```

<210> SEQ ID NO 139
<211> LENGTH: 345
<212> TYPE: DNA
<213> ORGANISM: Artificial
<220> FEATURE:
<223> OTHER INFORMATION: VH

<400> SEQUENCE: 139

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc    120
cctgggcagg gtctcgagtg gatgggcggt attaatcctc ctgctggtac tacttcttat    180
gctcagaagt ttcagggtcg ggtcaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                    345
```

<210> SEQ ID NO 140
<211> LENGTH: 345
<212> TYPE: DNA
<213> ORGANISM: Artificial
<220> FEATURE:
<223> OTHER INFORMATION: VH

<400> SEQUENCE: 140

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc    120
cctgggcagg gtctcgagtg gatgggcaat attaatcctg ctactggtca tgctgattat    180
gctcagaagt ttcagggtcg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                    345
```

<210> SEQ ID NO 141
<211> LENGTH: 217
<212> TYPE: PRT
<213> ORGANISM: Artificial
<220> FEATURE:
<223> OTHER INFORMATION: light chain

<400> SEQUENCE: 141

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
```

```
                85                  90                  95
Ser Tyr Tyr Gly Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 142
<211> LENGTH: 217
<212> TYPE: PRT
<213> ORGANISM: Artificial
<220> FEATURE:
<223> OTHER INFORMATION: light chain

<400> SEQUENCE: 142

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215
```

```
<210> SEQ ID NO 143
<211> LENGTH: 217
<212> TYPE: PRT
<213> ORGANISM: Artificial
<220> FEATURE:
<223> OTHER INFORMATION: light chain

<400> SEQUENCE: 143
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

```
<210> SEQ ID NO 144
<211> LENGTH: 217
<212> TYPE: PRT
<213> ORGANISM: Artificial
<220> FEATURE:
<223> OTHER INFORMATION: light chain

<400> SEQUENCE: 144
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 145
<211> LENGTH: 217
<212> TYPE: PRT
<213> ORGANISM: Artificial
<220> FEATURE:
<223> OTHER INFORMATION: light chain

<400> SEQUENCE: 145

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
        130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 146
<211> LENGTH: 445

```
<212> TYPE: PRT
<213> ORGANISM: Artificial
<220> FEATURE:
<223> OTHER INFORMATION: heavy chain

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

```
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 147
<211> LENGTH: 445
<212> TYPE: PRT
<213> ORGANISM: Artificial
<220> FEATURE:
<223> OTHER INFORMATION: heavy chain

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gln Ile Asn Ala Ala Ser Gly Met Thr Arg Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300
```

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 148
<211> LENGTH: 445
<212> TYPE: PRT
<213> ORGANISM: Artificial
<220> FEATURE:
<223> OTHER INFORMATION: heavy chain

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Asn Ile Asn Ala Ala Gly Ile Thr Leu Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Gly Gly Trp Phe Asp Tyr Trp Gly Gln Gly Thr Leu Val Thr
        100                 105                 110

Val Ser Ser Ala Ser Thr Lys Gly Pro Ser Val Phe Pro Leu Ala Pro
    115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Arg Val Glu Pro Lys Ser Cys Asp Lys Thr His Thr Cys
210                 215                 220

```
Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 149
<211> LENGTH: 445
<212> TYPE: PRT
<213> ORGANISM: Artificial
<220> FEATURE:
<223> OTHER INFORMATION: heavy chain

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gly Ile Asn Pro Pro Ala Gly Thr Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140
```

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 150
<211> LENGTH: 445
<212> TYPE: PRT
<213> ORGANISM: Artificial
<220> FEATURE:
<223> OTHER INFORMATION: heavy chain

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Asn Ile Asn Pro Ala Thr Gly His Ala Asp Tyr Ala Gln Lys Phe
        50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 151
<211> LENGTH: 217
<212> TYPE: PRT
<213> ORGANISM: Artificial
<220> FEATURE:
<223> OTHER INFORMATION: light chain
```

<400> SEQUENCE: 151

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
        210                 215

<210> SEQ ID NO 152
<211> LENGTH: 217
<212> TYPE: PRT
<213> ORGANISM: Artificial
<220> FEATURE:
<223> OTHER INFORMATION: light chain

<400> SEQUENCE: 152

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
210                 215

<210> SEQ ID NO 153
<211> LENGTH: 217
<212> TYPE: PRT
<213> ORGANISM: Artificial
<220> FEATURE:
<223> OTHER INFORMATION: light chain

<400> SEQUENCE: 153

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
                35                  40                  45

Met Ile Tyr Gly Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
                115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
210                 215

<210> SEQ ID NO 154
<211> LENGTH: 217
<212> TYPE: PRT
<213> ORGANISM: Artificial
<220> FEATURE:
<223> OTHER INFORMATION: light chain

<400> SEQUENCE: 154

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
             20                  25                  30

Asn Tyr Val Asn Trp Tyr Gln Gln His Pro Gly Lys Ala Pro Lys Leu
         35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 155
<211> LENGTH: 217
<212> TYPE: PRT
<213> ORGANISM: Artificial
<220> FEATURE:
<223> OTHER INFORMATION: light chain

<400> SEQUENCE: 155

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
             20                  25                  30

Asn Tyr Val Asn Trp Tyr Gln Gln His Pro Gly Lys Ala Pro Lys Leu
         35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140
```

```
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 156
<211> LENGTH: 441
<212> TYPE: PRT
<213> ORGANISM: Artificial
<220> FEATURE:
<223> OTHER INFORMATION: heavy chain

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Thr Ile Asn Pro Val Ser Gly Ser Thr Ser Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285
```

```
Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 157
<211> LENGTH: 441
<212> TYPE: PRT
<213> ORGANISM: Artificial
<220> FEATURE:
<223> OTHER INFORMATION: heavy chain

<400> SEQUENCE: 157

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gln Ile Asn Ala Ala Ser Gly Met Thr Arg Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205
```

```
Val Asp Lys Thr Val Glu Arg Lys Cys Cys Val Glu Cys Pro Pro Cys
    210                 215                 220
Pro Ala Pro Pro Val Ala Gly Pro Ser Val Phe Leu Phe Pro Pro Lys
225                 230                 235                 240
Pro Lys Asp Thr Leu Met Ile Ser Arg Thr Pro Glu Val Thr Cys Val
            245                 250                 255
Val Val Asp Val Ser His Glu Asp Pro Glu Val Gln Phe Asn Trp Tyr
        260                 265                 270
Val Asp Gly Val Glu Val His Asn Ala Lys Thr Lys Pro Arg Glu Glu
    275                 280                 285
Gln Phe Asn Ser Thr Phe Arg Val Val Ser Val Leu Thr Val Val His
    290                 295                 300
Gln Asp Trp Leu Asn Gly Lys Glu Tyr Lys Cys Lys Val Ser Asn Lys
305                 310                 315                 320
Gly Leu Pro Ala Pro Ile Glu Lys Thr Ile Ser Lys Thr Lys Gly Gln
            325                 330                 335
Pro Arg Glu Pro Gln Val Tyr Thr Leu Pro Pro Ser Arg Glu Glu Met
        340                 345                 350
Thr Lys Asn Gln Val Ser Leu Thr Cys Leu Val Lys Gly Phe Tyr Pro
    355                 360                 365
Ser Asp Ile Ala Val Glu Trp Glu Ser Asn Gly Gln Pro Glu Asn Asn
370                 375                 380
Tyr Lys Thr Thr Pro Pro Met Leu Asp Ser Asp Gly Ser Phe Phe Leu
385                 390                 395                 400
Tyr Ser Lys Leu Thr Val Asp Lys Ser Arg Trp Gln Gln Gly Asn Val
            405                 410                 415
Phe Ser Cys Ser Val Met His Glu Ala Leu His Asn His Tyr Thr Gln
        420                 425                 430
Lys Ser Leu Ser Leu Ser Pro Gly Lys
    435                 440

<210> SEQ ID NO 158
<211> LENGTH: 441
<212> TYPE: PRT
<213> ORGANISM: Artificial
<220> FEATURE:
<223> OTHER INFORMATION: heavy chain

<400> SEQUENCE: 158

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Ser
            20                  25                  30
Tyr Ile Asn Trp Val Arg Gln Ala Pro Gly Gln Gly Leu Glu Trp Met
        35                  40                  45
Gly Asn Ile Asn Ala Ala Ala Gly Ile Thr Leu Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Gly Gly Trp Phe Asp Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
```

Cys Ser Arg Ser Thr Ser Glu Ser Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 159
<211> LENGTH: 441
<212> TYPE: PRT
<213> ORGANISM: Artificial
<220> FEATURE:
<223> OTHER INFORMATION: heavy chain

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gly Ile Asn Pro Pro Ala Gly Thr Thr Ser Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Gly Trp Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
                180                 185                 190

Thr Gln Thr Tyr Thr Cys Asn Val Asp His Lys Pro Ser Asn Thr Lys
                195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
                260                 265                 270

Val Asp Gly Val Glu Val His Asn Ala Lys Thr Lys Pro Arg Glu Glu
                275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
                355                 360                 365

Ser Asp Ile Ala Val Glu Trp Glu Ser Asn Gly Gln Pro Glu Asn Asn
                370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
                435                 440

<210> SEQ ID NO 160
<211> LENGTH: 441

<212> TYPE: PRT
<213> ORGANISM: Artificial
<220> FEATURE:
<223> OTHER INFORMATION: heavy chain

<400> SEQUENCE: 160

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Asn Ile Asn Pro Ala Thr Gly His Ala Asp Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380
```

```
Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 161
<211> LENGTH: 651
<212> TYPE: DNA
<213> ORGANISM: Artificial
<220> FEATURE:
<223> OTHER INFORMATION: light chain

<400> SEQUENCE: 161
cagagcgccc tgacccagcc cgccagcgtg tccggcagcc caggccagtc tatcacaatc      60
agctgcaccg gcacctccag cgacgtgggc agctacaact acgtgaactg gtatcagcag     120
caccccggca aggccccaa gctgatgatc tacggcgtga gcaagaggcc cagcggcgtg     180
tccaacaggt tcagcggcag caagagcggc aacaccgcca gcctgacaat cagtgggctg     240
caggctgagg acgaggccga ctactactgc ggcaccttg ccggcggatc atactacggc     300
gtgttcggcg agggaccaa gctgaccgtg ctgggccagc ctaaggctgc ccccagcgtg     360
accctgttcc cccccagcag cgaggagctg caggccaaca aggccaccct ggtgtgcctg     420
atcagcgact tctacccagg cgccgtgacc gtggcctgga aggccgacag cagccccgtg     480
aaggccggcg tggagaccac cacccccagc aagcagagca acaacaagta cgccgccagc     540
agctacctga gcctgacccc cgagcagtgg aagagccaca ggtcctacag ctgccaggtg     600
acccacgagg gcagcaccgt ggaaaagacc gtggccccaa ccgagtgcag c              651

<210> SEQ ID NO 162
<211> LENGTH: 651
<212> TYPE: DNA
<213> ORGANISM: Artificial
<220> FEATURE:
<223> OTHER INFORMATION: light chain

<400> SEQUENCE: 162
cagagcgccc tgacccagcc cgccagcgtg tccggcagcc caggccagtc tatcacaatc      60
agctgcaccg gcacctccag cgacgtgggc agctacaact acgtgaactg gtatcagcag     120
caccccggca aggccccaa gctgatgatc tacggcgtga gcaagaggcc cagcggcgtg     180
tccaacaggt tcagcggcag caagagcggc aacaccgcca gcctgacaat cagtgggctg     240
caggctgagg acgaggccga ctactactgc ggcaccttg ccggcggatc atactacggc     300
gtgttcggcg agggaccaa gctgaccgtg ctgggccagc ctaaggctgc ccccagcgtg     360
accctgttcc cccccagcag cgaggagctg caggccaaca aggccaccct ggtgtgcctg     420
atcagcgact tctacccagg cgccgtgacc gtggcctgga aggccgacag cagccccgtg     480
aaggccggcg tggagaccac cacccccagc aagcagagca acaacaagta cgccgccagc     540
agctacctga gcctgacccc cgagcagtgg aagagccaca ggtcctacag ctgccaggtg     600
acccacgagg gcagcaccgt ggaaaagacc gtggccccaa ccgagtgcag c              651

<210> SEQ ID NO 163
<211> LENGTH: 651
```

```
<212> TYPE: DNA
<213> ORGANISM: Artificial
<220> FEATURE:
<223> OTHER INFORMATION: light chain

<400> SEQUENCE: 163
cagagcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtactttg ctggtggttc ttattatggt      300
gtgtttggcg gcggcacgaa gttaaccgtc ctaggtcagc ccaaggctgc ccctcggtc      360 actctgttcc cgcccctcc tgaggagctt caagccaaca aggccacact ggtgtgtctc      420
ataagtgact tctacccggg agccgtgaca gtggcctgga aggcagatag cagccccgtc     480
aaggcgggag tggagaccac cacaccctcc aaacaaagca acaacaagta cgcggccagc    540
agctatctga gcctgacgcc tgagcagtgg aagtcccaca gaagctacag ctgccaggtc     600
acgcatgaag ggagcaccgt ggagaagaca gtggccccta cagaatgttc a              651

<210> SEQ ID NO 164
<211> LENGTH: 651
<212> TYPE: DNA
<213> ORGANISM: Artificial
<220> FEATURE:
<223> OTHER INFORMATION: light chain

<400> SEQUENCE: 164
cagagcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtactttg ctggtggttc ttattatggt      300
gtgtttggcg gcggcacgaa gttaaccgtc ctaggtcagc ccaaggctgc ccctcggtc      360 actctgttcc cgcccctcc tgaggagctt caagccaaca aggccacact ggtgtgtctc      420
ataagtgact tctacccggg agccgtgaca gtggcctgga aggcagatag cagccccgtc     480
aaggcgggag tggagaccac cacaccctcc aaacaaagca acaacaagta cgcggccagc    540
agctatctga gcctgacgcc tgagcagtgg aagtcccaca gaagctacag ctgccaggtc     600
acgcatgaag ggagcaccgt ggagaagaca gtggccccta cagaatgttc a              651

<210> SEQ ID NO 165
<211> LENGTH: 651
<212> TYPE: DNA
<213> ORGANISM: Artificial
<220> FEATURE:
<223> OTHER INFORMATION: light chain

<400> SEQUENCE: 165
cagagcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
```

| | |
|---|---|
| caagcggaag acgaagcgga ttattattgc ggtacttttg ctggtggttc ttattatggt | 300 |
| gtgtttggcg gcggcacgaa gttaaccgtc ctaggtcagc ccaaggctgc cccctcggtc | 360 |
| actctgttcc cgccctcctc tgaggagctt caagccaaca aggccacact ggtgtgtctc | 420 |
| ataagtgact tctacccggg agccgtgaca gtggcctgga aggcagatag cagccccgtc | 480 |
| aaggcgggag tggagaccac cacaccctcc aaacaaagca caacaagta cgcggccagc | 540 |
| agctatctga gcctgacgcc tgagcagtgg aagtcccaca aagctacag ctgccaggtc | 600 |
| acgcatgaag ggagcaccgt ggagaagaca gtggccccta cagaatgttc a | 651 |

<210> SEQ ID NO 166
<211> LENGTH: 1335
<212> TYPE: DNA
<213> ORGANISM: Artificial
<220> FEATURE:
<223> OTHER INFORMATION: heavy chain

<400> SEQUENCE: 166

| | |
|---|---|
| caggtgcagc tggtgcagag cggagctgag gtgaagaagc caggcgccag cgtcaaggtg | 60 |
| tcctgcaagg ccagcggcta caccttcacc agcagctaca tcaactgggt ccgccaggct | 120 |
| cctgggcagg gactggagtg gatgggcacc atcaaccccg tgtccggcag caccagctac | 180 |
| gcccagaagt tccagggcag agtcaccatg accaggggaca ccagcatcag caccgcctac | 240 |
| atggagctgt ccaggctgag aagcgacgac accgccgtgt actactgcgc caggggcggc | 300 |
| tggttcgact actggggcca gggcaccctg gtgaccgtgt cctcagctag caccaagggc | 360 |
| ccagccgtgt tccccctggc ccccagcagc aagagcacct ccggcggcac agccgccctg | 420 |
| ggctgcctgg tgaaggacta cttccccgag cccgtgaccg tgtcctggaa cagcggagcc | 480 |
| ctgaccagcg gcgtgcacac cttccccgcc gtgctgcaga gcagcggcct gtacagcctg | 540 |
| tccagcgtgg tgacagtgcc cagcagcagc ctgggcaccc agacctacat ctgcaacgtg | 600 |
| aaccacaagc ccagcaacac caaggtggac aagagagtgg agcccaagag ctgcgacaag | 660 |
| acccacacct gccccccctg cccagcccc gaagctgcag gcggcccttc cgtgttcctg | 720 |
| ttccccccca gccccaagga caccctgatg atcagcagga ccccgaggt gacctgcgtg | 780 |
| gtggtggacg tgagccacga ggacccagag gtgaagttca actggtacgt ggacggcgtg | 840 |
| gaggtgcaca cgccaagac caagcccaga gaggagcagt acaacagcac ctacagggtg | 900 |
| gtgtccgtgc tgaccgtgct gcaccaggac tggctgaacg gcaaagaata caagtgcaag | 960 |
| gtctccaaca aggccctgcc tgcccccatc gaaaagacca tcagcaaggc caagggccag | 1020 |
| ccacgggagc cccaggtgta caccctgccc ccttctcggg aggagatgac caagaaccag | 1080 |
| gtgtccctga cctgtctggt gaagggcttc taccccagcg acatcgccgt ggagtgggag | 1140 |
| agcaacggcc agcccgagaa caactacaag accacccccc cagtgctgga cagcgacggc | 1200 |
| agcttcttcc tgtacagcaa gctgaccgtg gacaagagca ggtggcagca gggcaacgtg | 1260 |
| ttcagctgca gcgtgatgca cgaggccctg cacaaccact acacccagaa gagcctgagc | 1320 |
| ctgtcacccg gcaag | 1335 |

<210> SEQ ID NO 167
<211> LENGTH: 1335
<212> TYPE: DNA
<213> ORGANISM: Artificial
<220> FEATURE:
<223> OTHER INFORMATION: heavy chain

<400> SEQUENCE: 167

-continued

```
caggtgcagc tggtgcagag cggagctgag gtgaagaagc caggcgccag cgtcaaggtg      60
tcctgcaagg ccagcggcta caccttcacc agcagctaca tcaactgggt gcgccaggct     120
ccagggcagg gactggagtg gatgggccag atcaacgccg ccagcggcat gaccagatac     180
gcccagaagt tccagggcag agtcacaatg accaggtaca cctctatcag caccgcctac     240
atggagctgt ccaggctgag aagcgacgac accgccgtgt actactgcgc caggggcggc     300
tggttcgact actggggcca gggcaccctg gtgaccgtgt cctcagctag caccaagggc     360
ccagcgtgt tccccctggc cccagcagc aagagcacct ccggcggcac agccgccctg     420
ggctgcctgg tgaaggacta cttccccgag cccgtgaccg tgtcctggaa cagcggagcc     480
ctgaccagcg gcgtgcacac cttccccgcc gtgctgcaga gcagcggcct gtacagcctg     540
tccagcgtgt tgacagtgcc cagcagcagc ctgggcaccc agacctacat ctgcaacgtg     600
aaccacaagc ccagcaacac caaggtggac aagagagtgg agcccaagag ctgcgacaag     660
acccacacct gccccccctg cccagccccc gaagctgcag gcggccctc cgtgttcctg     720
ttccccccca gcccaagga caccctgatg atcagcagga ccccgaggt gacctgcgtg     780
gtggtggacg tgagccacga ggacccagag gtgaagttca actggtacgt ggacggcgtg     840
gaggtgcaca acgccaagac caagcccaga gaggagcagt acaacagcac ctacagggtg     900
gtgtccgtgc tgaccgtgct gcaccaggac tggctgaacg gcaaagaata caagtgcaag     960
gtctccaaca aggccctgcc tgcccccatc gaaaagacca tcagcaaggc caagggccag    1020
ccacgggagc cccaggtgta caccctgccc ccttctcggg aggagatgac caagaaccag    1080
gtgtccctga cctgtctggt gaagggcttc taccccagcg acatcgccgt ggagtgggag    1140
agcaacggcc agcccgagaa caactacaag accaccccccc cagtgctgga cagcgacggc    1200
agcttcttcc tgtacagcaa gctgaccgtg gacaagagca ggtggcagca gggcaacgtg    1260
ttcagctgca gcgtgatgca cgaggccctg cacaaccact acacccagaa gagcctgagc    1320
ctgtcacccg gcaag                                                    1335
```

<210> SEQ ID NO 168
<211> LENGTH: 1335
<212> TYPE: DNA
<213> ORGANISM: Artificial
<220> FEATURE:
<223> OTHER INFORMATION: heavy chain

<400> SEQUENCE: 168

```
caggtgcaat tggttcagag cggcgcggaa gtgaaaaaac cgggcgcgag cgtgaaagtg      60
agctgcaaag cctccggata ccctttact tcttcttata ttaattgggt ccgccaagcc     120
cctgggcagg gtctcgagtg gatgggcaat attaatgctg ctgctggtat tactctttat     180
gctcagaagt ttcagggtcg ggtcaccatg accgtgata ccagcattag caccgcgtat     240
atggaactga gccgcctgcg tagcgatgat acggccgtgt attattgcgc gcgtggtggt     300
tggtttgatt attgggggcca aggcaccctg gtgacggtta gctcagcctc caccaagggt     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtgcacac cttccccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagagagttg agcccaaatc ttgtgacaaa     660
```

| | | |
|---|---|---|
| actcacacat gcccaccgtg cccagcacct gaagcagcgg ggggaccgtc agtcttcctc | 720 | |
| ttccccccaa aacccaagga caccctcatg atctcccgga cccctgaggt cacatgcgtg | 780 | |
| gtggtggacg tgagccacga agaccctgag gtcaagttca actggtacgt ggacggcgtg | 840 | |
| gaggtgcata atgccaagac aaagccgcgg gaggagcagt acaacagcac gtaccgggtg | 900 | |
| gtcagcgtcc tcaccgtcct gcaccaggac tggctgaatg gcaaggagta caagtgcaag | 960 | |
| gtctccaaca aagcccctcc agcccccatc gagaaaacca tctccaaagc caaagggcag | 1020 | |
| ccccgagaac cacaggtgta caccctgccc ccatcccggg aggagatgac caagaaccag | 1080 | |
| gtcagcctga cctgcctggt caaaggcttc tatcccagcg acatcgccgt ggagtgggag | 1140 | |
| agcaatgggc agccggagaa caactacaag accacgcctc ccgtgctgga ctccgacggc | 1200 | |
| tccttcttcc tctacagcaa gctcaccgtg gacaagagca ggtggcagca ggggaacgtc | 1260 | |
| ttctcatgct ccgtgatgca tgaggctctg cacaaccact acacgcagaa gagcctctcc | 1320 | |
| ctgtctccgg gtaaa | 1335 | |

<210> SEQ ID NO 169
<211> LENGTH: 1335
<212> TYPE: DNA
<213> ORGANISM: Artificial
<220> FEATURE:
<223> OTHER INFORMATION: heavy chain

<400> SEQUENCE: 169

| | | |
|---|---|---|
| caggtgcaat tggttcagag cggcgcggaa gtgaaaaaac cgggcgcgag cgtgaaagtg | 60 | |
| agctgcaaag cctccggata tacctttact tcttcttata ttaattgggt ccgccaagcc | 120 | |
| cctgggcagg gtctcgagtg gatgggcggt attaatcctc tgctggtac tacttcttat | 180 | |
| gctcagaagt ttcagggtcg ggtcaccatg acccgtgata ccagcattag caccgcgtat | 240 | |
| atggaactga gccgcctgcg tagcgatgat acggccgtgt attattgcgc gcgtggtggt | 300 | |
| tggtttgatt attggggcca aggcaccctg gtgacggtta gctcagcctc caccaagggt | 360 | |
| ccatcggtct tccccctggc accctcctcc aagagcacct ctgggggcac agcggccctg | 420 | |
| ggctgcctgg tcaaggacta cttccccgaa ccggtgacgg tgtcgtggaa ctcaggcgcc | 480 | |
| ctgaccagcg gcgtgcacac cttcccggct gtcctacagt cctcaggact ctactccctc | 540 | |
| agcagcgtgt gaccgtgcc ctccagcagc ttgggcaccc agacctacat ctgcaacgtg | 600 | |
| aatcacaagc ccagcaacac caaggtggac aagagagttg agcccaaatc ttgtgacaaa | 660 | |
| actcacacat gcccaccgtg cccagcacct gaagcagcgg ggggaccgtc agtcttcctc | 720 | |
| ttccccccaa aacccaagga caccctcatg atctcccgga cccctgaggt cacatgcgtg | 780 | |
| gtggtggacg tgagccacga agaccctgag gtcaagttca actggtacgt ggacggcgtg | 840 | |
| gaggtgcata atgccaagac aaagccgcgg gaggagcagt acaacagcac gtaccgggtg | 900 | |
| gtcagcgtcc tcaccgtcct gcaccaggac tggctgaatg gcaaggagta caagtgcaag | 960 | |
| gtctccaaca aagcccctcc agcccccatc gagaaaacca tctccaaagc caaagggcag | 1020 | |
| ccccgagaac cacaggtgta caccctgccc ccatcccggg aggagatgac caagaaccag | 1080 | |
| gtcagcctga cctgcctggt caaaggcttc tatcccagcg acatcgccgt ggagtgggag | 1140 | |
| agcaatgggc agccggagaa caactacaag accacgcctc ccgtgctgga ctccgacggc | 1200 | |
| tccttcttcc tctacagcaa gctcaccgtg gacaagagca ggtggcagca ggggaacgtc | 1260 | |
| ttctcatgct ccgtgatgca tgaggctctg cacaaccact acacgcagaa gagcctctcc | 1320 | |
| ctgtctccgg gtaaa | 1335 | |

<210> SEQ ID NO 170
<211> LENGTH: 1335
<212> TYPE: DNA
<213> ORGANISM: Artificial
<220> FEATURE:
<223> OTHER INFORMATION: heavy chain

<400> SEQUENCE: 170

| | |
|---|---|
| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggcaat attaatcctg ctactggtca tgctgattat | 180 |
| gctcagaagt ttcagggtcg ggtgaccatg acccgtgata ccagcattag caccgcgtat | 240 |
| atggaactga ccgcctgcg tagcgatgat acggccgtgt attattgcgc gcgtggtggt | 300 |
| tggtttgatt attggggcca aggcaccctg gtgacggtta gctcagcctc caccaagggt | 360 |
| ccatcggtct tccccctggc accctcctcc aagagcacct ctgggggcac agcggccctg | 420 |
| ggctgcctgg tcaaggacta cttccccgaa ccggtgacgg tgtcgtggaa ctcaggcgcc | 480 |
| ctgaccagcg gcgtgcacac cttcccggct gtcctacagt cctcaggact ctactccctc | 540 |
| agcagcgtgg tgaccgtgcc ctccagcagc ttgggcaccc agacctacat ctgcaacgtg | 600 |
| aatcacaagc ccagcaacac caaggtggac aagagagttg agcccaaatc ttgtgacaaa | 660 |
| actcacacat gcccaccgtg cccagcacct gaagcagcgg ggggaccgtc agtcttcctc | 720 |
| ttccccccaa aacccaagga caccctcatg atctcccgga cccctgaggt cacatgcgtg | 780 |
| gtggtggacg tgagccacga agaccctgag gtcaagttca actggtacgt ggacggcgtg | 840 |
| gaggtgcata atgccaagac aaagccgcgg gaggagcagt acaacagcac gtaccgggtg | 900 |
| gtcagcgtcc tcaccgtcct gcaccaggac tggctgaatg gcaaggagta caagtgcaag | 960 |
| gtctccaaca aagccctccc agcccccatc gagaaaacca tctccaaagc caaagggcag | 1020 |
| ccccgagaac cacaggtgta caccctgccc ccatcccggg aggagatgac caagaaccag | 1080 |
| gtcagcctga cctgcctggt caaaggcttc tatcccagcg acatcgccgt ggagtgggag | 1140 |
| agcaatgggc agccggagaa caactacaag accacgcctc ccgtgctgga ctccgacggc | 1200 |
| tccttcttcc tctacagcaa gctcaccgtg gacaagagca ggtggcagca ggggaacgtc | 1260 |
| ttctcatgct ccgtgatgca tgaggctctg cacaaccact acacgcagaa gagcctctcc | 1320 |
| ctgtctccgg gtaaa | 1335 |

<210> SEQ ID NO 171
<211> LENGTH: 651
<212> TYPE: DNA
<213> ORGANISM: Artificial
<220> FEATURE:
<223> OTHER INFORMATION: light chain

<400> SEQUENCE: 171

| | |
|---|---|
| cagagcgccc tgacccagcc cgccagcgtg tccggcagcc caggccagtc tatcacaatc | 60 |
| agctgcaccg gcacctccag cgacgtgggc agctacaact acgtgaactg gtatcagcag | 120 |
| cacccccgca aggcccccaa gctgatgatc tacggcgtga gcaagaggcc cagcggcgtg | 180 |
| tccaacaggt tcagcggcag caagagcggc aacaccgcca gcctgacaat cagtgggctg | 240 |
| caggctgagg acgaggccga ctactactgc ggcacctttg ccggcggatc atactacggc | 300 |
| gtgttcggcg gagggaccaa gctgaccgtg ctgggccagc ctaaggctgc ccccagcgtg | 360 |

-continued

| | |
|---|---|
| accctgttcc cccccagcag cgaggagctg caggccaaca aggccaccct ggtgtgcctg | 420 |
| atcagcgact tctacccagg cgccgtgacc gtggcctgga aggccgacag cagcccgtg | 480 |
| aaggccggcg tggagaccac caccccccagc aagcagagca acaacaagta cgccgccagc | 540 |
| agctacctga gcctgacccc cgagcagtgg aagagccaca ggtcctacag ctgccaggtg | 600 |
| acccacgagg gcagcaccgt ggaaaagacc gtggccccaa ccgagtgcag c | 651 |

<210> SEQ ID NO 172
<211> LENGTH: 651
<212> TYPE: DNA
<213> ORGANISM: Artificial
<220> FEATURE:
<223> OTHER INFORMATION: light chain

<400> SEQUENCE: 172

| | |
|---|---|
| cagagcgccc tgacccagcc cgccagcgtg tccggcagcc caggccagtc tatcacaatc | 60 |
| agctgcaccg gcacctccag cgacgtgggc agctacaact acgtgaactg gtatcagcag | 120 |
| caccccggca aggccccccaa gctgatgatc tacgacgtga gcaagaggcc cagcggcgtg | 180 |
| tccaacaggt tcagcggcag caagagcggc aacaccgcca gcctgacaat cagtgggctg | 240 |
| caggctgagg acgaggccga ctactactgc ggcacctttg ccggcggatc atactacggc | 300 |
| gtgttcggcg gagggaccaa gctgaccgtg ctgggccagc ctaaggctgc ccccagcgtg | 360 |
| accctgttcc cccccagcag cgaggagctg caggccaaca aggccaccct ggtgtgcctg | 420 |
| atcagcgact tctacccagg cgccgtgacc gtggcctgga aggccgacag cagcccgtg | 480 |
| aaggccggcg tggagaccac caccccccagc aagcagagca acaacaagta cgccgccagc | 540 |
| agctacctga gcctgacccc cgagcagtgg aagagccaca ggtcctacag ctgccaggtg | 600 |
| acccacgagg gcagcaccgt ggaaaagacc gtggccccaa ccgagtgcag c | 651 |

<210> SEQ ID NO 173
<211> LENGTH: 651
<212> TYPE: DNA
<213> ORGANISM: Artificial
<220> FEATURE:
<223> OTHER INFORMATION: light chain

<400> SEQUENCE: 173

| | |
|---|---|
| cagagcgcac tgacccagcc agcttcagtg agcggctcac caggtcagag cattaccatc | 60 |
| tcgtgtacgg gtactagcag cgatgttggt tcttataatt atgtgaattg gtaccagcag | 120 |
| catcccggga aggcgccgaa acttatgatt tatggtgttt ctaagcgtcc ctcaggcgtg | 180 |
| agcaaccgtt ttagcggatc caaaagcggc aacaccgcga gcctgaccat tagcggcctg | 240 |
| caagcggaag acgaagcgga ttattattgc ggtacttttg ctggtggttc ttattatggt | 300 |
| gtgtttggcg gcggcacgaa gttaaccgtc ctaggtcagc ccaaggctgc cccctcggtc | 360 |
| actctgttcc cgccctcctc tgaggagctt caagccaaca ggccacact ggtgtgtctc | 420 |
| ataagtgact tctacccggg agccgtgaca gtggcctgga aggcagatag cagcccgtc | 480 |
| aaggcgggag tggagaccac cacaccctcc aaacaaagca acaacaagta cgcggccagc | 540 |
| agctatctga gcctgacgcc tgagcagtgg aagtccaca gaagctacag ctgccaggtc | 600 |
| acgcatgaag ggagcaccgt ggagaagaca gtggccccta cagaatgttc a | 651 |

<210> SEQ ID NO 174
<211> LENGTH: 651
<212> TYPE: DNA
<213> ORGANISM: Artificial
<220> FEATURE:
<223> OTHER INFORMATION: light chain

<400> SEQUENCE: 174

| cagagcgcac | tgacccagcc | agcttcagtg | agcggctcac | caggtcagag | cattaccatc | 60 |
| tcgtgtacgg | gtactagcag | cgatgttggt | tcttataatt | atgtgaattg | gtaccagcag | 120 |
| catcccggga | aggcgccgaa | acttatgatt | tatggtgttt | ctaagcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | ggtacttttg | ctggtggttc | ttattatggt | 300 |
| gtgtttggcg | gcggcacgaa | gttaaccgtc | ctaggtcagc | ccaaggctgc | ccctcggtc | 360 |
| actctgttcc | cgccctcctc | tgaggagctt | caagccaaca | aggccacact | ggtgtgtctc | 420 |
| ataagtgact | tctacccggg | agccgtgaca | gtggcctgga | aggcagatag | cagccccgtc | 480 |
| aaggcgggag | tggagaccac | cacaccctcc | aaacaaagca | caacaagta | cgcggccagc | 540 |
| agctatctga | gcctgacgcc | tgagcagtgg | aagtcccaca | gaagctacag | ctgccaggtc | 600 |
| acgcatgaag | ggagcaccgt | ggagaagaca | gtggccccta | cagaatgttc | a | 651 |

<210> SEQ ID NO 175
<211> LENGTH: 651
<212> TYPE: DNA
<213> ORGANISM: Artificial
<220> FEATURE:
<223> OTHER INFORMATION: light chain

<400> SEQUENCE: 175

| cagagcgcac | tgacccagcc | agcttcagtg | agcggctcac | caggtcagag | cattaccatc | 60 |
| tcgtgtacgg | gtactagcag | cgatgttggt | tcttataatt | atgtgaattg | gtaccagcag | 120 |
| catcccggga | aggcgccgaa | acttatgatt | tatggtgttt | ctaagcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | ggtacttttg | ctggtggttc | ttattatggt | 300 |
| gtgtttggcg | gcggcacgaa | gttaaccgtc | ctaggtcagc | ccaaggctgc | ccctcggtc | 360 |
| actctgttcc | cgccctcctc | tgaggagctt | caagccaaca | aggccacact | ggtgtgtctc | 420 |
| ataagtgact | tctacccggg | agccgtgaca | gtggcctgga | aggcagatag | cagccccgtc | 480 |
| aaggcgggag | tggagaccac | cacaccctcc | aaacaaagca | caacaagta | cgcggccagc | 540 |
| agctatctga | gcctgacgcc | tgagcagtgg | aagtcccaca | gaagctacag | ctgccaggtc | 600 |
| acgcatgaag | ggagcaccgt | ggagaagaca | gtggccccta | cagaatgttc | a | 651 |

<210> SEQ ID NO 176
<211> LENGTH: 1323
<212> TYPE: DNA
<213> ORGANISM: Artificial
<220> FEATURE:
<223> OTHER INFORMATION: heavy chain

<400> SEQUENCE: 176

| caggtgcagc | tggtgcagag | cggagctgag | gtgaagaagc | caggcgccag | cgtcaaggtg | 60 |
| tcctgcaagg | ccagcggcta | caccttcacc | agcagctaca | tcaactgggt | ccgccaggct | 120 |
| cctgggcagg | gactggagtg | gatgggcacc | atcaacccccg | tgtccggcag | caccagctac | 180 |
| gcccagaagt | tccagggcag | agtcaccatg | accaggggaca | ccagcatcag | caccgcctac | 240 |
| atggagctgt | ccaggctgag | aagcgacgac | accgccgtgt | actactgcgc | caggggcggc | 300 |

| | |
|---|---|
| tggttcgact actggggcca gggcaccctg gtgaccgtgt cctcagctag caccaagggc | 360 |
| cccagcgtgt tcccctggc ccctgcagc agaagcacca gcgagagcac agccgccctg | 420 |
| ggctgcctgg tgaaggacta cttccccgag ccagtgaccg tgtcctggaa cagcggagcc | 480 |
| ctgaccagcg gcgtgcacac cttccccgcc gtgctgcaga gcagcggcct gtacagcctg | 540 |
| tccagcgtgg tgaccgtgcc cagcagcaac ttcggcaccc agacctacac ctgcaacgtg | 600 |
| gaccacaagc ccagcaacac caaggtggac aagaccgtgg agaggaagtg ctgcgtggag | 660 |
| tgcccccct gcccagcccc cccagtggcc ggaccctccg tgttcctgtt cccccccaag | 720 |
| cccaaggaca ccctgatgat cagcaggacc cccgaggtga cctgcgtggt ggtggacgtg | 780 |
| agccacgagg acccagaggt gcagttcaac tggtacgtgg acggcgtgga ggtgcacaac | 840 |
| gccaagacca gcccagaga ggaacagttt aacagcacct caggtggt gtccgtgctg | 900 |
| accgtggtgc accaggactg gctgaacggc aagagtaca agtgcaaggt ctccaacaag | 960 |
| ggcctgccag cccccatcga gaaaaccatc agcaagacca agggccagcc acgggagccc | 1020 |
| caggtgtaca ccctgccccc cagccgggag gaaatgacca agaaccaggt gtccctgacc | 1080 |
| tgtctggtga agggcttcta ccccagcgac atcgccgtgg agtgggagag caacggccag | 1140 |
| cccgagaaca actacaagac caccccccc atgctggaca gcgacggcag cttcttcctg | 1200 |
| tacagcaagc tgacagtgga caagagcagg tggcagcagg gcaacgtgtt cagctgcagc | 1260 |
| gtgatgcacg aggccctgca caaccactac acccagaaga gcctgagcct gtccccggc | 1320 |
| aag | 1323 |

<210> SEQ ID NO 177
<211> LENGTH: 1323
<212> TYPE: DNA
<213> ORGANISM: Artificial
<220> FEATURE:
<223> OTHER INFORMATION: heavy chain

<400> SEQUENCE: 177

| | |
|---|---|
| caggtgcagc tggtgcagag cggagctgag gtgaagaagc caggcgccag cgtcaaggtg | 60 |
| tcctgcaagg ccagcggcta caccttcacc agcagctaca tcaactgggt gcgccaggct | 120 |
| ccagggcagg gactggagtg gatgggccag atcaacgccg ccagcggcat gaccagatac | 180 |
| gcccagaagt tccagggcag agtcacaatg accaggggaca cctctatcag caccgcctac | 240 |
| atggagctgt ccaggctgag aagcgacgac accgccgtgt actactgcgc caggggcggc | 300 |
| tggttcgact actggggcca gggcaccctg gtgaccgtgt cctcagctag caccaagggc | 360 |
| cccagcgtgt tcccctggc ccctgcagc agaagcacca gcgagagcac agccgccctg | 420 |
| ggctgcctgg tgaaggacta cttccccgag ccagtgaccg tgtcctggaa cagcggagcc | 480 |
| ctgaccagcg gcgtgcacac cttccccgcc gtgctgcaga gcagcggcct gtacagcctg | 540 |
| tccagcgtgg tgaccgtgcc cagcagcaac ttcggcaccc agacctacac ctgcaacgtg | 600 |
| gaccacaagc ccagcaacac caaggtggac aagaccgtgg agaggaagtg ctgcgtggag | 660 |
| tgcccccct gcccagcccc cccagtggcc ggaccctccg tgttcctgtt cccccccaag | 720 |
| cccaaggaca ccctgatgat cagcaggacc cccgaggtga cctgcgtggt ggtggacgtg | 780 |
| agccacgagg acccagaggt gcagttcaac tggtacgtgg acggcgtgga ggtgcacaac | 840 |
| gccaagacca gcccagaga ggaacagttt aacagcacct caggtggt gtccgtgctg | 900 |
| accgtggtgc accaggactg gctgaacggc aagagtaca agtgcaaggt ctccaacaag | 960 |
| ggcctgccag cccccatcga gaaaaccatc agcaagacca agggccagcc acgggagccc | 1020 |

```
caggtgtaca ccctgccccc cagccgggag gaaatgacca agaaccaggt gtccctgacc    1080
tgtctggtga agggcttcta ccccagcgac atcgccgtgg agtgggagag caacggccag    1140
cccgagaaca actacaagac cacccccccc atgctggaca cgacggcag cttcttcctg    1200 tacagcaagc tgacagtgga caagagcagg tggcagcagg caacgtgtt cagctgcagc    1260 gtgatgcacg aggccctgca caaccactac acccagaaga gcctgagcct gtccccggc    1320 aag                                                                  1323

<210> SEQ ID NO 178
<211> LENGTH: 1323
<212> TYPE: DNA
<213> ORGANISM: Artificial
<220> FEATURE:
<223> OTHER INFORMATION: heavy chain

<400> SEQUENCE: 178
caggtgcaat tggttcagag cggcgcggaa gtgaaaaaac cgggcgcgag cgtgaaagtg      60
agctgcaaag cctccggata tacctttact tcttcttata ttaattgggt ccgccaagcc    120
cctgggcagg gtctcgagtg gatgggcaat attaatgctg ctgctggtat tactcttat    180 gctcagaagt ttcagggtcg ggtcaccatg acccgtgata ccagcattag caccgcgtat    240
atggaactga ccgcctgcg tagcgatgat acggccgtgt attattgcgc cgtggtggt    300 tggtttgatt attgggggcca aggcaccctg gtgacggtta gctcagcttc caccaagggc    360 ccagcgtgt tccccctggc ccctgcagc agaagcacca gcgagagcac agccgccctg    420
ggctgcctgg tgaaggacta cttccccgag cccgtgaccg tgagctggaa cagcggagcc    480
ctgaccagcg gcgtgcacac cttccccgcc gtgctgcaga gcagcggcct gtacagcctg    540
agcagcgtgg tgaccgtgcc cagcagcaac ttcggcaccc agacctacac ctgcaacgtg    600
gaccacaagc ccagcaacac caaggtggac aagaccgtgg agcggaagtg ctgcgtggag    660
tgccccccct gccctgcccc tcctgtggcc ggaccctccg tgttcctgtt cccccccaag    720
cccaaggaca ccctgatgat cagccggacc cccgaggtga cctgcgtggt ggtggacgtg    780
agccacgagg accccgaggt gcagttcaac tggtacgtgg acggcgtgga ggtgcacaac    840
gccaagacca gccccgggga ggaacagttc aacagcacct ccggggtggt gtccgtgctg    900
accgtggtgc accaggactg gctgaacggc aagaataca agtgcaaggt gtccaacaag    960
ggcctgcctg cccccatcga gaaaaccatc agcaagacaa agggccagcc cagggaaccc    1020
caggtgtaca ccctgccccc cagccgggag gaaatgacca agaaccaggt gtccctgacc    1080
tgtctggtga agggcttcta ccccagcgac atcgccgtgg agtgggagag caacggccag    1140
cccgagaaca actacaagac cacccccccc atgctggaca cgacggcag cttcttcctg    1200 tacagcaagc tgacagtgga caagagccgg tggcagcagg caacgtgtt cagctgcagc    1260 gtgatgcacg aggccctgca caaccactac acccagaaga gcctgagcct gtccccggc    1320 aaa                                                                  1323

<210> SEQ ID NO 179
<211> LENGTH: 1323
<212> TYPE: DNA
<213> ORGANISM: Artificial
<220> FEATURE:
<223> OTHER INFORMATION: heavy chain

<400> SEQUENCE: 179
```

| | |
|---|---|
| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggcggt attaatcctc ctgctggtac tacttcttat | 180 |
| gctcagaagt ttcagggtcg ggtcaccatg accgtgata ccagcattag caccgcgtat | 240 |
| atggaactga gccgcctgcg tagcgatgat acggccgtgt attattgcgc gcgtggtggt | 300 |
| tggtttgatt attggggcca aggcaccctg gtgacggtta gctcagcttc caccaagggc | 360 |
| ccagcgtgt tcccctggc ccctgcagc agaagcacca gcgagagcac agccgccctg | 420 |
| ggctgcctgg tgaaggacta cttccccgag cccgtgaccg tgagctggaa cagcggagcc | 480 |
| ctgaccagcg gcgtgcacac cttccccgcc gtgctgcaga gcagcggcct gtacagcctg | 540 |
| agcagcgtgg tgaccgtgcc agcagcaac ttcggcaccc agacctacac ctgcaacgtg | 600 |
| gaccacaagc ccagcaacac caaggtggac aagaccgtgg agcggaagtg ctgcgtggag | 660 |
| tgccccccct gccctgcccc tcctgtggcc ggaccctccg tgttcctgtt cccccccaag | 720 |
| cccaaggaca cctgatgat cagccggacc cccgaggtga cctgcgtggt ggtggacgtg | 780 |
| agccacgagg accccgaggt gcagttcaac tggtacgtgg acggcgtgga ggtgcacaac | 840 |
| gccaagacca gccccggga ggaacagttc aacagcacct ccgggtggt gtccgtgctg | 900 |
| accgtggtgc accaggactg gctgaacggc aaagaataca agtgcaaggt gtccaacaag | 960 |
| ggcctgcctg cccccatcga gaaaaccatc agcaagacaa agggccagcc cagggaaccc | 1020 |
| caggtgtaca ccctgccccc cagccgggag gaaatgacca gaaccaggt gtccctgacc | 1080 |
| tgtctggtga agggcttcta ccccagcgac atcgccgtgg agtgggagag caacggccag | 1140 |
| cccgagaaca actacaagac cacccccccc atgctggaca gcgacggcag cttcttcctg | 1200 |
| tacagcaagc tgacagtgga caagagccgg tggcagcagg gcaacgtgtt cagctgcagc | 1260 |
| gtgatgcacg aggccctgca caaccactac acccagaaga gcctgagcct gtcccccggc | 1320 |
| aaa | 1323 |

```
<210> SEQ ID NO 180
<211> LENGTH: 1323
<212> TYPE: DNA
<213> ORGANISM: Artificial
<220> FEATURE:
<223> OTHER INFORMATION: heavy chain

<400> SEQUENCE: 180
```

| | |
|---|---|
| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggcaat attaatcctg ctactggtca tgctgattat | 180 |
| gctcagaagt ttcagggtcg ggtgaccatg accgtgata ccagcattag caccgcgtat | 240 |
| atggaactga gccgcctgcg tagcgatgat acggccgtgt attattgcgc gcgtggtggt | 300 |
| tggtttgatt attggggcca aggcaccctg gtgacggtta gctcagcttc caccaagggc | 360 |
| ccagcgtgt tcccctggc ccctgcagc agaagcacca gcgagagcac agccgccctg | 420 |
| ggctgcctgg tgaaggacta cttccccgag cccgtgaccg tgagctggaa cagcggagcc | 480 |
| ctgaccagcg gcgtgcacac cttccccgcc gtgctgcaga gcagcggcct gtacagcctg | 540 |
| agcagcgtgg tgaccgtgcc agcagcaac ttcggcaccc agacctacac ctgcaacgtg | 600 |
| gaccacaagc ccagcaacac caaggtggac aagaccgtgg agcggaagtg ctgcgtggag | 660 |
| tgccccccct gccctgcccc tcctgtggcc ggaccctccg tgttcctgtt cccccccaag | 720 |

```
cccaaggaca ccctgatgat cagccggacc cccgaggtga cctgcgtggt ggtggacgtg      780
agccacgagg accccgaggt gcagttcaac tggtacgtgg acggcgtgga ggtgcacaac      840
gccaagacca agccccggga ggaacagttc aacagcacct tccgggtggt gtccgtgctg      900
accgtggtgc accaggactg gctgaacggc aaagaataca agtgcaaggt gtccaacaag      960
ggcctgcctg cccccatcga gaaaaccatc agcaagacaa agggccagcc cagggaaccc     1020
caggtgtaca ccctgccccc cagccgggag gaaatgacca gaaaccaggt gtccctgacc     1080
tgtctggtga agggcttcta ccccagcgac atcgccgtgg agtgggagag caacggccag     1140
cccgagaaca actacaagac caccccccca atgctggaca cgacggcag cttcttcctg      1200 tacagcaagc tgacagtgga caagagccgg tggcagcagg gcaacgtgtt cagctgcagc     1260
gtgatgcacg aggccctgca caaccactac acccagaaga gcctgagcct gtcccccggc     1320
aaa                                                                   1323
```

<210> SEQ ID NO 181
<211> LENGTH: 512
<212> TYPE: PRT
<213> ORGANISM: Homo sapiens

<400> SEQUENCE: 181

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255
```

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Ala Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 182
<211> LENGTH: 116
<212> TYPE: PRT
<213> ORGANISM: Homo sapiens

<400> SEQUENCE: 182

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

```
<210> SEQ ID NO 183
<211> LENGTH: 15
<212> TYPE: PRT
<213> ORGANISM: Homo sapiens

<400> SEQUENCE: 183

Ile Glu Leu Val Lys Lys Gly Ser Trp Leu Asp Asp Phe Asn Ser
1               5                   10                  15

<210> SEQ ID NO 184
<211> LENGTH: 15
<212> TYPE: PRT
<213> ORGANISM: Homo sapiens

<400> SEQUENCE: 184

Val Lys Lys Gly Ser Trp Leu Asp Asp Phe Asn Ser Tyr Asp Arg
1               5                   10                  15

<210> SEQ ID NO 185
<211> LENGTH: 15
<212> TYPE: PRT
<213> ORGANISM: Homo sapiens

<400> SEQUENCE: 185

Gly Ser Trp Leu Asp Asp Phe Asn Ser Tyr Asp Arg Gln Glu Ser
1               5                   10                  15

<210> SEQ ID NO 186
<211> LENGTH: 9
<212> TYPE: PRT
<213> ORGANISM: Homo sapiens

<400> SEQUENCE: 186

Gly Cys Trp Leu Asp Asp Phe Asn Cys
1               5

<210> SEQ ID NO 187
<211> LENGTH: 15
<212> TYPE: PRT
<213> ORGANISM: Homo sapiens

<400> SEQUENCE: 187

Cys Glu Gly Glu Gln Asp Lys Arg Leu His Cys Tyr Ala Ser Trp
1               5                   10                  15

<210> SEQ ID NO 188
<211> LENGTH: 6
<212> TYPE: PRT
<213> ORGANISM: Homo sapiens

<400> SEQUENCE: 188

Trp Leu Asp Asp Phe Asn
1               5

<210> SEQ ID NO 189
<211> LENGTH: 5
<212> TYPE: PRT
<213> ORGANISM: Homo sapiens

<400> SEQUENCE: 189

Glu Gln Asp Lys Arg
1               5
```

```
<210> SEQ ID NO 190
<211> LENGTH: 11
<212> TYPE: PRT
<213> ORGANISM: Homo sapiens

<400> SEQUENCE: 190

Lys Gly Cys Trp Leu Asp Asp Phe Asn Cys Tyr
1               5                   10

<210> SEQ ID NO 191
<211> LENGTH: 13
<212> TYPE: PRT
<213> ORGANISM: Human

<400> SEQUENCE: 191

Cys Ile Tyr Tyr Asn Ala Asn Trp Glu Leu Glu Arg Thr
1               5                   10

<210> SEQ ID NO 192
<211> LENGTH: 11
<212> TYPE: PRT
<213> ORGANISM: Human

<400> SEQUENCE: 192

Tyr Phe Cys Cys Cys Glu Gly Asn Phe Cys Asn
1               5                   10

<210> SEQ ID NO 193
<211> LENGTH: 216
<212> TYPE: PRT
<213> ORGANISM: Artificial Sequence
<220> FEATURE:
<223> OTHER INFORMATION: Light Chain

<400> SEQUENCE: 193

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ser Thr Pro Thr Leu Thr Val Phe Pro Pro Ser Ser Glu
        115                 120                 125

Glu Leu Lys Glu Asn Lys Ala Thr Leu Val Cys Leu Ile Ser Asn Phe
    130                 135                 140

Ser Pro Ser Gly Val Thr Val Ala Trp Lys Ala Asn Gly Thr Pro Ile
145                 150                 155                 160

Thr Gln Gly Val Asp Thr Ser Asn Pro Thr Lys Glu Gly Asn Lys Phe
                165                 170                 175

Met Ala Ser Ser Phe Leu His Leu Thr Ser Asp Gln Trp Arg Ser His
            180                 185                 190

Asn Ser Phe Thr Cys Gln Val Thr His Glu Gly Asp Thr Val Glu Lys
```

-continued

```
                    195                 200                 205

Ser Leu Ser Pro Ala Glu Cys Leu
    210                 215

<210> SEQ ID NO 194
<211> LENGTH: 445
<212> TYPE: PRT
<213> ORGANISM: Artificial
<220> FEATURE:
<223> OTHER INFORMATION: Heavy Chain

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Ala Ala Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
```

```
                    340                 345                 350
Glu Glu Glu Met Thr Lys Lys Gln Val Thr Leu Thr Cys Met Val Thr
            355                 360                 365

Asp Phe Met Pro Glu Asp Ile Tyr Val Glu Trp Thr Asn Asn Gly Lys
        370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
            435                 440                 445
```

ADMINISTRATION OF BIMAGRUMAB FOR IMPROVING MUSCLE MASS AND FUNCTION AFTER HIP FRACTURE SURGERY

TECHNICAL FIELD

This disclosure is in the field of myostatin antagonists, e.g., myostatin binding molecules or Activin receptor IIB (ActRIIB) binding molecules, e.g., an antagonist antibody to ActRIIB, e.g., bimagrumab. In particular, it relates to the improvement or acceleration of recovery after surgical treatment of hip fracture (or hip fracture surgery) and to novel dosing regimens used for this indication, which employ a therapeutically effective amount of an ActRII antagonist, e.g., an Activin receptor II (ActRII) binding molecule, e.g., an anti-Activin receptor II (ActRII) antibody, such as bimagrumab.

BACKGROUND OF THE DISCLOSURE

Myostatin, a member of the transforming growth factor beta (TGF-β) superfamily, is a secreted protein that negatively regulates skeletal muscle mass in animals and humans throughout the lifecycle. Myostatin acts via the activin receptor type II (mainly via ActRIIB) and its proposed signaling is through the SMAD 2/3 pathway, which is involved in the inhibition of protein synthesis, and myocyte differentiation and proliferation. Myostatin inhibition or genetic ablation increases muscle mass and strength (Lee et al 2005, Lee and McPherron 2001, Whittemore et al 2003).

Bimagrumab (BYM338) or is a monoclonal antibody developed to bind competitively to activin receptor type II (ActRII) with greater affinity than myostatin or activin, its natural ligands. Bimagrumab is a fully human antibody (modified IgG1, 234-235-Ala-Ala, λ$_2$) which binds to the ligand binding domain of ActRII, thereby preventing binding and subsequent signaling of its ligands, including myostatin and activin that act as natural inhibitors of skeletal muscle growth. Myostatin, a member of the transforming growth factor beta (TGF-β) superfamily, is a secreted protein that negatively regulates skeletal muscle mass in animals and humans. Myostatin signaling occurs at ActRII and its proposed mechanism of action is through the Smad 2/3 pathway to inhibit protein synthesis and myocyte differentiation and proliferation. Myostatin inhibition or genetic ablation increases muscle mass and strength (Lee et al 2005; Lee and McPherron 2001; Whittemore et al 2003).

Bimagrumab is cross-reactive with human and mouse ActRIIB and effective on human, cynomolgus, mouse and rat skeletal muscle cells. Bimagrumab is formulated for intravenous (i.v.) administration.

Myostatin, ActRIIB Receptor and ActRIIB Receptor Antibodies

Bimagrumab, also known as BYM338, is a human monoclonal antibody developed to bind competitively to activin receptor type II B (ActRIIB) with greater affinity than myostatin, its principal natural ligand. Bimagrumab is disclosed in WO2010/125003, which is incorporated by reference herein in its entirety. Myostatin, a member of the transforming growth factor beta (TGF-β) superfamily, is a secreted protein that negatively regulates skeletal muscle mass in animals and humans, throughout the lifecycle. Myostatin signaling occurs at ActRIIB and its proposed mechanism of action is through the Smad 2/3 pathway to inhibit protein synthesis and myocyte differentiation and proliferation. The absence of myostatin in developing animals and humans results in a hypermuscular phenotype with an increased number and size of muscle fibers. Reducing the level of myostatin postpartum results in the hypertrophy of skeletal muscle due to an increase in the size of existing myofibers. In the adult, myostatin is produced in skeletal muscle and circulated in the blood in part as a latent inactive complex.

Consistent with the role of myostatin as an endogenous inhibitor of skeletal muscle mass, bimagrumab dramatically increased skeletal muscle mass in preclinical murine models of disuse and steroid-induced atrophy and in toxicology studies with healthy cynomolgus monkeys. In addition, the increased mass in mouse and rat resulted in a corresponding increase in muscle strength (force production). Following i.v. and s.c. administration to mice and cynomolgus monkey, bimagrumab showed a consistent IgG1 pharmacokinetic (PK) profile with target mediated drug disposition (TMDD) and was well tolerated.

An analysis of the six dose levels of the first in human, single ascending dose study, suggests that single i.v. doses of 0.1, 0.3, 1, 3, 10 and 30 mg/kg of bimagrumab are safe, well tolerated, and produce a PK profile that is predictable from modeled preclinical data. At four weeks doses of 3-30 mg/kg result in a measurable increase in thigh muscle volume of 2.7-5.2% from baseline over placebo.

Role of Body Composition in the Determination of Mobility and Hip Fracture Risk

It is well established that even in the healthy elderly, declines in muscle strength cannot fully be explained by loss of skeletal muscle mass (Frontera et al 2000, Vandervoort 2002). Further, maintenance or even gains in muscle mass do not necessarily prevent the loss of muscle strength (Goodpaster et al 2006); and the force produced by skeletal muscle per unit of muscle mass decreases with advancing age (Goodpaster et al 2006; Brooks and Faulkner 1994). While these facts do not diminish the importance of maintaining muscle mass during aging, they do underscore that there is more than the loss of muscle tissue to understand and treat to address age-related decline in mobility.

In addition to loss of muscle mass, there is also infiltration of muscle tissue by lipids and other non-contractile components. Emerging evidence suggests that skeletal muscle lipid content directly influences muscle strength and mobility function (Goodpaster et al 2001; Visser et al 2002) as well as the increased risk of future mobility loss in older men and women (Visser et al 2005). Beavers et al (2013) showed that high/increasing inter-muscular adipose tissue (IMAT) area in the thigh, as well as the decreasing total thigh muscle area, is an important predictor of walking speed decline. Baseline thigh IMAT predicts the annual gait speed decline in both men and women. In longitudinal analyses, changes in thigh IMAT and total thigh muscle are the only body-composition measures that predict gait-speed decline in both men and women (FIG. 1).

Age-related adipose infiltration of muscle tissue as well as reduced muscle strength combined with reduced lower extremity performance confer increased risk of outcomes, such as loss of mobility, falls, and skeletal fractures, including hip fracture (Lang et al 2010).

Mechanisms Underlying the Impact of Intermuscular Fat Mass on Skeletal Muscle

Mechanisms underlying the links between increased IMAT and walking speed decline may include the endocrine nature of adipose tissue. Excessive fat accumulation in the muscle may be associated with excessive secretion of proinflammatory cytokines (Fantuzzi et al 2005). Chronic inflammation is associated with lower muscle strength (Visser et al 2002), and predicts disability in older adults (Verghese et al 2011), potentially as a result of impaired muscle-fiber contractility (Pahor & Kritchevsky 1998). Excessive adiposity may also down-regulate the anabolic actions of insulin, testosterone and growth hormone (Chevalier et al 2006, Schaap et al 2005, Waters et al 2008), all of which may contribute to muscle loss and functional decline.

Changes of Body Composition After Hip Fracture

Clinical observations indicate that elderly subjects sustaining a hip fracture and subsequently undergoing major surgery for fracture repair are subject to additional rapid changes in body composition, in a vicious cycle due to exacerbating postoperative mobility limitations (Wehren et al 2005; D'Adamo et al 2014). The immediate or rapidly evolving changes include neurogenic muscle weakness, skeletal muscle loss (disuse atrophy), increase in fat mass and accelerated bone loss (D'Adamo et al 2014, Fox et al 2000, Daguet et al 2011). Importantly, these changes can be apparent from as early as Day 10 and can reach maximum by approximately 2 months after surgery.

Collectively, the acute complication of frailty and fragility—hip fracture—further worsens body composition that contributed to the occurrence of the complication in the first place. In addition, it diminishes the rate and magnitude of postoperative functional recovery, which in turn increases the risk of mobility-related complications (injurious falls, fractures, and related re-hospitalizations). The net result of this vicious cycle is the alarming mortality rate of patients after hip fracture, ranging from 8.4-36% during the first year (Abrahamsen et al 2009).

Early Need for Preventing Postoperative Complications

Importantly, the bulk of complications tend to occur in the first 6 months after surgery increasing the need for measures that can both accelerate and increase the magnitude of general mobility to prevent mobility-related complications, re-hospitalizations and ultimately decrease the fairly high mortality rate in this population.

Unmet Medical Needs

Current standard of care encompassing dietary measures (protein, vitamin D and Ca supplementation), early post-op mobilization and resistance training combined with antiresorptive therapies leave considerable room for optimization. Compliance to rehabilitation is limited and the effect of current pharmacological treatment (bisphosphonates, denosumab, vitamin D) is relatively small and slow in onset.

Requirements to the Ideal Pharmacological Agent

In light of these demands, there is a definite unmet need for a pharmacological agent that can accelerate and boost the efficacy of current standard of care without posing significant safety issues in this frail population with common presence of comorbidities. Thus, the ideal drug candidate would fulfill the following requirements:

A. Can rapidly achieve maximal benefits in terms of reversing the adverse alterations of body composition
B. Can induce muscle mass changes that are clinically meaningful, which can translate into increases in muscle strength and physical performance
C. Can substantially reduce fat infiltration of skeletal muscle thereby improving muscle quality and improvement of muscle strength and mobility
D. No significant safety or tolerability issues limiting the delivery of the intended 6 months treatment Evidence that Bimagrumab has the Best Chances to Deliver on those 3 Requirements Applicant has evidence that of the current approaches to prevent myostatin signaling (anti-myostatin antibody, soluble activin receptor type IIB, and antibody against cell-bound activin type II receptors), activin receptor antagonism is providing the best balance between efficacy and safety (highest benefit/risk ratio), hence being able to induce rapid and substantial muscle growth with concomitant decreases in inter-muscular adipose tissue (i.e. improved muscle quality), which are both contribute directly to improvements of muscle contraction and ultimately mobility.

Preclinical Evidence

ActRII Blockade Induces the Largest Increases in Muscle Mass

The applicant has investigated whether inhibition of other ligands that signal via ActRII were playing a significant role in the hypertrophy induced by bimagrumab by comparing the antibody with an inhibitor that neutralizes only myostatin in the circulation (Lach-Trifilieff 2014). For this purpose a stabilized myostatin propeptide (D76A) was used, which was validated to be a myostatin-specific inhibitor. Both bimagrumab and the myostatin-propeptide were administered weekly for 5 weeks to young SCID mice; bimagrumab was administered at 10 mg/kg, and the myostatin propeptide was administered at 30 mg/kg.

Body weight increased throughout the treatment period, reaching significance upon bimagrumab treatment only (36% versus 15% for myostatin propeptide). The 15% increase induced by the myostatin propeptide is in line with that described in a prior publication (Trendelenburg et al 2009); the ActRII antibody was over 2-fold more efficacious (FIG. 2, left panel). Muscle weights increased significantly in most muscles examined, with more pronounced increases demonstrated with bimagrumab (FIG. 2, middle panel). This greater increase in total muscle mass was further corroborated by analyzing the fiber cross-sectional area distribution, demonstrating that the factors were acting by increasing fiber diameter, as opposed to fiber number (FIG. 2, right panel).

The considerably higher efficacy of activin type II receptor blockade versus neutralization of the circulating myostatin pool clearly demonstrates that there are ligands beyond myostatin that are able to promote muscle loss via activin type IIB receptors.

The third approach to blocking myostatin signaling is by the soluble activin type IIB receptor trap/decoy (ActRIIB-Fc) that can capture all possible ligands of this receptor in the circulation, including myostatin. The efficacy of this approach in terms of induction of muscle growth is probably comparable with that of bimagrumab. Results from a Phase 2 study with the ActRIIB-Fc (ACE-031) on boys with Duchenne muscular dystrophy showed an increase in LBM and attenuation of declines in TMV and the six-minute walk distance (Campbell et al 2012). However, observations of reversible nosebleeds and skin telangiectasias in the healthy volunteer MAD study as well as in the Phase 2 muscular dystrophy study have led to the termination of these trials and the clinical development of this pharmacological approach (Smith and Lin 2013). The fundamental difference of bimagrumab from this latter approach is that it only blocks ligand trafficking through receptors on the target tissue (e.g. muscle) and does not eliminate the opportunity of circulating ligands from reaching their own alternative receptors to exert effects which may be critical for safety (e.g. the signaling of BMPs through ActRIIB located on skeletal muscle will be blocked but BMP can reach and signal through their own BMP receptors, which is not an option with the decoy that prevents action).

Although the activin receptor IIB trap can evoke muscle volume increases comparable with those evoked by blockade of the membrane-bound ActRIIB, and results from a Phase 2 study with the ActRIIB-Fc (ACE-031) in Duchenne muscular dystrophy boys showed an increase in lean body mass and attenuation of declines in thigh muscle volume and six minute walk distance (Campbell et al 2012), the observation of reversible nosebleeds and skin telangiectasias in the healthy volunteer MAD study as well as in the Phase 2 muscular dystrophy study has led to the termination of these trials (Smith and Lin 2013). The fundamental difference between the two approaches is that while the ActRIIB-Fc captures and neutralizes all possible ligands of the receptor in the circulation preventing their binding to other possible target receptors, bimagrumab only blocks ligand trafficking through the ActRIIB on target tissue (e.g. muscle). For example BMPs that bind to ActRIIB may continue to signal through their BMP receptors.

Responsiveness to ActRII Inhibition in Younger and Older Animals

Animal studies demonstrated that a single administration of bimagrumab at 20 mg/kg I.V. significantly increased body weight over 2-3 weeks in both 6 and 21 month old rats pointing to promotion of anabolic muscle actions. This was indeed confirmed by MRI-based evaluation of hind leg muscle volume, which demonstrated that a single dose bimagrumab administration promoted muscle hypertrophy in both 6 and 21 month old rats (FIG. 3).

The hypertrophic action of bimagrumab was prominent 2 weeks after the single administration of the compound, where it reached a 13-15% increase over the control group. Importantly, the maximal response to bimagrumab was similar in 6 and 21 month old rats, demonstrating that old animals are still equally responsive to ActRII inhibition and able to generate the same volume increase in skeletal muscle as young animals when compared in a parallel setting.

Clinical Evidence

Reversal of Disuse Atrophy in Healthy Young Volunteers: Full-Length Leg Casting Model The applicant has evidence that bimagrumab is capable of triggering rapid reversal of disuse-associated muscle loss in young healthy volunteers (average age 24 years) who underwent full-length casting of one leg for 2 weeks. This immobilization (i.e. deactivation of muscles) induced rapid muscle loss of ~5% in the course of 2 weeks. A single i.v. dose of bimagrumab (30 mg/kg) yielded almost full recovery (to −0.8% of pre-casting) of thigh muscle volume within 2 weeks after cast removal, whereas it took seemingly 12 weeks to return to baseline for the group that recovered muscle mass just by returning to normal daily activities (no targeted rehabilitation program). This observation clearly demonstrates the rapid onset of action of ActRII blockade by bimagrumab as reflected by increases in skeletal muscle mass during the early period of remobilization.

Further to the normalization, thigh muscle mass continued to increase from Week 2 to Week 12 after cast removal ending with approximately 5% more volume than the group not receiving bimagrumab (FIG. 4). Hence, all in all a total of ~10% increase in thigh muscle volume to a single intravenous dose of the drug could be evidenced over a 12-week observation period.

Regaining Muscle Mass in Sarcopenic Patients

In a recently completed study on elderly patients with sarcopenia and physical frailty, a single dose of 30 mg/kg intravenous bimagrumab could trigger thigh muscle volume increases, which were comparable with the magnitude of muscle growth seen in the experimental model of disuse atrophy, i.e. >8% increase from baseline in eight weeks (FIG. 5). This increase in mass preceded a significant increase in 6 minute walking distance (6 MWD) in the most mobility limited patients, those who started with 6 MWD<300 m (+76 meters, p=0.02).

Accordingly, bimagrumab was able to induce comparable responses regardless whether it was administered to young subjects with disuse atrophy or elderly subjects who have substantial muscle atrophy due to aging.

Marked Decreases in Intermuscular Adipose Tissue (IMAT)

In a randomized, six treatment, double blind, placebo controlled, single ascending dose design trial on 49 healthy women and men up to 65 years of age single i.v. doses of 0.1, 0.3, 1, 3, 10, and 30 mg/kg were administered in a staggered fashion. In this trial, in addition to safety, tolerability and pharmacokinetics, effects of bimagrumab on thigh muscle volume as well as intermuscular adipose tissue measured by magnetic resonance imaging were also assessed. As shown in FIG. 6, bimagrumab induced dose-dependent decreases in inter-muscular adipose tissue. The effect of 10 and 30 mg/kg was comparable at Week 10 after the drug injection, both exceeding 10% decrease from baseline.

Bimagrumab Treatment is Associated with Significant Improvements in Functional Performance As illustrated by data from patients with sporadic inclusion body myositis, a progressive muscle degenerative disease, the rapid increases in lean body mass (>5% from baseline) induced by a single injection of bimagrumab (30 mg/kg) are able to trigger significant increases in physical performance (FIG. 7). Importantly, improvement of functional following muscle mass increase require a period of lag time possibly reflecting the structural/functional remodeling of skeletal muscle before becoming fully matured and ready to serve increased contractile activities.

Collectively, bimagrumab seems to possess the properties of a capable pharmacological agent that can reverse both age-related changes of body composition as well as the reactive changes (disuse atrophy) following hip fracture surgery. The applicant also has growing evidence arguing that the drug candidate can trigger functional improvement in muscle wasting diseases. Thus, with relatively rapid and pronounced effects on both muscle and IMAT, bimagrumab offers an innovative approach to accelerate recovery after hip fracture.

SUMMARY OF THE DISCLOSURE

Intervening in a patient population having undergone hip fracture surgery is highly innovative and would meet a high unmet medical need. Indeed, there is currently no therapeutic option to improve and/or accelerate recovery from hip fracture surgery. This objective is achieved by the methods and dosing regimen provided within this disclosure.

A first subject matter of the disclosure therefore relates to methods or uses for improving and/or accelerating recovery from hip fracture surgery of compositions comprising a myostatin antagonist, which can be a myostatin binding molecule or an ActRII binding molecule. The myostatin binding molecule can be, e.g., an antagonist antibody to myostatin. The ActRII binding molecule can be, e.g., an antagonist antibody to ActRII, e.g., bimagrumab also known as BYM338.

"Myostatin antagonist" as used herein refers to a molecule capable of antagonizing (e.g., reducing, inhibiting, decreasing, delaying) myostatin function, expression and/or signalling (e.g., by blocking the binding of myostatin to the myostatin receptor, i.e., ActRII). Non-limiting examples of antagonists include myostatin binding molecules and ActRII receptor binding molecules. In some embodiments of the disclosed methods, regimens, kits, processes, uses and compositions, a myostatin antagonist is employed.

By "myostatin binding molecule" is meant any molecule capable of binding to the human myostatin antigen either alone or associated with other molecules. The binding reaction may be shown by standard methods (qualitative assays) including, for example, a binding assay, competition assay or a bioassay for determining the inhibition of myostatin binding to its receptor or any kind of binding assays, with reference to a negative control test in which an antibody of unrelated specificity, but ideally of the same isotype, e.g., an anti-CD25 antibody, is used. Non-limiting examples of myostatin binding molecules include small molecules, myostatin receptor decoys, and antibodies that bind to myostatin as produced by B-cells or hybridomas and chimeric, CDR-grafted or human antibodies or any fragment thereof, e.g., F(ab')$_2$ and Fab fragments, as well as single chain or single domain antibodies. Preferably the myostatin binding molecule antagonizes (e.g., reduces, inhibits, decreases, delays) myostatin function, expression and/or signalling. In some embodiments of the disclosed methods, regimens, kits, processes, uses and compositions, a myostatin binding molecule is employed.

By "ActRII binding molecule" is meant any molecule capable of binding to the human ActRII receptor (ActRIIA and/or ActRIIB) either alone or associated with other molecules. The binding reaction may be shown by standard methods (qualitative assays) including, for example, a binding assay, competition assay or a bioassay for determining the inhibition of ActRII receptor binding to myostatin or any kind of binding assays, with reference to a negative control test in which an antibody of unrelated specificity, but ideally of the same isotype, e.g., an anti-CD25 antibody, is used. Non-limiting examples of ActRII receptor binding molecules include small molecules, myostatin decoys, and antibodies to the ActRII receptor as produced by B-cells or hybridomas and chimeric, CDR-grafted or human antibodies or any fragment thereof, e.g., F(ab')$_2$ and Fab fragments, as well as single chain or single domain antibodies. Preferably the ActRII receptor binding molecule antagonizes (e.g., reduces, inhibits, decreases, delays) myostatin function, expression and/or signalling. In some embodiments of the disclosed methods, regimens, kits, processes, uses and compositions, an ActRIIB receptor binding molecule is employed.

In another embodiment the composition comprises an anti-ActRII antibody which binds to a binding domain consisting of amino acids 19-134 of SEQ ID NO: 181 (SEQ ID NO:182), or to an epitope comprising or consisting of (a) amino acids 78-83 of SEQ ID NO: 181 (WLDDFN—SEQ ID NO:188); (b) amino acids 76-84 of SEQ ID NO:181 (GCWLDDFNC—SEQ ID NO:186); (c) amino acids 75-85 of SEQ ID NO:181 (KGCWLDDFNCY—SEQ ID NO:190); (d) amino acids 52-56 of SEQ ID NO:181 (EQDKR—SEQ ID NO:189); (e) amino acids 49-63 of SEQ ID NO:181 (CEGEQDKRLHCYASW—SEQ ID NO:187); (f) amino acids 29-41 of SEQ ID NO:181 (CIYYNANWELERT—SEQ ID NO:191); (g) amino acids 100-110 of SEQ ID NO:181 (YFCCCEGNFCN—SEQ ID NO:192); or (h) amino acids 78-83 of SEQ ID NO:181 (WLDDFN) and amino acids 52-56 of SEQ ID NO:181 (EQDKR).

In a yet further alternative embodiment, the above mentioned compositions comprise an anti-ActRII antibody which binds ActRIIB with a 10-fold or greater affinity than it binds to ActRIIA.

Additionally, the disclosure relates to composition wherein the anti-ActRIIB antibody comprises a heavy chain variable region CDR1 comprising an amino acid sequence selected from the group consisting of SEQ ID NOs: 1-14; a heavy chain variable region CDR2 comprising an amino acid sequence selected from the group consisting of SEQ ID NOs: 15-28; a heavy chain variable region CDR3 comprising an amino acid sequence selected from the group consisting of SEQ ID NOs: 29-42; a light chain variable region CDR1 comprising an amino acid sequence selected from the group consisting of SEQ ID NOs: 43-56; a light chain variable region CDR2 comprising an amino acid sequence selected from the group consisting of SEQ ID NOs: 57-70; and a light chain variable region CDR3 comprising an amino acid sequence selected from the group consisting of SEQ ID NOs: 71-84.

In certain embodiments, the disclosure provides compositions wherein the anti-ActRII antibody comprises: (a) a heavy chain variable region CDR1 of SEQ ID NO: 1; a heavy chain variable region CDR2 of SEQ ID NO: 15; a heavy chain variable region CDR3 of SEQ ID NO: 29; a light chain variable region CDR1 of SEQ ID NO: 43; a light chain variable region CDR2 of SEQ ID NO: 57; and a light chain variable region CDR3 of SEQ ID NO: 71, (b) a heavy chain variable region CDR1 of SEQ ID NO: 2; a heavy chain variable region CDR2 of SEQ ID NO: 16; a heavy chain variable region CDR3 of SEQ ID NO: 30; a light chain variable region CDR1 of SEQ ID NO: 44; a light chain variable region CDR2 of SEQ ID NO: 58; and a light chain variable region CDR3 of SEQ ID NO: 72, (c) a heavy chain variable region CDR1 of SEQ ID NO: 3; a heavy chain variable region CDR2 of SEQ ID NO: 17; a heavy chain variable region CDR3 of SEQ ID NO: 31; a light chain variable region CDR1 of SEQ ID NO: 45; a light chain variable region CDR2 of SEQ ID NO: 59; and a light chain variable region CDR3 of SEQ ID NO: 73, (d) a heavy chain variable region CDR1 of SEQ ID NO: 4; a heavy chain variable region CDR2 of SEQ ID NO: 18; a heavy chain variable region CDR3 of SEQ ID NO: 32; a light chain variable region CDR1 of SEQ ID NO: 46; a light chain variable region CDR2 of SEQ ID NO: 60; and a light chain variable region CDR3 of SEQ ID NO: 74, (e) a heavy chain variable region CDR1 of SEQ ID NO: 5; a heavy chain variable region CDR2 of SEQ ID NO: 19; a heavy chain variable region CDR3 of SEQ ID NO: 33; a light chain variable region CDR1 of SEQ ID NO: 47; a light chain variable region CDR2 of SEQ ID NO: 61; and a light chain variable region CDR3 of SEQ ID NO: 75, (f) a heavy chain variable region CDR1 of SEQ ID NO: 6; a heavy chain variable region CDR2 of SEQ ID NO: 20; a heavy chain variable region CDR3 of SEQ ID NO: 34; a light chain variable region CDR1 of SEQ ID NO: 48; a light chain variable region CDR2 of SEQ ID NO: 62; and a light chain variable region CDR3 of SEQ ID NO: 76, (g) a heavy chain variable region CDR1 of SEQ ID NO: 7; a heavy chain variable region CDR2 of SEQ ID NO: 21; a heavy chain variable region CDR3 of SEQ ID NO: 35; a light chain variable region CDR1 of SEQ ID NO: 49; a light chain variable region CDR2 of SEQ ID NO: 63; and a light chain variable region CDR3 of SEQ ID NO: 77, (h) a heavy chain variable region CDR1 of SEQ ID NO: 8; a heavy chain variable region CDR2 of SEQ ID NO: 22; a heavy chain variable region CDR3 of SEQ ID NO: 36; a light chain variable region CDR1 of SEQ ID NO: 50 a light chain variable region CDR2 of SEQ ID NO: 64; and a light chain variable region CDR3 of SEQ ID NO: 78, (i) a heavy chain variable region CDR1 of SEQ ID NO: 9; a heavy chain variable region CDR2 of SEQ ID NO: 23; a heavy chain variable region CDR3 of SEQ ID NO: 37; a light chain variable region CDR1 of SEQ ID NO: 51; a light chain variable region CDR2 of SEQ ID NO: 65; and a light chain variable region CDR3 of SEQ ID NO: 79, (j) a heavy chain variable region CDR1 of SEQ ID NO: 10; a heavy chain variable region CDR2 of SEQ ID NO: 24; a heavy chain variable region CDR3 of SEQ ID NO: 38; a light chain variable region CDR1 of SEQ ID NO: 52; a light chain variable region CDR2 of SEQ ID NO: 66; and a light chain variable region CDR3 of SEQ ID NO: 80, (k) a heavy chain variable region CDR1 of SEQ ID NO: 11; a heavy chain variable region CDR2 of SEQ ID NO: 25; a heavy chain variable region CDR3 of SEQ ID NO: 39; a light chain variable region CDR1 of SEQ ID NO: 53; a light chain variable region CDR2 of SEQ ID NO: 67; and a light chain variable region CDR3 of SEQ ID NO: 81, (l) a heavy chain variable region CDR1 of SEQ ID NO: 12; a heavy chain variable region CDR2 of SEQ ID NO: 26; a heavy chain variable region CDR3 of SEQ ID NO: 40; a light chain variable region CDR1 of SEQ ID NO: 54; a light chain variable region CDR2 of SEQ ID NO: 68; and a light chain variable region CDR3 of SEQ ID NO: 82, (m) a heavy chain variable region CDR1 of SEQ ID NO: 13; a heavy chain variable region CDR2 of SEQ ID NO: 27; a heavy chain variable region CDR3 of SEQ ID NO: 41; a light chain variable region CDR1 of SEQ ID NO: 55; a light chain variable region CDR2 of SEQ ID NO: 69; and a light chain variable region CDR3 of SEQ ID NO: 83, or (n) a heavy chain variable region CDR1 of SEQ ID NO: 14; a heavy chain variable region CDR2 of SEQ ID NO: 28; a heavy chain variable region CDR3 of SEQ ID NO: 42; a light chain variable region CDR1 of SEQ ID NO: 56; a light chain variable region CDR2 of SEQ ID NO: 70; and a light chain variable region CDR3 of SEQ ID NO: 84.

In yet another embodiment, the above mentioned anti-ActRII antibody comprises (i) a full length heavy chain amino acid sequence having at least 95% sequence identity to at least one sequence selected from the group consisting of SEQ ID NOs:146-150 and 156-160, (ii) a full length light chain amino acid sequence having at least 95% sequence identity to at least one sequence selected from the group consisting of SEQ ID NOs:141-145 and 151-155 or (iii) (a) the variable heavy chain sequence of SEQ ID NO: 99 and variable light chain sequence of SEQ ID NO: 85; (b) the variable heavy chain sequence of SEQ ID NO: 100 and variable light chain sequence of SEQ ID NO: 86; (c) the variable heavy chain sequence of SEQ ID NO: 101 and variable light chain sequence of SEQ ID NO: 87; (d) the variable heavy chain sequence of SEQ ID NO: 102 and variable light chain sequence of SEQ ID NO: 88; (e) the variable heavy chain sequence of SEQ ID NO: 103 and variable light chain sequence of SEQ ID NO: 89; (f) the variable heavy chain sequence of SEQ ID NO: 104 and variable light chain sequence of SEQ ID NO: 90; (g) the variable heavy chain sequence of SEQ ID NO: 105 and variable light chain sequence of SEQ ID NO: 91; (h) the variable heavy chain sequence of SEQ ID NO: 106 and variable light chain sequence of SEQ ID NO: 92; (i) the variable heavy chain sequence of SEQ ID NO: 107 and variable light chain sequence of SEQ ID NO: 93; (j) the variable heavy chain sequence of SEQ ID NO: 108 and variable light chain sequence of SEQ ID NO: 94; (k) the variable heavy chain sequence of SEQ ID NO: 109 and variable light chain sequence of SEQ ID NO: 95; (l) the variable heavy chain sequence of SEQ ID NO: 110 and variable light chain sequence of SEQ ID NO: 96; (m) the variable heavy chain sequence of SEQ ID NO: 111 and variable light chain sequence of SEQ ID NO: 97; or (n) the variable heavy chain sequence of SEQ ID NO: 112 and variable light chain sequence of SEQ ID NO: 98.

In certain aspects the disclosure relates to the above described compositions, wherein the comprised anti-ActRII antibody comprises (a) the heavy chain sequence of SEQ ID NO: 146 and light chain sequence of SEQ ID NO: 141; (b) the heavy chain sequence of SEQ ID NO: 147 and light chain sequence of SEQ ID NO: 142; (c) the heavy chain sequence of SEQ ID NO: 148 and light chain sequence of SEQ ID NO: 143; (d) the heavy chain sequence of SEQ ID NO: 149 and light chain sequence of SEQ ID NO: 144; (e) the heavy chain sequence of SEQ ID NO: 150 and light chain sequence of SEQ ID NO: 145; (f) the heavy chain sequence of SEQ ID NO: 156 and light chain sequence of SEQ ID NO: 151; (g) the heavy chain sequence of SEQ ID NO: 157 and light chain sequence of SEQ ID NO: 152; (h) the heavy chain sequence of SEQ ID NO: 158 and light chain sequence of SEQ ID NO: 153; (i) the heavy chain sequence of SEQ ID NO: 159 and light chain sequence of SEQ ID NO: 154; or (j) the heavy chain sequence of SEQ ID NO: 160 and light chain sequence of SEQ ID NO: 155.

An additional subject matter of the disclosure relates to composition, wherein (i) the anti-ActRII antibody cross-blocks or is cross blocked by one of the above described antibodies, (ii) has altered effector function through mutation of the Fc region and/or (iii) binds to an epitope recognized by one of the above described antibodies.

In yet another embodiment, the disclosed composition comprises an anti-ActRII antibody encoded by pBW522 (DSM22873) or pBW524 (DSM22874).

As shown by the figure, patients with the smallest increases in muscle mass and largest increases in fat mass are the ones showing the greatest declines in gait/walking speed (adopted from Beavers et al 2013).

Figure 2:
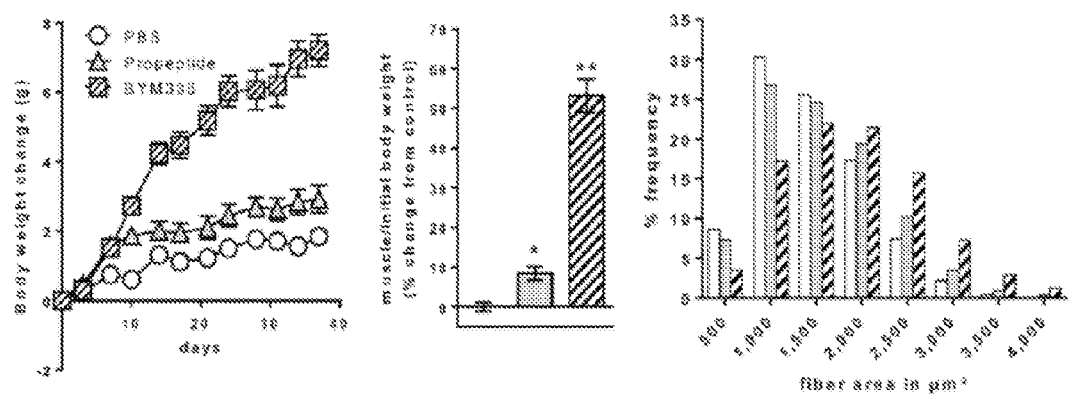

FIG. 2. Comparison of efficacy of anti-ActRII antibody treatment versus pharmacological myostatin inhibition. Treatments were bimagrumab (10 mg/kg; striped bar), myostatin propeptide D76A (30 mg/kg; gray bar), or phosphate buffered saline (white bar). Results are expressed as means±SEMs (n=9 or 10). *, P<0.05 versus the group treated with PBS; **, P0.01 versus the group treated with PBS.

Figure 3:
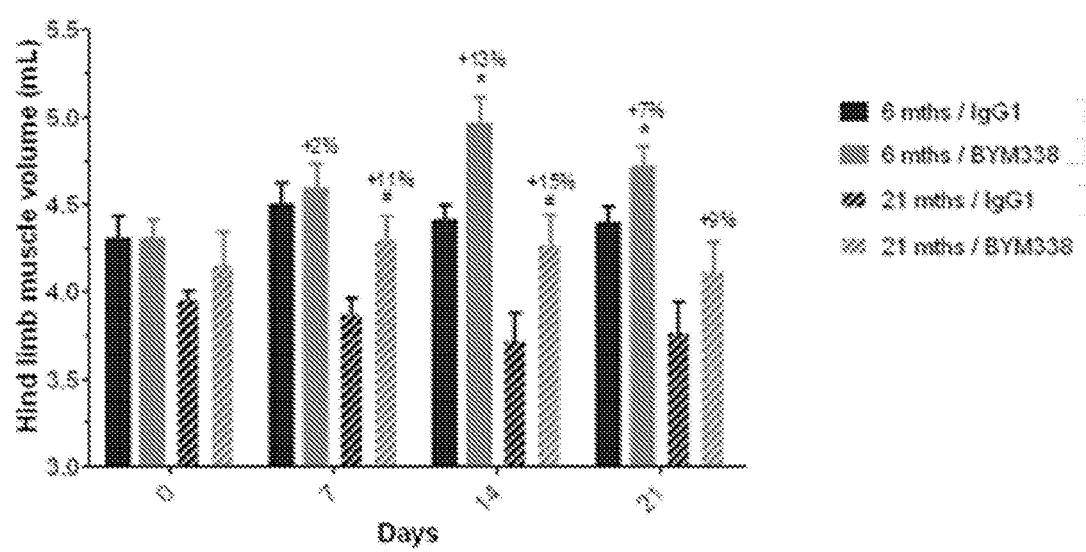

FIG. 3. Hind-leg muscle volume measured by MRI of rats treated for 3 weeks with a single dose of IgG1 or bimagrumab at 20 mg/kg IV.

Figure 4:
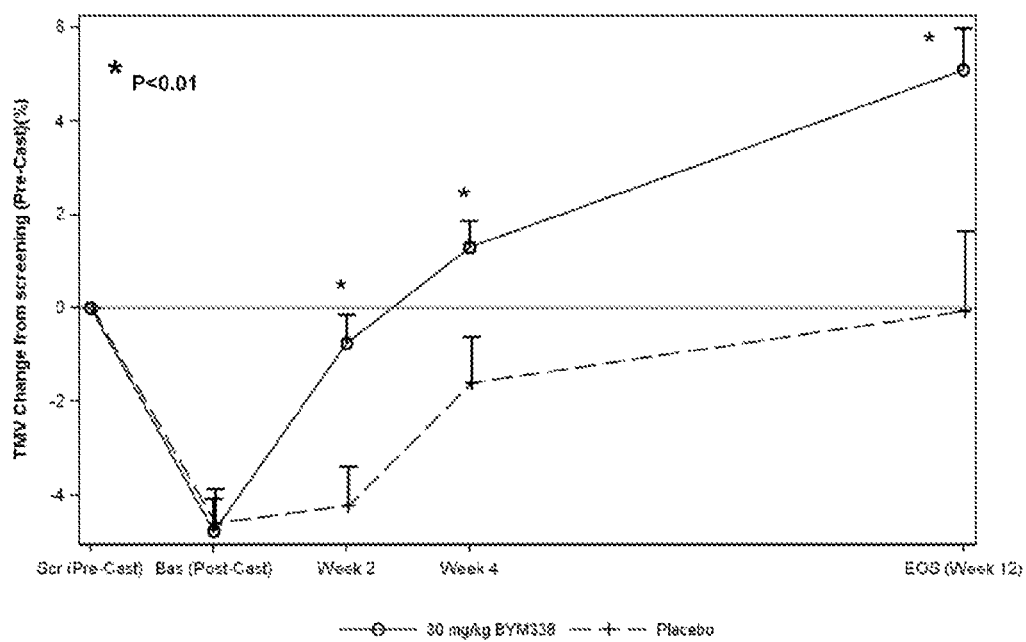

FIG. 4. Changes of thigh muscle volume during 2 weeks of full-leg casting followed by spontaneous recovery with or without a single dose of bimagrumab (30 mg/kg).

Figure 5:
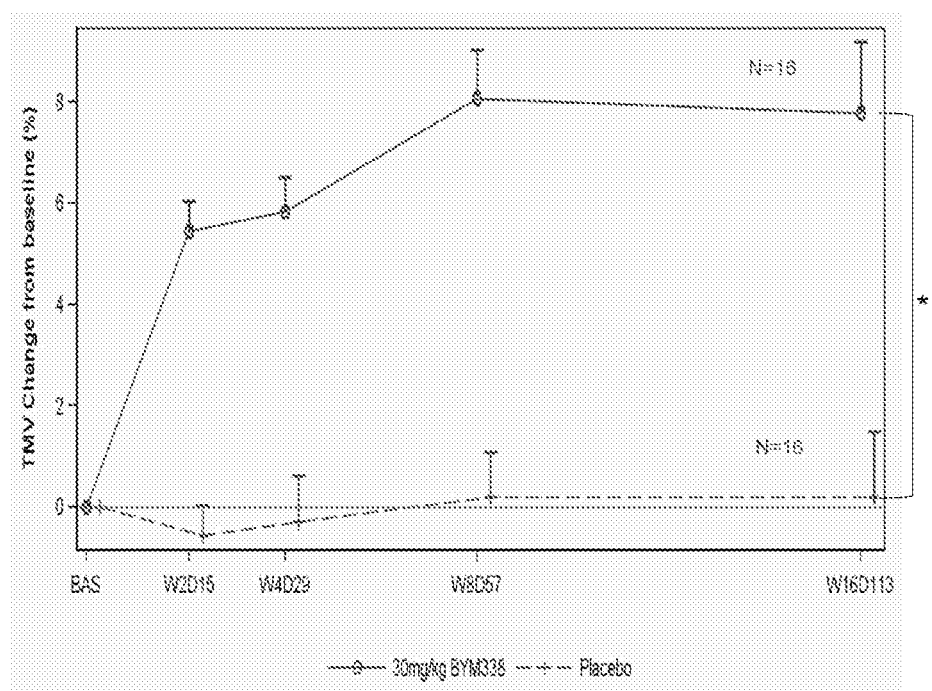

FIG. 5. Changes of thigh muscle volume to one or two doses of bimagrumab (30 mg/kg iv.) in sarcopenic subjects with functional dysmobility (gait speed below 1.0 m/s).

Figure 6:
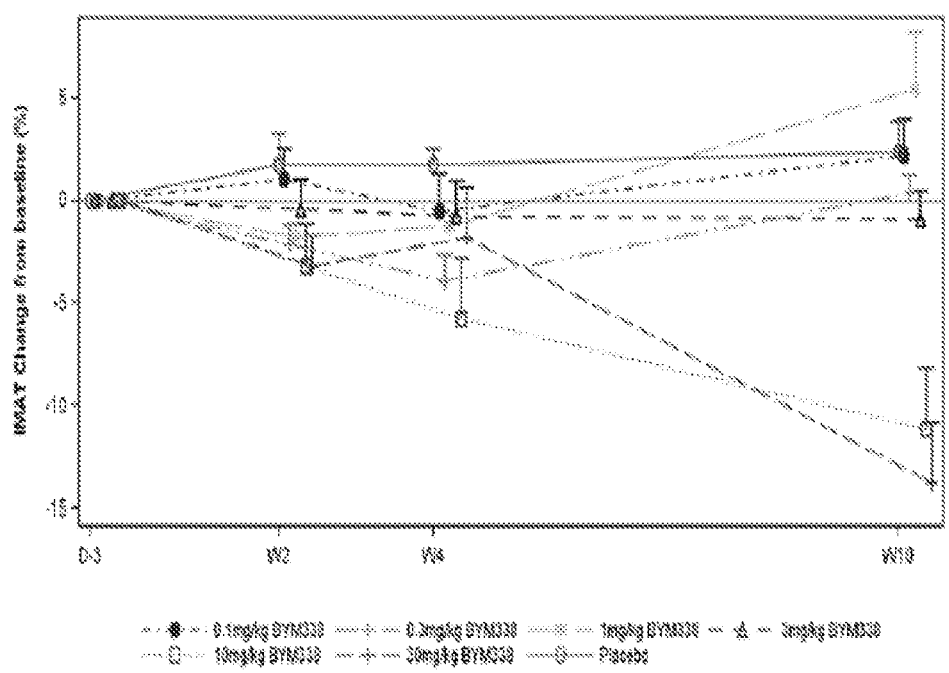

FIG. 6. Changes in inter-muscular adipose tissue from baseline in healthy volunteers receiving a single dose of bimagrumab (0.1, 0.3, 1, 10, 30 mg/kg) results shown are mean (SEM).

Figure 7:
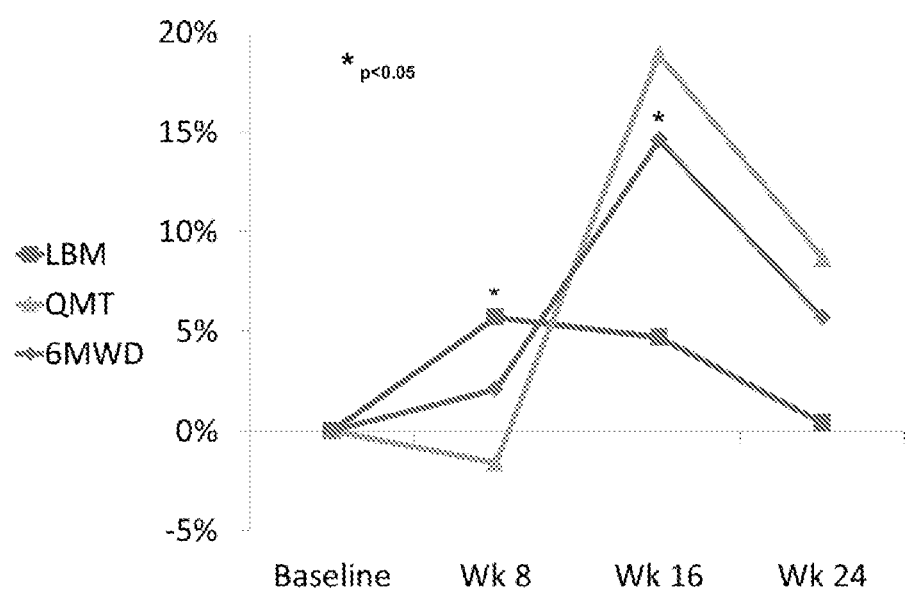

FIG. 7. Bimagrumab-induced changes of lean body mass (LBM), quadriceps strength (QMT) and 6-minute walking distance (6 MWD) from baseline in sporadic inclusion body myositis patients. Note the time-lag between increase in LBM (at Week 8 to Week 16) and significant increases in muscle strength and physical performance starting at Week 16.

Figure 8:
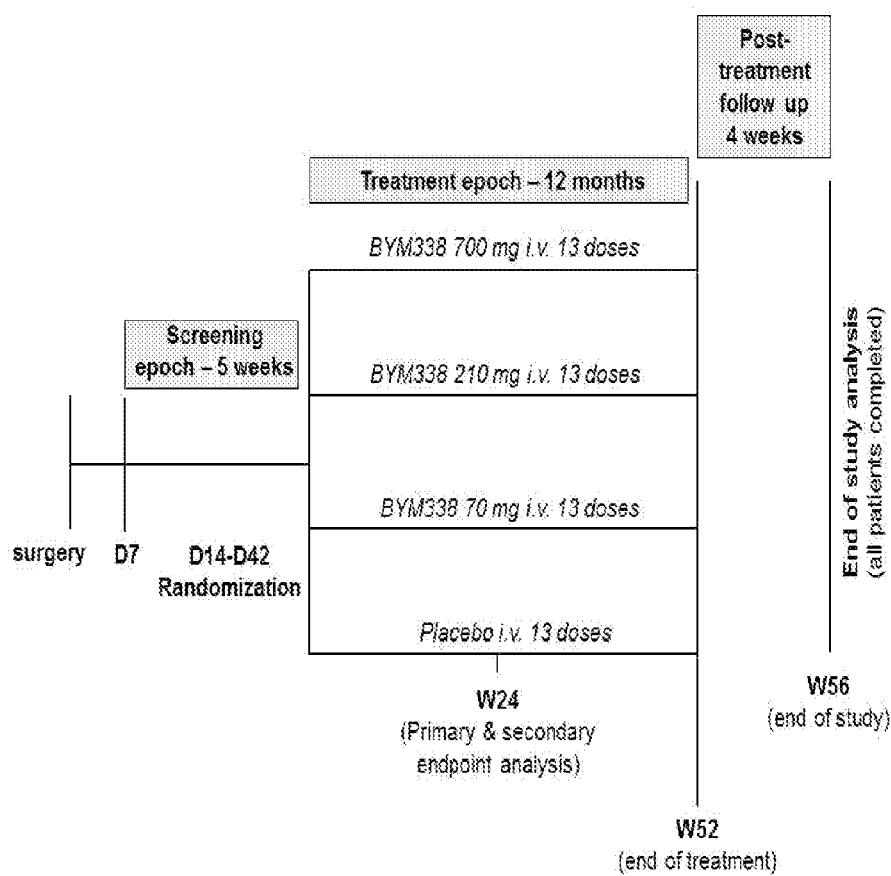

FIG. 8: BYM338D2201 study design.

DEFINITIONS

In order that the present disclosure may be more readily understood, certain terms are first defined. Additional definitions are set forth throughout the detailed description.

The term "comprising" means "including" e.g. a composition "comprising" X may consist exclusively of X or may include something additional e.g. X+Y.

The term "about" in relation to a numerical value x means, for example, x±10%.

The term "disuse atrophy" is another term for muscle atrophy, or muscle wasting. It occurs when a muscle is no longer as active as usual. When muscles are no longer in use, they slowly become weaker. Eventually, they begin to shrink. In some cases, disuse atrophy can be reversed if the muscles become active again.

Disuse atrophy can be caused by immobility, such as an arm being in a cast for a long period of time. It can also occur to some degree if a person stops performing their usual activities, such as walking.

The term "major surgery" is any surgery involving anesthesia and respiratory assistance. In the present context, it implies the significant resection (removal and replacement of a joint) risks of intraoperative or postoperative complications (cardiac or respiratory complication, major bleedings, severe infections). The surgery comprises internal fixation or arthroplasty.

The following exemplifies possible pre-clinical treatment regimes to evaluate possible effects of a treatment with a myostatin antagonist, e.g., myostatin binding molecule or ActRII binding molecule, preferably ActRII binding molecule, more preferably an antagonist antibody to ActRII, e.g., bimagrumab.

The treatment is exemplified by using cynomolgus monkeys, but the described experiments are not limited to monkeys and the skilled person knows how to set up suitable experiments or dosing regimens for other species, in particular for humans: the anti-ActRII antibody, e.g., bimagrumab, can be administered once a week for 3 months to male and female cynomolgus monkeys by intravenous injection. 32 cynomolgus monkeys (16/sex) can be assigned to one of four treatment groups (3 to 5 animals/sex/group) and can be administered intravenous injections of either vehicle or the ActRIIB antibody, e.g., BYM338, at 10, 30, or 100 mg/kg once weekly for 13 weeks (total of 14 doses; doses shall be selected on the basis of muscle hypertrophy activity in monkey).

The terms "ActRIIA" and "ActRIIB" refer to Activin receptors. Activins signal through a heterodimeric complex of receptor serine kinases which include at least two type I (I and IB) and two type II (IIA and IIB, aka ACVR2A and ACVR2B) receptors. These receptors are all transmembrane proteins, composed of a ligand-binding extracellular domain with a cysteine-rich region, a transmembrane domain, and a cytoplasmic domain with predicted serine/threonine specificity. Type I receptors are essential for signaling while type II receptors are required for binding ligands and for expression/recruitment of type I receptors. Type I and II receptors form a stable complex after ligand binding resulting in the phosphorylation of type I receptors by type II receptors. The activin receptor II B (ActRIIB) is a receptor for myostatin. The activin receptor II A (Act RIIA) is also a receptor for mysostatin. The term ActRIIB or Act IIB receptor refers to human ActRIIB as defined in SEQ ID NO: 181 (AAC64515.1, GI:3769443). Research grade polyclonal and monoclonal anti-ActRIIB antibodies are known in the art, such as those made by R&D Systems®, MN, USA. Of course, antibodies could be raised against ActRIIB from other species and used to treat pathological conditions in those species.

The term "immune response" refers to the action of, for example, lymphocytes, antigen presenting cells, phagocytic cells, granulocytes, and soluble macromolecules produced by the above cells or the liver (e.g. antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term "antibody" as referred to herein includes whole antibodies and any antigen binding fragment (i.e. "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g. a portion of ActRIIB). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments, each of which binds to the same antigen, linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g. Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds ActRIIB is substantially free of antibodies that specifically bind antigens other than ActRIIB). An isolated antibody that specifically binds ActRIIB may, however, have cross-reactivity to other antigens, such as ActRIIB molecules from other species. Moreover, an isolated antibody may be substantially free of other cellular material and/or chemicals.

The terms "cross-block", "cross-blocked" and "cross-blocking" are used interchangeably herein to mean the ability of an antibody or other binding agent to interfere with the binding of other antibodies or binding agents to ActRIIB, particularly the ligand binding domain, in a standard competitive binding assay.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g. human germline sequences, or mutated versions of human germline sequences or antibody containing consensus framework sequences derived from human framework sequences analysis, for example, as described in Knappik, et al. (2000. J Mol Biol 296, 57-86). The human antibodies of the disclosure may include amino acid residues not encoded by human sequences (e.g. mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g. a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g. a mouse) that is transgenic or transchromosomal for human immunoglobulin genes or a hybridoma prepared therefrom, antibodies isolated from a host cell transformed to express the human antibody, e.g. from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g. IgM, IgE, IgG such as IgG1 or IgG2) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to ActRIIB polypeptide" is intended to refer to an antibody that binds to human ActRIIB polypeptide with a $K_D$ of a about 100 nM or less, about 10 nM or less, about 1 nM or less. An antibody that "cross-reacts with an antigen other than ActRIIB" is intended to refer to an antibody that binds that antigen with a $K_D$ of about $10 \times 10^{-9}$ M or less, about $5 \times 10^{-9}$ M or less, or about $2 \times 10^{-9}$ M or less. An antibody that "does not cross-react with a particular antigen" is intended to refer to an antibody that binds to that antigen, with a $K_D$ of about $1.5 \times 10^{-8}$ M or greater, or a $K_D$ of about $5$-$10 \times 10^{-8}$ M, or about $1 \times 10^{-7}$ M or greater. In certain embodiments, such antibodies that do not cross-react with the antigen exhibit essentially undetectable binding against these proteins in standard binding assays. $K_D$ may be determined using a biosensor system, such as a Biacore® system, or Solution Equilibrium Titration.

As used herein, the term "antagonist antibody" is intended to refer to an antibody that inhibits ActRIIB induced signaling activity in the presence of myostatin or of other ActRIIB ligands such as activins or GDF-11 and/or to an antibody that inhibits ActRIIA induced signaling activity in the presence of myostatin or of other ActRIIA ligands such as activins or GDF-11. Examples of an assay to detect this include inhibition of myostatin induced signalling (for instance by a Smad dependent reporter gene assay), inhibition of myostatin induced Smad phosphorylation (P-Smad ELISA) and inhibition of myostatin induced inhibition of skeletal muscle cell differentiation (for instance by a creatine kinase assay).

In some embodiments, the antibodies inhibit myostatin induced signalling as measured in a Smad dependent reporter gene assay at an $IC_{50}$ of about 10 nM or less, about 1 nM or less, or about 100 pM or less.

As used herein, an antibody with "no agonistic activity" is intended to refer to an antibody that does not significantly increase ActRIIB mediated signaling activity in the absence of myostatin in a cell-based assay, such as inhibition of myostatin induced signalling (for instance by a Smad dependent reporter gene assay), inhibition of myostatin induced Smad phosphorylation (P-Smad ELISA) and inhibition of myostatin induced inhibition of skeletal muscle cell differentiation (for instance by a creatine kinase assay). Such assays are described in more details in the examples below.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, such as the biosensor system of Biacore®, or Solution Equilibrium Titration (SET) (see Friguet B et al. (1985) J. Immunol Methods; 77(2): 305-319, and Hanel C et al. (2005) Anal Biochem; 339(1): 182-184).

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

As used herein, the term "ADCC" or "antibody dependent cellular cytotoxicity" activity refers to human B cell depleting activity. ADCC activity can be measured by the human B cell depleting assays known in the art.

In order to get a higher avidity probe, a dimeric conjugate (two molecules of an antibody protein coupled to a FACS marker) can be constructed, thus making low affinity interactions (such as with the germline antibody) more readily detected by FACS. In addition, another means to increase the avidity of antigen binding involves generating dimers, trimers or multimers of any of the constructs described herein of the anti-ActRIIB antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in ActRIIB hybrids to create such higher order structures. For example, it is possible to use multimerizing domains such as the trimerizing domain described in WO2004/039841 or pentamerizing domain described in WO98/18943.

As used herein, the term "selectivity" for an antibody refers to an antibody that binds to a certain target polypeptide but not to closely related polypeptides.

As used herein, the term "high affinity" for an antibody refers to an antibody having a $K_D$ of 1 nM or less for a target antigen. As used herein, the term "subject" includes any human or nonhuman animal.

The term "nonhuman animal" includes all vertebrates, e.g. mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of Pichia, a cell of Trichoderma, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells, however optimized expression of these sequences in other eukaryotic cells is also envisioned herein. The amino acid sequences encoded by optimized nucleotide sequences are also referred to as optimized.

DETAILED DESCRIPTION OF THE DISCLOSURE

It has been discovered that antibodies directed to the ActRII receptors, e.g, bimagrumab, can prevent myostatin from binding to the receptor, thus improving or accelerating recovery from hip fracture surgery patients.

Therefore, in one aspect, the disclosure provides a composition comprising a myostatin antagonist, e.g., myostatin binding molecule or ActRII binding molecule, preferably ActRII binding molecule, more preferably an anti-ActRII antibody, e.g, bimagrumab or a functional protein comprising an antigen-binding portion of said antibody for use. In one embodiment, the ActRIIB is human ActRIIB. The polypeptide sequence of human ActRIIB is recited in SEQ ID NO: 181 (AAC64515.1, GI:3769443). In one embodiment, the antibody or functional protein is from a mammal, having an origin such as human or camelid. Thus the antibody comprised in the disclosed composition may be a chimeric, human or a humanized antibody. In a particular embodiment, the anti-ActRIIB antibody comprised in the disclosed composition is characterized as having an antigen-binding region that is specific for the target protein ActRIIB and binds to ActRIIB or a fragment of ActRIIB.

In one embodiment, the antibodies comprised in the disclosed composition are ActRII antagonists with no or low agonistic activity. In another embodiment, the antibody or functional fragment comprised in the disclosed composition binds the target protein ActRII and decreases the binding of myostatin to ActRII to a basal level. In a further aspect of this embodiment, the antibody or functional fragment comprised in the disclosed composition completely prevents myostatin from binding to ActRII. In a further embodiment, the antibody or functional fragment comprised in the disclosed composition inhibits Smad activation. In a further embodiment, the antibody or functional fragment comprised in the disclosed composition inhibits activin receptor type IIB mediated myostatin-induced inhibition of skeletal differentiation via the Smad-dependent pathway.

The binding may be determined by one or more assays that can be used to measure an activity which is either antagonism or agonism by the antibody. Preferably, the assays measure at least one of the effects of the antibody on ActRIIB that include: inhibition of myostatin binding to ActRIIB by ELISA, inhibition of myostatin induced signalling (for instance by a Smad dependent reporter gene assay), inhibition of myostatin induced Smad phosphorylation (P-Smad ELISA) and inhibition of myostatin induced inhibition of skeletal muscle cell differentiation (for instance by a creatine kinase assay).

In one embodiment, the disclosure provides compositions comprising antibodies that specifically bind to the myostatin binding region (i.e. ligand binding domain) of ActRIIB. This ligand binding domain consists of amino acids 19-134 of SEQ ID NO: 181 and has been assigned SEQ ID NO: 182 herein. The ligand biding domain comprises several below described epitopes.

In one embodiment, the antibodies comprised in the disclosed composition bind to ActRIIB with a $K_D$ of about 100 nM or less, about 10 nM or less, about 1 nM or less. Preferably, the antibodies comprised in the disclosed composition bind to ActRIIB with an affinity of 100 pM or less (i.e. about 100 pM, about 50 pM, about 10 pM, about 2 pM, about 1 pM or less). In one embodiment, the antibodies comprised in the disclosed composition bind to ActRIIB with an affinity of between about 1 and about 10 pM.

In one embodiment, the antibodies comprised in the disclosed composition do not cross-react with an ActRIIB related protein, particularly do not cross-react with human ActRIIA (NP_001607.1, GI:4501897). In another embodiment, the antibodies comprised in the disclosed composition cross-react with Act RIIA and bind to ActRIIB with equivalent affinity, or about 1, 2, 3, 4 or 5-fold greater affinity than they bind to ActRIIA, more preferably about 10-fold, still more preferably about 20-, 30-, 40- or 50-fold, still more preferably about 100-fold.

In one embodiment, the antibodies comprised in the disclosed composition bind to ActRIIA with an affinity of 100 pM or more (i.e. about 250 pM, about 500 pM, about 1 nM, about 5 nM or more).

In one embodiment the antibodies comprised in the disclosed composition are of the $IgG_2$ isotype.

In another embodiment, the antibodies comprised in the disclosed composition are of the $IgG_1$ isotype. In a further embodiment, the antibodies comprised in the disclosed composition are of the IgG1 isotype and have an altered effector function through mutation of the Fc region. Said altered effector function may be a reduced ADCC and CDC activity. In one embodiment, said altered effector function is silenced ADCC and CDC activity.

In another related embodiment, the antibodies comprised in the disclosed composition are fully human or humanized IgG1 antibodies with no antibody dependent cellular cytotoxicity (ADCC) activity or CDC activity and bind to a region of ActRIIB consisting of amino acids 19-134 of SEQ ID NO:181.

In another related embodiment, the antibodies comprised in the disclosed composition are fully human or humanized IgG1 antibodies with reduced antibody dependent cellular cytotoxicity (ADCC) activity or CDC activity and bind to a region of ActRIIB consisting of amino acids 19-134 of SEQ ID NO:181.

The present disclosure also relates to compositions comprising human or humanized anti-ActRIIB antibodies for use in accelerating/improving physical recovery in a patient with disuse atrophy triggered by reduced mobility due to a hip fracture and consequent major surgery.

In certain embodiments, the antibodies comprised in the disclosed composition are derived from particular heavy and light chain sequences and/or comprise particular structural features such as CDR regions comprising particular amino acid sequences. The disclosure provides isolated ActRIIB antibodies, methods of making such antibodies, immunoconjugates and multivalent or multispecific molecules comprising such antibodies and pharmaceutical compositions containing the antibodies, immunoconjugates or bispecific molecules.

In alternative embodiments the disclosure relates to the following aspects:
1. A myostatin antagonist for use in accelerating/improving physical recovery in a patient with disuse atrophy triggered by reduced mobility due to a hip fracture and consequent major surgery.
2. A myostatin antagonist for use according to aspect 1, wherein the myostatin antagonist is to be administered after confirmation of successful surgical hip repair and wound healing.
3. A myostatin antagonist for use according to anyone of aspects 1 or 2, wherein the myostatin antagonist is to be administered in a patient able to have weight-bearing walk with or without walking aid and initiate physical rehabilitation.
4. A myostatin antagonist for use according to aspect 1-3, wherein the myostatin antagonist is to be administered starting at 7-42 days or about 1 to 6 weeks, preferably 14-42 days, or about 2 to 6 weeks, up to 8 weeks after surgery.
5. A myostatin antagonist for use according to anyone of aspects claim 1-4, wherein the myostatin antagonist is to be administered to a patient in need thereof at a dose of about 3-10 mg/kg.
6. A myostatin antagonist for use according to aspect 5, wherein said myostatin antagonist is to be administered at a dose of about 3 or about 10 mg/kg body weight.

Alternatively, the myostatin antagonist is to be administered at a dose of about 3, 4, 5, 6, 7, 8, 9 or about 10 mg/kg body weight.

7. A myostatin antagonist for use according to anyone of aspects 1-3, wherein the myostatin antagonist is to be administered to a patient in need thereof at a dose of about 70-700 mg.
8. A myostatin antagonist for use according to aspect 5, wherein said myostatin antagonist is to be administered at a dose of about 210 or about 700 mg.

Alternatively, the myostatin antagonist is to be administered at a dose of about 210, 280, 300, 350, 400, 420, 450, 490, 500, 550, 560, 600, 630 or about 700 mg.

9. A myostatin antagonist for use according to aspect 1-8, wherein said myostatin antagonist is to be administered intravenously.
10. A myostatin antagonist for use according to anyone of aspects 1-9, wherein said myostatin antagonist is to be administered every four weeks.

Alternatively, the myostatin antagonist can be administered every 8 weeks.

11. A myostatin antagonist for use according to anyone of aspects 1-10, wherein said myostatin antagonist is to be administered for at least 3 months.
12. A myostatin antagonist for use according to anyone of aspects 1-11, wherein said myostatin antagonist is to be administered for about 6 months.
13. A myostatin antagonist for use according to anyone of aspects 1-11, wherein said myostatin antagonist is to be administered for up to 12 months.

Preferably the myostatin antagonist is to be administered for at least or up to 3, 4, 5, 6, 7, 8, 9, 10, 11 or 12 months.

14. A myostatin antagonist for use according to anyone of the previous aspects, wherein said myostatin is to be administered to accelerate/improve physical recovery in a patient with disuse atrophy triggered by reduced mobility due to a hip fracture and consequent major surgery implying enhanced muscle growth, increased muscle strength and physical performance, improved self-perceived mobility, accelerated return to independence, and reduced risk of falls and injurious falls.

15. A method of accelerating/improving physical recovery in a patient with disuse atrophy triggered by reduced mobility due to a hip fracture and consequent major surgery for fracture repair comprising administering a myostatin antagonist.

16. A method according to aspect 15, comprising administering a myostatin antagonist after confirmation of successful surgical hip repair and wound healing.

17. A method according to aspect 16, comprising starting administering the myostatin antagonist at about 7-42 days or about 1 to 6 weeks, preferably 14-42 days, or about 2 to 6 weeks, up to 8 weeks after surgery.

18. A method according to anyone of aspects 15-17, comprising starting administering the myostatin antagonist in a patient able to have weight-bearing walk with or without walking aid and initiate physical rehabilitation.

19. A method according according to anyone of aspects 15-18, comprising administering the myostatin antagonist to a patient in need thereof at a dose of about 3-10 mg/kg.

20. A method according to anyone of aspects 15 to 19, comprising administering the myostatin antagonist to a patient in need thereof at a dose of about 3 or about 10 mg/kg body weight.

21. A method according to anyone of aspects 15 to 120, comprising administering the myostatin antagonist intravenously.

22. A method according to anyone of aspects 15 to 21, comprising administering the myostatin antagonist every four weeks.

23. A method according to anyone of aspects 15 to 22, comprising administering the myostatin antagonist or at least 3 months.

24. A method according to anyone of aspects 15 to 23, comprising administering the myostatin antagonist or at least 6 months.

25. A method according to aspect 223, comprising administering the myostatin antagonist for up to 12 months.

26. A method according to anyone of aspects 15-25, wherein accelerating/improving physical recovery in a patient with disuse atrophy triggered by reduced mobility due to a hip fracture and consequent major surgery implies enhanced muscle growth, increased muscle strength and physical performance, improved self-perceived mobility, accelerated return to independence, and reduced risk of falls and injurious falls.

27. A myostatin antagonist for use or a method according to anyone of aspects 1-26, wherein the myostatin antagonist is a myostatin receptor binding molecule.

28. A myostatin antagonist for use or a method according to anyone of aspects 1-27, wherein the myostatin antagonist is an ActRII receptor antagonist.

29. A myostatin antagonist for use or a method according to anyone of aspects 1-28, wherein the myostatin antagonist is an anti-ActRII receptor antibody.

30. A myostatin antagonist for use or a method_according to anyone of aspects 1-29, wherein the anti-ActRII receptor antibody is bimagrumab.

31. A myostatin antagonist for use or a method according to aspect 29, wherein the myostatin antagonist is an anti-ActRII antibody that binds to an epitope of ActRIIB consisting of amino acids 19-134 of SEQ ID NO: 181 (SEQ ID NO: 182).

32. A myostatin antagonist for use or a method according to anyone of aspects 29-31, wherein the anti-ActRII antibody binds to an epitope of ActRIIB comprising or consisting of:
    (a) amino acids 78-83 of SEQ ID NO: 181 (WLDDFN—SEQ ID NO:188);
    (b) amino acids 76-84 of SEQ ID NO: 181 (GCWLDDFNC—SEQ ID NO:186);
    (c) amino acids 75-85 of SEQ ID NO: 181 (KGCWLDDFNCY—SEQ ID NO:190);
    (d) amino acids 52-56 of SEQ ID NO: 181 (EQDKR—SEQ ID NO:189);
    (e) amino acids 49-63 of SEQ ID NO: 181 (CEGEQDKRLHCYASW—SEQ ID NO:187);
    (f) amino acids 29-41 of SEQ ID NO: 181 (CIYYNANWELERT—SEQ ID NO:191);
    (g) amino acids 100-110 of SEQ ID NO: 181 (YFCCCEGNFCN—SEQ ID NO:192); or
    (h) amino acids 78-83 of SEQ ID NO: 181 (WLDDFN) and amino acids 52-56 of SEQ ID NO: 181 (EQDKR).

33. A myostatin antagonist for use according to any of aspects 29-32, wherein the anti-ActRIIB antibody is selected from the group consisting of:
    a) an anti-ActRIIB antibody that binds to an epitope of ActRIIB comprising:
    (a) amino acids 78-83 of SEQ ID NO: 181 (WLDDFN—SEQ ID NO:188);
    (b) amino acids 76-84 of SEQ ID NO: 181 (GCWLDDFNC—SEQ ID NO:186);
    (c) amino acids 75-85 of SEQ ID NO: 181 (KGCWLDDFNCY—SEQ ID NO:190);
    (d) amino acids 52-56 of SEQ ID NO: 181 (EQDKR—SEQ ID NO:189);
    (e) amino acids 49-63 of SEQ ID NO: 181 (CEGEQDKRLHCYASW—SEQ ID NO:187);
    (f) amino acids 29-41 of SEQ ID NO: 181 (CIYYNANWELERT—SEQ ID NO:191);
    (g) amino acids 100-110 of SEQ ID NO: 181 (YFCCCEGNFCN—SEQ ID NO:192); or
    (h) amino acids 78-83 of SEQ ID NO: 181 (WLDDFN) and amino acids 52-56 of SEQ ID NO: 181 (EQDKR).
    and b) an antagonist antibody to ActRIIB that binds to an epitope of ActRIIB comprising amino acids 78-83 of SEQ ID NO: 181 (WLDDFN—SEQ ID NO:188);
    (b) amino acids 76-84 of SEQ ID NO: 181 (GCWLDDFNC—SEQ ID NO:186);
    (c) amino acids 75-85 of SEQ ID NO: 181 (KGCWLDDFNCY—SEQ ID NO:190);
    (d) amino acids 52-56 of SEQ ID NO: 181 (EQDKR—SEQ ID NO:189);
    (e) amino acids 49-63 of SEQ ID NO: 181 (CEGEQDKRLHCYASW—SEQ ID NO:187);
    (f) amino acids 29-41 of SEQ ID NO: 181 (CIYYNANWELERT—SEQ ID NO:191);
    (g) amino acids 100-110 of SEQ ID NO: 181 (YFCCCEGNFCN—SEQ ID NO:192); or
    (h) amino acids 78-83 of SEQ ID NO: 181 (WLDDFN) and amino acids 52-56 of SEQ ID NO: 181 (EQDKR), wherein the antibody has a $K_D$ of about 2 pM.

34. A myostatin antagonist for use or a method according to any of aspects 29-33, wherein the antibody binds to ActRIIB with a 10-fold or greater affinity than it binds to ActRIIA.

35. A myostatin antagonist for use or a method according to anyone of aspects 29-34, wherein the antibody comprises a heavy chain variable region CDR1 comprising an amino acid sequence selected from the group consisting of SEQ ID NOs: 1-14; a heavy chain variable region CDR2 comprising an amino acid sequence selected from the group consisting of SEQ ID NOs: 15-28; a heavy chain variable region CDR3 comprising an amino acid sequence selected from the group consisting of SEQ ID NOs: 29-42; a light chain variable region CDR1 comprising an amino acid sequence selected from the group consisting of SEQ ID NOs: 43-56; a light chain variable region CDR2 comprising an amino acid sequence selected from the group consisting of SEQ ID NOs: 57-70; and a light chain variable region CDR3 comprising an amino acid sequence selected from the group consisting of SEQ ID NOs: 71-84.

36. A myostatin antagonist for use or a method according to any of aspects 29-35 wherein the antibody comprises:
   (a) a heavy chain variable region CDR1 of SEQ ID NO: 1; a heavy chain variable region CDR2 of SEQ ID NO: 15; a heavy chain variable region CDR3 of SEQ ID NO: 29; a light chain variable region CDR1 of SEQ ID NO: 43; a light chain variable region CDR2 of SEQ ID NO: 57; and a light chain variable region CDR3 of SEQ ID NO: 71,
   (b) a heavy chain variable region CDR1 of SEQ ID NO: 2; a heavy chain variable region CDR2 of SEQ ID NO: 16; a heavy chain variable region CDR3 of SEQ ID NO: 30; a light chain variable region CDR1 of SEQ ID NO: 44; a light chain variable region CDR2 of SEQ ID NO: 58; and a light chain variable region CDR3 of SEQ ID NO: 72,
   (c) a heavy chain variable region CDR1 of SEQ ID NO: 3; a heavy chain variable region CDR2 of SEQ ID NO: 17; a heavy chain variable region CDR3 of SEQ ID NO: 31; a light chain variable region CDR1 of SEQ ID NO: 45; a light chain variable region CDR2 of SEQ ID NO: 59; and a light chain variable region CDR3 of SEQ ID NO: 73,
   (d) a heavy chain variable region CDR1 of SEQ ID NO: 4; a heavy chain variable region CDR2 of SEQ ID NO: 18; a heavy chain variable region CDR3 of SEQ ID NO: 32; a light chain variable region CDR1 of SEQ ID NO: 46; a light chain variable region CDR2 of SEQ ID NO: 60; and a light chain variable region CDR3 of SEQ ID NO: 74,
   (e) a heavy chain variable region CDR1 of SEQ ID NO: 5; a heavy chain variable region CDR2 of SEQ ID NO: 19; a heavy chain variable region CDR3 of SEQ ID NO: 33; a light chain variable region CDR1 of SEQ ID NO: 47; a light chain variable region CDR2 of SEQ ID NO: 61; and a light chain variable region CDR3 of SEQ ID NO: 75,
   (f) a heavy chain variable region CDR1 of SEQ ID NO: 6; a heavy chain variable region CDR2 of SEQ ID NO: 20; a heavy chain variable region CDR3 of SEQ ID NO: 34; a light chain variable region CDR1 of SEQ ID NO: 48; a light chain variable region CDR2 of SEQ ID NO: 62; and a light chain variable region CDR3 of SEQ ID NO: 76,
   (g) a heavy chain variable region CDR1 of SEQ ID NO: 7; a heavy chain variable region CDR2 of SEQ ID NO: 21; a heavy chain variable region CDR3 of SEQ ID NO: 35; a light chain variable region CDR1 of SEQ ID NO: 49; a light chain variable region CDR2 of SEQ ID NO: 63; and a light chain variable region CDR3 of SEQ ID NO: 77,
   (h) a heavy chain variable region CDR1 of SEQ ID NO: 8; a heavy chain variable region CDR2 of SEQ ID NO: 22; a heavy chain variable region CDR3 of SEQ ID NO: 36; a light chain variable region CDR1 of SEQ ID NO: 50 a light chain variable region CDR2 of SEQ ID NO: 64; and a light chain variable region CDR3 of SEQ ID NO: 78,
   (i) a heavy chain variable region CDR1 of SEQ ID NO: 9; a heavy chain variable region CDR2 of SEQ ID NO: 23; a heavy chain variable region CDR3 of SEQ ID NO: 37; a light chain variable region CDR1 of SEQ ID NO: 51; a light chain variable region CDR2 of SEQ ID NO: 65; and a light chain variable region CDR3 of SEQ ID NO: 79,
   (j) a heavy chain variable region CDR1 of SEQ ID NO: 10; a heavy chain variable region CDR2 of SEQ ID NO: 24; a heavy chain variable region CDR3 of SEQ ID NO: 38; a light chain variable region CDR1 of SEQ ID NO: 52; a light chain variable region CDR2 of SEQ ID NO: 66; and a light chain variable region CDR3 of SEQ ID NO: 80,
   (k) a heavy chain variable region CDR1 of SEQ ID NO: 11; a heavy chain variable region CDR2 of SEQ ID NO: 25; a heavy chain variable region CDR3 of SEQ ID NO: 39; a light chain variable region CDR1 of SEQ ID NO: 53; a light chain variable region CDR2 of SEQ ID NO: 67; and a light chain variable region CDR3 of SEQ ID
   (l) a heavy chain variable region CDR1 of SEQ ID NO: 12; a heavy chain variable region CDR2 of SEQ ID NO: 26; a heavy chain variable region CDR3 of SEQ ID NO: 40; a light chain variable region CDR1 of SEQ ID NO: 54; a light chain variable region CDR2 of SEQ ID NO: 68; and a light chain variable region CDR3 of SEQ ID NO: 82,
   (m) a heavy chain variable region CDR1 of SEQ ID NO: 13; a heavy chain variable region CDR2 of SEQ ID NO: 27; a heavy chain variable region CDR3 of SEQ ID NO: 41; a light chain variable region CDR1 of SEQ ID NO: 55; a light chain variable region CDR2 of SEQ ID NO: 69; and a light chain variable region CDR3 of SEQ ID NO: 83, or
   (n) a heavy chain variable region CDR1 of SEQ ID NO: 14; a heavy chain variable region CDR2 of SEQ ID NO: 28; a heavy chain variable region CDR3 of SEQ ID NO: 42; a light chain variable region CDR1 of SEQ ID NO: 56; a light chain variable region CDR2 of SEQ ID NO: 70; and a light chain variable region CDR3 of SEQ ID NO: 84.

37. A myostatin antagonist for use or a method according to according to any of aspects 29-36, wherein the antibody comprises a full length heavy chain amino acid sequence having at least 95% sequence identity to at least one sequence selected from the group consisting of SEQ ID NOs: 146-150 and 156-160.

38. A myostatin antagonist for use or a method according to any of aspects 29-37, wherein the antibody comprises a full length light chain amino acid sequence having at least 95% sequence identity to at least one sequence selected from the group consisting of SEQ ID NOs: 141-145 and 151-155.

39. A myostatin antagonist for use or a method according to any of aspects 29-38, wherein the antibody comprises:
   (a) the variable heavy chain sequence of SEQ ID NO: 99 and variable light chain sequence of SEQ ID NO: 85;
   (b) the variable heavy chain sequence of SEQ ID NO: 100 and variable light chain sequence of SEQ ID NO: 86;
   (c) the variable heavy chain sequence of SEQ ID NO: 101 and variable light chain sequence of SEQ ID NO: 87;
   (d) the variable heavy chain sequence of SEQ ID NO: 102 and variable light chain sequence of SEQ ID NO: 88;
   (e) the variable heavy chain sequence of SEQ ID NO: 103 and variable light chain sequence of SEQ ID NO: 89;
   (f) the variable heavy chain sequence of SEQ ID NO: 104 and variable light chain sequence of SEQ ID NO: 90;
   (g) the variable heavy chain sequence of SEQ ID NO: 105 and variable light chain sequence of SEQ ID NO: 91;
   (h) the variable heavy chain sequence of SEQ ID NO: 106 and variable light chain sequence of SEQ ID NO: 92;
   (i) the variable heavy chain sequence of SEQ ID NO: 107 and variable light chain sequence of SEQ ID NO: 93;
   (j) the variable heavy chain sequence of SEQ ID NO: 108 and variable light chain sequence of SEQ ID NO: 94;
   (k) the variable heavy chain sequence of SEQ ID NO: 109 and variable light chain sequence of SEQ ID NO: 95;
   (l) the variable heavy chain sequence of SEQ ID NO: 110 and variable light chain sequence of SEQ ID NO: 96;
   (m) the variable heavy chain sequence of SEQ ID NO: 111 and variable light chain sequence of SEQ ID NO: 97; or
   (n) the variable heavy chain sequence of SEQ ID NO: 112 and variable light chain sequence of SEQ ID NO: 98.

40. A myostatin antagonist for use or a method according to any of aspects 29-39, wherein the antibody comprises:
   (a) the heavy chain sequence of SEQ ID NO: 146 and light chain sequence of SEQ ID NO: 141;
   (b) the heavy chain sequence of SEQ ID NO: 147 and light chain sequence of SEQ ID NO: 142;
   (c) the heavy chain sequence of SEQ ID NO: 148 and light chain sequence of SEQ ID NO: 143;
   (d) the heavy chain sequence of SEQ ID NO: 149 and light chain sequence of SEQ ID NO: 144;
   (e) the heavy chain sequence of SEQ ID NO: 150 and light chain sequence of SEQ ID NO: 145;
   (f) the heavy chain sequence of SEQ ID NO: 156 and light chain sequence of SEQ ID NO: 151;
   (g) the heavy chain sequence of SEQ ID NO: 157 and light chain sequence of SEQ ID NO: 152;
   (h) the heavy chain sequence of SEQ ID NO: 158 and light chain sequence of SEQ ID NO: 153;
   (i) the heavy chain sequence of SEQ ID NO: 159 and light chain sequence of SEQ ID NO: 154; or
   (j) the heavy chain sequence of SEQ ID NO: 160 and light chain sequence of SEQ ID NO: 155.

41. A myostatin antagonist for use according to according to any of aspects 29-40, wherein the antibody comprised in said composition cross-blocks or is cross blocked by at least one antibody of aspect 36 from binding to ActRIIB.

42. A myostatin antagonist for use according to according to any of aspects 29-41, wherein the antibody comprised in said composition has altered effector function through mutation of the Fc region.

43. A myostatin antagonist for use according to according to any of aspects 29-42, wherein the antibody comprised in said composition binds to an epitope recognised by an antibody listed in aspects 39-40.

44. A myostatin antagonist for use according to any of aspects 29-43, wherein the antibody is encoded by pBW522 (DSM22873) or pBW524 (DSM22874).

45. Bimagrumab for use in accelerating/improving physical recovery in a patient with disuse atrophy triggered by reduced mobility due to a hip fracture and consequent major surgery, wherein bimagrumab is to be administered intraveneously at a dose of about 3-10 mg/kg body weight every four weeks.

46. Bimagrumab for use in accelerating/improving physical recovery in a patient with disuse atrophy triggered by reduced mobility due to a hip fracture and consequent major surgery, wherein bimagrumab is to be administered intravenously at a dose of about 3 mg/kg body weight every four weeks.

47. Bimagrumab for use in accelerating/improving physical recovery in a patient with disuse atrophy triggered by reduced mobility due to a hip fracture and consequent major surgery, wherein bimagrumab is to be administered intravenously at a dose of about 10 mg/kg body weight every four weeks.

48. A composition comprising 150 mg/ml of bimagrumab for use in a method of accelerating/improving physical recovery in a patient with disuse atrophy triggered by reduced mobility due to a hip fracture and consequent major surgery.

49. A unitary dosage form comprising 150 mg/ml of bimagrumab.

In further embodiments the unitary dosage form, i.e., a vial, comprises 100-200 mg/ml of bimagrumab, preferably 100, 105, 110, 115, 120, 125, 130, 135, 140, 145, 150, 155, 160, 165, 170, 175, 180, 185, 190, 195, 200 mg/ml of bimagrumab.

50. An infusion bag comprising an appropriate amount of bimagrumab from one or more vials diluted with a solution.

The solution is preferably a dextrose solution.

In some further embodiments, the myostatin antagonist, preferably the AcRII antagonist or anti-ActRII antibody such as bimagrumab is to be administered at a dose of about 1, 2, 3, 4, 5, 5, 6, 7, 8, 9, 10 mg/kg body weight.

Disclosed herein are myostatin antagonists for the manufacture of a medicament for accelerating/improving physical recovery in a patient with disuse atrophy triggered by reduced mobility due to a hip fracture and consequent major surgery.

In further embodiments all the aspects disclosed herein can be used in combination one with any of the other.

Various aspects of the disclosure are described in further detail in the following subsections. Standard assays to evaluate the binding ability of the antibodies toward ActRII of various species are known in the art, including for example, ELISAs, western blots and RIAs. Suitable assays are described in detail in the Examples. The binding affinity of the antibodies also can be assessed by standard assays known in the art, such as by Biacore analysis or Solution Equilibrium Titration. Surface plasmon resonance based techniques such as Biacore can determine the binding kinetics which allows the calculation of the binding affinity. Assays to evaluate the effects of the antibodies on functional properties of ActRIIB (e.g. receptor binding, preventing or inducing human B cell proliferation or IgG production) are described in further detail in the Examples.

Accordingly, an antibody that "inhibits" one or more of these ActRII functional properties (e.g. biochemical, immunochemical, cellular, physiological or other biological activities, or the like) as determined according to methodologies known to the art and described herein, will be understood to relate to a statistically significant decrease in the particular activity relative to that seen in the absence of the antibody (e.g. or when a control antibody of irrelevant specificity is present). An antibody that inhibits ActRII activity effects such a statistically significant decrease by at least 10% of the measured parameter, by at least 50%, 80% or 90%, and in certain embodiments an antibody of the disclosure may inhibit greater than 95%, 98% or 99% of ActRIIB functional activity.

The ability or extent to which an antibody or other binding agent is able to interfere with the binding of another antibody or binding molecule to ActRII, and therefore whether it can be said to cross-block according to the disclosure, can be determined using standard competition binding assays. One suitable assay involves the use of the Biacore technology (e.g. by using a BIAcore instrument (Biacore, Uppsala, Sweden)), which can measure the extent of interactions using surface plasmon resonance technology. Another assay for measuring cross-blocking uses an ELISA-based approach. A further assay uses FACS analysis, wherein competition of various antibodies for binding to ActRIIB expressing cells is tested (such as described in the Examples).

According to the disclosure, a cross-blocking antibody or other binding agent according to the disclosure binds to ActRII in the described BIAcore cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination.

An antibody is defined as cross-blocking an anti-ActRIIB antibody of the disclosure in an ELISA assay, if the test antibody is able to cause a reduction of anti-ActRII antibody binding to ActRIIB of between 60% and 100%, specifically between 70% and 100%, and more specifically between 80% and 100%, when compared to the positive control wells (i.e. the same anti-ActRIIB antibody and ActRIIB, but no "test" cross-blocking antibody). Examples of cross blocking antibodies as cited herein are MOR08159 and MOR08213 (disclosed in WO2010/125003). Thus, the disclosure provides compositions comprising antibodies that cross block MOR08159 or MOR08213 for binding to ActRIIB.

Recombinant Antibodies

Antibodies, e.g., antagonist antibodies to ActRII, such as bimagrumab, comprised in the compositions used within this disclosure include the human recombinant antibodies, isolated and structurally characterized, as described in the Examples. The $V_H$ amino acid sequences of antibodies comprised in the inventive compositions are shown in SEQ ID NOs: 99-112. The $V_L$ amino acid sequences of antibodies comprised in the inventive compositions are shown in SEQ ID NOs: 85-98 respectively. Examples of preferred full length heavy chain amino acid sequences of antibodies comprised in the inventive compositions are shown in SEQ ID NOs: 146-150 and 156-160. Examples of preferred full length light chain amino acid sequences of antibodies comprised in the inventive compositions are shown in SEQ ID NOs: 141-145 and 151-155 respectively. Other antibodies comprised in the inventive compositions include amino acids that have been mutated by amino acid deletion, insertion or substitution, yet have at least 60, 70, 80, 90, 95, 97 or 99 percent identity in the CDR regions with the CDR regions depicted in the sequences described above. In some embodiments, it includes mutant amino acid sequences wherein no more than 1, 2, 3, 4 or 5 amino acids have been mutated by amino acid deletion, insertion or substitution in the CDR regions when compared with the CDR regions depicted in the sequence described above.

Further, variable heavy chain parental nucleotide sequences are shown in SEQ ID NOs: 127-140. Variable light chain parental nucleotide sequences are shown in SEQ ID NOs: 113-126. Full length light chain nucleotide sequences optimized for expression in a mammalian cell are shown in SEQ ID NOs: 161-165 and 171-175. Full length heavy chain nucleotide sequences optimized for expression in a mammalian cell are shown in SEQ ID NOs: 166-170 and 176-180. Other antibodies comprised in the inventive compositions include amino acids or are encoded by nucleic acids that have been mutated, yet have at least 60 or more (i.e. 80, 90, 95, 97, 99 or more) percent identity to the sequences described above. In some embodiments, it includes mutant amino acid sequences wherein no more than 1, 2, 3, 4 or 5 amino acids have been mutated by amino acid deletion, insertion or substitution in the variable regions when compared with the variable regions depicted in the sequence described above.

Since each of these antibodies binds the same epitope and are progenies from the same parental antibody, the $V_H$, $V_L$, full length light chain, and full length heavy chain sequences (nucleotide sequences and amino acid sequences) can be "mixed and matched" to create other anti-ActRIIB binding molecules of the disclosure. ActRIIB binding of such "mixed and matched" antibodies can be tested using the binding assays described above and in the Examples (e.g. ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the disclosure provides compositions comprising a recombinant anti-ActRII antibody or antigen binding region thereof having: a heavy chain variable region comprising an amino acid sequence selected from the group consisting of SEQ ID NOs: 99-112; and a light chain variable region comprising an amino acid sequence selected from the group consisting of SEQ ID NOs: 85-98.

In another aspect, the disclosure provides compositions comprising:

(i) an isolated recombinant anti-ActRII antibody having: a full length heavy chain comprising an amino acid sequence selected from the group consisting of SEQ ID NOs:99-112; and a full length light chain comprising an amino acid sequence selected from the group consisting of SEQ ID NOs:85-98, or (ii) a functional protein comprising an antigen binding portion thereof.

In another aspect, the disclosure provides compositions comprising:

(i) an isolated recombinant anti-ActRII antibody having a full length heavy chain encoded by a nucleotide sequence that has been optimized for expression in the cell of a mammalian selected from the group consisting of SEQ ID NOs:127-140, and a full length light chain encoded by a nucleotide sequence that has been optimized for expression in the cell of a mammalian selected from the group consisting of SEQ ID NOs:113-126, or (ii) a functional protein comprising an antigen binding portion thereof.

Examples of amino acid sequences of the $V_H$ CDR1s of the antibodies comprised in the inventive compositions are shown in SEQ ID NOs: 1-14. The amino acid sequences of the $V_H$ CDR2s of the antibodies are shown in SEQ ID NOs: 15-28. The amino acid sequences of the $V_H$ CDR3s of the antibodies are shown in SEQ ID NOs: 29-42. The amino acid sequences of the $V_L$ CDR1s of the antibodies are shown in SEQ ID NOs: 43-56. The amino acid sequences of the $V_L$ CDR2s of the antibodies are shown in SEQ ID NOs: 57-70. The amino acid sequences of the $V_L$ CDR3s of the antibodies are shown in SEQ ID NOs: 71-84. The CDR regions are delineated using the Kabat system (Kabat, E. A., et al., 1991 Sequences of Proteins of Immunological Interest, Fifth Edition, U.S. Department of Health and Human Services, NIH Publication No. 91-3242). An alternative method of determining CDR regions uses the method devised by Chothia (Chothia et al. 1989, Nature, 342:877-883). The Chothia definition is based on the location of the structural loop regions. However, due to changes in the numbering system used by Chothia (see e.g. http://www.biochem.u-cl.ac.uk/~martin/abs/GeneralInfo.html and http://www.bio-inf.org.uk/abs/), this system is now less commonly used. Other systems for defining CDRs exist and are also mentioned in these two websites.

Given that each of these antibodies can bind to ActRII and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e. CDRs from different antibodies can be mixed and matched, each antibody containing a $V_H$ CDR1, 2 and 3 and a $V_L$ CDR1, 2 and 3 create other anti-ActRII binding molecules of the disclosure. ActRIIB binding of such "mixed and matched" antibodies can be tested using the binding assays described above and in the Examples (e.g. ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies.

Anti-ActRII antibody comprised in the disclosed compositions, or antigen binding region thereof has: a heavy chain variable region CDR1 comprising an amino acid sequence selected from the group consisting of SEQ ID NOs: 1-14; a heavy chain variable region CDR2 comprising an amino acid sequence selected from the group consisting of SEQ ID NOs: 15-28; a heavy chain variable region CDR3 comprising an amino acid sequence selected from the group consisting of SEQ ID NOs: 29-42; a light chain variable region CDR1 comprising an amino acid sequence selected from the group consisting of SEQ ID NOs: 43-56; a light chain variable region CDR2 comprising an amino acid sequence selected from the group consisting of SEQ ID NOs: 57-70; and a light chain variable region CDR3 comprising an amino acid sequence selected from the group consisting of SEQ ID NOs: 71-84.

In one embodiment, the antibody comprised in the inventive composition comprises: a heavy chain variable region CDR1 of SEQ ID NO: 1; a heavy chain variable region CDR2 of SEQ ID NO: 15; a heavy chain variable region CDR3 of SEQ ID NO: 29; a light chain variable region CDR1 of SEQ ID NO: 43; a light chain variable region CDR2 of SEQ ID NO: 57; and a light chain variable region CDR3 of SEQ ID NO: 71.

In one embodiment, the antibody comprised in the inventive composition comprises: a heavy chain variable region CDR1 of SEQ ID NO: 2 a heavy chain variable region CDR2 of SEQ ID NO: 16; a heavy chain variable region CDR3 of SEQ ID NO: 30; a light chain variable region CDR1 of SEQ ID NO: 44; a light chain variable region CDR2 of SEQ ID NO: 58; and a light chain variable region CDR3 of SEQ ID NO: 72.

In one embodiment, the antibody comprised in the inventive composition comprises: a heavy chain variable region CDR1 of SEQ ID NO: 3; a heavy chain variable region CDR2 of SEQ ID NO: 17; a heavy chain variable region CDR3 of SEQ ID NO: 31; a light chain variable region CDR1 of SEQ ID NO: 45; a light chain variable region CDR2 of SEQ ID NO: 59; and a light chain variable region CDR3 of SEQ ID NO: 73.

In one embodiment, the antibody comprised in the inventive composition comprises: a heavy chain variable region CDR1 of SEQ ID NO: 4; a heavy chain variable region CDR2 of SEQ ID NO: 18; a heavy chain variable region CDR3 of SEQ ID NO: 32; a light chain variable region CDR1 of SEQ ID NO: 46; a light chain variable region CDR2 of SEQ ID NO: 60; and a light chain variable region CDR3 of SEQ ID NO: 74.

In one embodiment, the antibody comprised in the inventive composition comprises: a heavy chain variable region CDR1 of SEQ ID NO: 5; a heavy chain variable region CDR2 of SEQ ID NO: 19; a heavy chain variable region CDR3 of SEQ ID NO: 33; a light chain variable region CDR1 of SEQ ID NO: 47; a light chain variable region CDR2 of SEQ ID NO: 61; and a light chain variable region CDR3 of SEQ ID NO: 75.

In one embodiment, the antibody comprised in the inventive composition comprises: a heavy chain variable region CDR1 of SEQ ID NO: 6; a heavy chain variable region CDR2 of SEQ ID NO: 20; a heavy chain variable region CDR3 of SEQ ID NO: 34; a light chain variable region CDR1 of SEQ ID NO: 48; a light chain variable region CDR2 of SEQ ID NO: 62; and a light chain variable region CDR3 of SEQ ID NO: 76.

In one embodiment, the antibody comprised in the inventive composition comprises: a heavy chain variable region CDR1 of SEQ ID NO: 7; a heavy chain variable region CDR2 of SEQ ID NO: 21; a heavy chain variable region CDR3 of SEQ ID NO: 35; a light chain variable region CDR1 of SEQ ID NO: 49; a light chain variable region CDR2 of SEQ ID NO: 63; and a light chain variable region CDR3 of SEQ ID NO: 77.

In one embodiment, the antibody comprised in the inventive composition comprises: a heavy chain variable region CDR1 of SEQ ID NO: 8; a heavy chain variable region CDR2 of SEQ ID NO: 22; a heavy chain variable region CDR3 of SEQ ID NO: 36; a light chain variable region CDR1 of SEQ ID NO: 50 a light chain variable region CDR2 of SEQ ID NO: 64; and a light chain variable region CDR3 of SEQ ID NO: 78.

In one embodiment, the antibody comprised in the inventive composition comprises: a heavy chain variable region CDR1 of SEQ ID NO: 9; a heavy chain variable region CDR2 of SEQ ID NO: 23; a heavy chain variable region CDR3 of SEQ ID NO: 37; a light chain variable region CDR1 of SEQ ID NO: 51; a light chain variable region CDR2 of SEQ ID NO: 65; and a light chain variable region CDR3 of SEQ ID NO: 79.

In one embodiment, the antibody comprised in the inventive composition comprises: a heavy chain variable region CDR1 of SEQ ID NO: 10; a heavy chain variable region CDR2 of SEQ ID NO: 24; a heavy chain variable region CDR3 of SEQ ID NO: 38; a light chain variable region CDR1 of SEQ ID NO: 52; a light chain variable region CDR2 of SEQ ID NO: 66; and a light chain variable region CDR3 of SEQ ID NO: 80.

In one embodiment, the antibody comprised in the inventive composition comprises: a heavy chain variable region CDR1 of SEQ ID NO: 11; a heavy chain variable region CDR2 of SEQ ID NO: 25; a heavy chain variable region CDR3 of SEQ ID NO: 39; a light chain variable region CDR1 of SEQ ID NO: 53; a light chain variable region CDR2 of SEQ ID NO: 67; and a light chain variable region CDR3 of SEQ ID NO: 81.

In one embodiment, the antibody comprised in the inventive composition comprises: a heavy chain variable region CDR1 of SEQ ID NO: 12; a heavy chain variable region CDR2 of SEQ ID NO: 26; a heavy chain variable region CDR3 of SEQ ID NO: 40; a light chain variable region CDR1 of SEQ ID NO: 54; a light chain variable region CDR2 of SEQ ID NO: 68; and a light chain variable region CDR3 of SEQ ID NO: 82.

In one embodiment, the antibody comprised in the inventive composition comprises: a heavy chain variable region CDR1 of SEQ ID NO: 13; a heavy chain variable region CDR2 of SEQ ID NO: 27; a heavy chain variable region CDR3 of SEQ ID NO: 41; a light chain variable region CDR1 of SEQ ID NO: 55; a light chain variable region CDR2 of SEQ ID NO: 69; and a light chain variable region CDR3 of SEQ ID NO: 83.

In one embodiment, the antibody comprised in the inventive composition comprises: a heavy chain variable region CDR1 of SEQ ID NO: 14; a heavy chain variable region CDR2 of SEQ ID NO: 28; a heavy chain variable region CDR3 of SEQ ID NO: 42; a light chain variable region CDR1 of SEQ ID NO: 56; a light chain variable region CDR2 of SEQ ID NO: 70; and a light chain variable region CDR3 of SEQ ID NO: 84.

In one embodiment, the disclosure provides a composition comprising an antibody comprising: (a) the variable heavy chain sequence of SEQ ID NO: 85 and variable light chain sequence of SEQ ID NO: 99; (b) the variable heavy chain sequence of SEQ ID NO: 86 and variable light chain sequence of SEQ ID NO: 100; (c) the variable heavy chain sequence of SEQ ID NO: 87 and variable light chain sequence of SEQ ID NO: 101; (d) the variable heavy chain sequence of SEQ ID NO: 88 and variable light chain sequence of SEQ ID NO: 102; (e) the variable heavy chain sequence of SEQ ID NO: 89 and variable light chain sequence of SEQ ID NO: 103; (f) the variable heavy chain sequence of SEQ ID NO: 90 and variable light chain sequence of SEQ ID NO: 104; (g) the variable heavy chain sequence of SEQ ID NO: 91 and variable light chain sequence of SEQ ID NO: 105; (h) the variable heavy chain sequence of SEQ ID NO: 92 and variable light chain sequence of SEQ ID NO: 106; (i) the variable heavy chain sequence of SEQ ID NO: 93 and variable light chain sequence of SEQ ID NO: 107; (j) the variable heavy chain sequence of SEQ ID NO: 94 and variable light chain sequence of SEQ ID NO: 108; (k) the variable heavy chain sequence of SEQ ID NO: 95 and variable light chain sequence of SEQ ID NO: 109; (l) the variable heavy chain sequence of SEQ ID NO: 96 and variable light chain sequence of SEQ ID NO: 110; (m) the variable heavy chain sequence of SEQ ID NO: 97 and variable light chain sequence of SEQ ID NO: 111; or (n) the variable heavy chain sequence of SEQ ID NO: 98 and variable light chain sequence of SEQ ID NO: 112.

In one embodiment, the disclosure provides a composition comprising an antibody comprising: (a) the heavy chain sequence of SEQ ID NO: 146 and light chain sequence of SEQ ID NO: 141; (b) the heavy chain sequence of SEQ ID NO: 147 and light chain sequence of SEQ ID NO: 142; (c) the heavy chain sequence of SEQ ID NO: 148 and light chain sequence of SEQ ID NO: 143; (d) the heavy chain sequence of SEQ ID NO: 149 and light chain sequence of SEQ ID NO: 144; (e) the heavy chain sequence of SEQ ID NO: 150 and light chain sequence of SEQ ID NO: 145; (f) the heavy chain sequence of SEQ ID NO: 156 and light chain sequence of SEQ ID NO: 151; (g) the heavy chain sequence of SEQ ID NO: 157 and light chain sequence of SEQ ID NO: 152; (h) the heavy chain sequence of SEQ ID NO: 158 and light chain sequence of SEQ ID NO: 153; (i) the heavy chain sequence of SEQ ID NO: 159 and light chain sequence of SEQ ID NO: 154; or (j) the heavy chain sequence of SEQ ID NO: 160 and light chain sequence of SEQ ID NO: 155.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e. greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g. murine germline sequences). In certain cases, a human antibody may be at least 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

In one embodiment the antibody comprised in the compositions of the disclosure is that encoded by pBW522 or pBW524 (deposited at DSMZ, Inhoffenstr. 7B, D-38124 Braunschweig, Germany on 18 Aug. 2009 under deposit numbers DSM22873 and DSM22874, respectively).

Homologous Antibodies

In yet another embodiment, an antibody comprised in the inventive composition has full length heavy and light chain amino acid sequences; full length heavy and light chain nucleotide sequences, variable region heavy and light chain nucleotide sequences, or variable region heavy and light chain amino acid sequences that are homologous to the amino acid and nucleotide sequences of the antibodies described herein, and wherein the antibodies retain the desired functional properties of the anti-ActRIIB antibodies of the disclosure.

For example, the disclosure provides a composition comprising an isolated recombinant anti-ActRIIB antibody (or a functional protein comprising an antigen binding portion thereof) comprising a heavy chain variable region and a light chain variable region, wherein: the heavy chain variable region comprises an amino acid sequence that is at least 80%, or at least 90% (preferably at least 95, 97 or 99%) identical to an amino acid sequence selected from the group consisting of SEQ ID NOs: 99-112; the light chain variable region comprises an amino acid sequence that is at least 80%, or at least 90% (preferably at least 95, 97 or 99%) identical to an amino acid sequence selected from the group consisting of SEQ ID NOs: 85-98; alternatively the compositions comprises a recombinant anti-ActRIIB antibody (or a functional protein comprising an antigen binding portion thereof) comprising a heavy chain variable region and a light chain variable region, wherein: the heavy chain variable region comprises no more than 5 amino acid, or no more than 4 amino acid, or no more than 3 amino acid, or no more than 2 or no more than 1 amino acid change compared to the amino acid sequence selected from the group consisting of SEQ ID NOs: 99-112; the light chain variable region comprises no more than 5 amino acid, or no more than 4 amino acid, or no more than 3 amino acid, or no more than 2 or no more than 1 amino acid change compared to the amino acid sequence selected from the group consisting of SEQ ID NOs: 85-98 and the antibody exhibits at least one of the following functional properties: (i) it inhibits myostatin binding in vitro or in vivo, (ii) decreases inhibition of muscle differentiation through the Smad-dependent pathway and/or (iii) does not induce hematological changes, in particular no changes in RBC. In this context, the term "change" refers to insertions, deletions and/or substitutions.

In a further example, the disclosure provides a composition comprising an isolated recombinant anti-ActRII antibody, (or a functional protein comprising an antigen binding portion thereof) comprising a full length heavy chain and a full length light chain, wherein: the full length heavy chain comprises an amino acid sequence that is at least 80%, or at least 90% (preferably at least 95, 97 or 99%) identical to an amino acid sequence selected from the group consisting of SEQ ID NOs: 146-150 and 156-160; the full length light chain comprises an amino acid sequence that is at least 80%, or at least 90% (preferably at least 95, 97 or 99%) identical to an amino acid sequence selected from the group consisting of SEQ ID NOs: 141-145 and 151-155; alternatively the compositions comprises a recombinant anti-ActRII antibody (or a functional protein comprising an antigen binding portion thereof) comprising a heavy chain variable region and a light chain variable region, wherein: the heavy chain variable region comprises no more than 5 amino acid, or no more than 4 amino acid, or no more than 3 amino acid, or no more than 2 or no more than 1 amino acid change compared to the amino acid sequence selected from the group consisting of SEQ ID NOs: 146-150 and 156-160; the light chain variable region comprises no more than 5 amino acid, or no more than 4 amino acid, or no more than 3 amino acid, or no more than 2 or no more than 1 amino acid change compared to the amino acid sequence selected from the group consisting of SEQ ID NOs: 141-145 and 151-155 and the antibody exhibits at least one of the following functional properties: (i) it inhibits myostatin binding in vitro or in vivo, (ii) decreases inhibition of muscle differentiation through the Smad-dependent pathway and/or (iii) does not induce hematological changes, in particular no changes in RBC. Preferably such an antibody binds to the ligand binding domain of ActRIIB and/or ActRIIA. In this context, the term "change" refers to insertions, deletions and/or substitutions.

In another example, the disclosure provides a composition comprising an isolated recombinant anti-ActRII antibody (or a functional protein comprising an antigen binding portion thereof), comprising a full length heavy chain and a full length light chain, wherein: the full length heavy chain is encoded by a nucleotide sequence that is at least 80%, or at least 90% (preferably at least 95, 97 or 99%) identical to a nucleotide sequence selected from the group consisting of SEQ ID NOs: 166-170 and 176-180; the full length light chain is encoded by a nucleotide sequence that is at least 80%, or at least 90% (preferably at least 95, 97 or 99%) identical to a nucleotide sequence selected from the group consisting of SEQ ID NOs: 161-165 and 171-175; alternatively the compositions comprises a recombinant anti-ActRIIB antibody (or a functional protein comprising an antigen binding portion thereof) comprising a heavy chain variable region and a light chain variable region, wherein: the heavy chain variable region comprises no more than 5 amino acid, or no more than 4 amino acid, or no more than 3 amino acid, or no more than 2 or no more than 1 amino acid change compared to the amino acid sequence selected from the group consisting of SEQ ID NOs: 166-170 and 176-180; the light chain variable region comprises no more than 5 amino acid, or no more than 4 amino acid, or no more than 3 amino acid, or no more than 2 or no more than 1 amino acid change compared to the amino acid sequence selected from the group consisting of SEQ ID NOs: 161-165 and 171-175 and the antibody exhibits at least one of the following functional properties: (i) it inhibits myostatin binding in vitro or in vivo, (ii) decreases inhibition of muscle differentiation through the Smad-dependent pathway and/or (iii) does not induce hematological changes, in particular no changes in RBC. Preferably such an antibody binds to the ligand binding domain of ActRIIB. In this context, the term "change" refers to insertions, deletions and/or substitutions.

In various embodiments, the antibody comprised in the inventive composition may exhibit one or more, two or more, or three of the functional properties discussed above. The antibody can be, for example, a human antibody, a humanized antibody or a chimeric antibody. Preferably the antibody is a fully human IgG1 antibody.

In other embodiments, the $V_H$ and/or $V_L$ amino acid sequences may be at least 80%, 90%, 95%, 96%, 97%, 98% or 99% identical to the sequences set forth above. In other embodiments, the $V_H$ and/or $V_L$ amino acid sequences may be identical except an amino acid substitution in no more than 1, 2, 3, 4 or 5 amino acid position. An antibody having $V_H$ and $V_L$ regions having high (i.e. 80% or greater) identity to the $V_H$ and $V_L$ regions of SEQ ID NOs 99-112 and SEQ ID NOs: 85-98 respectively, can be obtained by mutagenesis (e.g. site-directed or PCR-mediated mutagenesis) of nucleic acid molecules SEQ ID NOs: 127-140 and 113-126 respectively, followed by testing of the encoded altered antibody for retained function (i.e. the functions set forth above) using the functional assays described herein.

In other embodiments, the full length heavy chain and/or full length light chain amino acid sequences may be at least 80%, 90%, 95%, 96%, 97%, 98% or 99% identical to the sequences set forth above or may be identical except an amino acid change in no more than 1, 2, 3, 4 or 5 amino acid position. An antibody having a full length heavy chain and full length light chain having high (i.e. at least 80% or greater) identity to the full length heavy chains of any of SEQ ID NOs: 146-150 and 156-160 and full length light chains of any of SEQ ID NOs: 141-145 and 151-155 respectively, can be obtained by mutagenesis (e.g. site-directed or PCR-mediated mutagenesis) of nucleic acid molecules SEQ ID NOs: 166-170 and 176-180 and SEQ ID NOs: 161-165 and 171-175 respectively, followed by testing of the encoded altered antibody for retained function (i.e. the functions set forth above) using the functional assays described herein.

In other embodiments, the full length heavy chain and/or full length light chain nucleotide sequences may be at least 80%, 90%, 95%, 96%, 97%, 98% or 99% identical to the sequences set forth above.

In other embodiments, the variable regions of heavy chain and/or light chain nucleotide sequences may be at least 80%, 90%, 95%, 96%, 97%, 98% or 99% identical to the sequences set forth above or may be identical except an amino acid change in no more than 1, 2, 3, 4 or 5 amino acid position.

As used herein, the percent identity between the two sequences is a function of the number of identical positions shared by the sequences (i.e. % identity=#of identical positions/total #of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Antibodies with Conservative Modifications

In certain embodiments, an antibody comprised in the inventive composition has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or variant sequences thereof comprising 1, 2, 3, 4 or 5 amino acid changes or conservative modifications thereof, and wherein the antibodies retain the desired functional properties of the anti-ActRIIB antibodies of the disclosure. Accordingly, the disclosure provides compositions comprising an isolated recombinant anti-ActRIIB antibody, or a functional protein comprising an antigen binding portion thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 1-14 or variant sequences thereof comprising 1, 2, 3, 4 or 5 amino acid changes, and conservative modifications thereof; the heavy chain variable region CDR2 amino acid sequences are selected from the group consisting of SEQ ID NOs: 15-28 or variant sequences thereof comprising 1, 2, 3, 4 or 5 amino acid changes, and conservative modifications thereof; the heavy chain variable region CDR3 amino acid sequences are selected from the group consisting of SEQ ID NOs: 29-42 or variant sequences thereof comprising 1, 2, 3, 4 or 5 amino acid changes, and conservative modifications thereof; the light chain variable regions CDR1 amino acid sequences are selected from the group consisting of SEQ ID NOs: 43-56 or variant sequences thereof comprising 1, 2, 3, 4 or 5 amino acid changes, and conservative modifications thereof; the light chain variable regions CDR2 amino acid sequences are selected from the group consisting of SEQ ID NOs: 57-70 or variant sequences thereof comprising 1, 2, 3, 4 or 5 amino acid changes, and conservative modifications thereof; the light chain variable regions of CDR3 amino acid sequences are selected from the group consisting of SEQ ID NOs: 71-84 or variant sequences thereof comprising 1, 2, 3, 4 or 5 amino acid changes, and conservative modifications thereof. Preferably the antibody exhibits at least one of the following functional properties: (i) it inhibits myostatin binding in vitro or in vivo, (ii) decreases inhibition of muscle differentiation through the Smad-dependent pathway and/or (iii) does not induce hematological changes, in particular no changes in RBC.

In various embodiments, the antibody may exhibit one or both of the functional properties listed above. Such antibodies can be, for example, human antibodies, humanized antibodies or chimeric antibodies.

In other embodiments, an antibody comprised in the inventive composition optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the anti-ActRIIB antibodies of the disclosure. Accordingly, the disclosure provides compositions comprising an isolated monoclonal anti-ActRII antibody optimized for expression in a mammalian cell consisting of a full length heavy chain and a full length light chain wherein: the full length heavy chain has amino acid sequences selected from the group of SEQ ID NOs: 146-150 and 156-160 or variant sequences thereof comprising 1, 2, 3, 4 or 5 amino acid changes, and conservative modifications thereof; and the full length light chain has amino acid sequences selected from the group of SEQ ID NOs: 141-145 and 151-155 or variant sequences thereof comprising 1, 2, 3, 4 or 5 amino acid changes, and conservative modifications thereof; and the antibody exhibits at least one of the following functional properties: (i) it inhibits myostatin binding in vitro or in vivo, (ii) decreases inhibition of muscle differentiation through the Smad-dependent pathway and/or (iii) does not induce hematological changes, in particular no changes in RBC.

In various embodiments, the antibody may exhibit one or both of the functional properties listed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the CDR regions of an antibody of the disclosure can be replaced with other amino acid residues from the same side chain family, and the altered antibody can be tested for retained function using the functional assays described herein.

Antibodies that Bind to the Same Epitope as Anti-ActRII Antibodies Comprised in the Disclosed Composition In another embodiment, the disclosure provides compositions comprising antibodies that bind to the same epitope as the various specific anti-ActRII antibodies described herein. All the antibodies described in the examples that are capable of blocking myostatin binding to ActRIIA and ActRIIB bind to one of the epitopes in ActRIIA and ActRIIB with high affinity, said epitope being comprised between amino acids 19-134 of SEQ ID NO:181.

Additional antibodies can therefore be identified based on their ability to cross-compete (e.g. to competitively inhibit the binding of, in a statistically significant manner) with other antibodies of the disclosure in standard ActRIIB binding assays. The ability of a test antibody to inhibit the binding of antibodies comprised in the inventive compositions to human ActRIIB demonstrates that the test antibody can compete with said antibody for binding to human ActRIIB; such an antibody may, according to non-limiting theory, bind to the same or a related (e.g. a structurally similar or spatially proximal) epitope on human ActRIIB as the antibody with which it competes. In a certain embodiment, the antibody that binds to the same epitope on human ActRIIA and ActRIIA as the antibodies comprised in the inventive compositions is a human recombinant antibody. Such human recombinant antibodies can be prepared and isolated as described in the examples.

Thus, the disclosure provides a composition comprising an antibody that binds to an epitope recognised by and/or that competes for binding with an antibody having the variable heavy chain sequence recited in SEQ ID NO: 85, and the variable light chain sequence recited in SEQ ID NO: 99.

Thus, the disclosure provides a composition comprising an antibody that binds to an epitope recognised by an antibody having the variable heavy chain sequence recited in SEQ ID NO: 86, and the variable light chain sequence recited in SEQ ID NO: 100.

Thus, the disclosure provides a composition comprising an antibody that binds to an epitope recognised by an antibody having the variable heavy chain sequence recited in SEQ ID NO: 87, and the variable light chain sequence recited in SEQ ID NO: 101.

Thus, the disclosure provides a composition comprising an antibody that binds to an epitope recognised by an antibody having the variable heavy chain sequence recited in SEQ ID NO: 88, and the variable light chain sequence recited in SEQ ID NO: 102.

Thus, the disclosure provides a composition comprising an antibody that binds to an epitope recognised by an antibody having the variable heavy chain sequence recited in SEQ ID NO: 89, and the variable light chain sequence recited in SEQ ID NO: 103.

Thus, the disclosure provides a composition comprising an antibody that binds to an epitope recognised by an antibody having the variable heavy chain sequence recited in SEQ ID NO: 90, and the variable light chain sequence recited in SEQ ID NO: 104.

Thus, the disclosure provides a composition comprising an antibody that binds to an epitope recognized by an antibody having the variable heavy chain sequence recited in SEQ ID NO: 91, and the variable light chain sequence recited in SEQ ID NO: 105.

Thus, the disclosure provides a composition comprising an antibody that binds to an epitope recognized by an antibody having the variable heavy chain sequence recited in SEQ ID NO: 92, and the variable light chain sequence recited in SEQ ID NO: 106.

Thus, the disclosure provides a composition comprising an antibody that binds to an epitope recognised by an antibody having the variable heavy chain sequence recited in SEQ ID NO: 93, and the variable light chain sequence recited in SEQ ID NO: 107.

Thus, the disclosure provides a composition comprising an antibody that binds to an epitope recognised by an antibody having the variable heavy chain sequence recited in SEQ ID NO: 94, and the variable light chain sequence recited in SEQ ID NO: 108.

Thus, the disclosure provides a composition comprising an antibody that binds to an epitope recognised by an antibody having the variable heavy chain sequence recited in SEQ ID NO: 95, and the variable light chain sequence recited in SEQ ID NO: 109.

Thus, the disclosure provides a composition comprising an antibody that binds to an epitope recognised by an antibody having the variable heavy chain sequence recited in SEQ ID NO: 96, and the variable light chain sequence recited in SEQ ID NO: 110.

Thus, the disclosure provides a composition comprising an antibody that binds to an epitope recognised by an antibody having the variable heavy chain sequence recited in SEQ ID NO: 97, and the variable light chain sequence recited in SEQ ID NO: 111.

Thus, the disclosure provides a composition comprising an antibody that binds to an epitope recognised by an antibody having the variable heavy chain sequence recited in SEQ ID NO: 98, and the variable light chain sequence recited in SEQ ID NO: 112.

Following more detailed epitope mapping experiments, the binding regions of preferred antibodies of the inventive compositions have been more clearly defined.

Thus, the disclosure provides a composition comprising an antibody that binds to an epitope comprising amino acids 78-83 of SEQ ID NO: 181 (WLDDFN—SEQ ID NO:188).

The disclosure also provides a composition comprising an antibody that binds to an epitope comprising amino acids 76-84 of SEQ ID NO: 181 (GCWLDDFNC—SEQ ID NO:186).

The disclosure also provides a composition comprising an antibody that binds to an epitope comprising amino acids 75-85 of SEQ ID NO: 181 (KGCWLDDFNCY—SEQ ID NO:190).

The disclosure also provides a composition comprising an antibody that binds to an epitope comprising amino acids 52-56 of SEQ ID NO: 181 (EQDKR—SEQ ID NO:189).

The disclosure also provides a composition comprising an antibody that binds to an epitope comprising amino acids 49-63 of SEQ ID NO: 181 (CEGEQDKRLHCYASW—SEQ ID NO:187).

The disclosure also provides a composition comprising an antibody that binds to an epitope comprising or consisting of amino acids 29-41 of SEQ ID NO: 181 (CIYYNAN-WELERT—SEQ ID NO:191).

The disclosure also provides a composition comprising an antibody that binds to an epitope to an epitope consisting of amino acids 78-83 of SEQ ID NO: 181 (WLDDFN); and (b) binds to an epitope consisting of amino acids 49-63 of SEQ ID NO: 181 ( ).

The disclosure also provides a composition comprising antibodies that bind to epitopes consisting of these sequences or epitopes comprising combinations of these epitope regions.

Thus, the disclosure also provides a composition comprising an antibody that binds to an epitope comprising or consisting of amino acids 78-83 of SEQ ID NO: 181 (WLDDFN) and amino acids 52-56 of SEQ ID NO: 181 (EQDKR).

Engineered and Modified Antibodies

An antibody comprised in the inventive compositions further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i.e. $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g. Riechmann, L. et al., 1998 Nature 332:323-327; Jones, P. et al., 1986 Nature 321:522-525; Queen, C. et al., 1989 Proc. Natl. Acad. Sci. U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the disclosure pertains to compositions comprising a monoclonal anti-ActRII antibody, or a functional protein comprising an antigen binding portion thereof, comprising a heavy chain variable region comprising CDR1 sequences having an amino acid sequence selected from the group consisting of SEQ ID NOs: 1-14; CDR2 sequences having an amino acid sequence selected from the group consisting of SEQ ID NOs: 15-28; CDR3 sequences having an amino acid sequence selected from the group consisting of SEQ ID NOs: 29-42, respectively; and a light chain variable region having CDR1 sequences having an amino acid sequence selected from the group consisting of SEQ ID NOs: 43-56; CDR2 sequences having an amino acid sequence selected from the group consisting of SEQ ID NOs: 57-70; and CDR3 sequences consisting of an amino acid sequence selected from the group consisting of SEQ ID NOs: 71-84, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., [supra]; Tomlinson, I. M., et al., 1992 J. fol. Biol. 227:776-798; and Cox, J. P. L. et al., 1994 Eur. J Immunol. 24:827-836. An example of framework sequences for use in the antibodies of the disclosure are those that are structurally similar to the framework sequences used by selected antibodies of the disclosure, e.g. consensus sequences and/or framework sequences used by monoclonal antibodies of the disclosure. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g. U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g. affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the disclosure provides isolated anti-ActRII monoclonal antibodies, or a functional protein comprising an antigen binding portion thereof, consisting of a heavy chain variable region having: a $V_H$ CDR1 region consisting of an amino acid sequence selected from the group having SEQ ID NOs: 1-14 or an amino acid sequence having one, two, three, four or five amino acid substitutions, deletions or additions as compared to SEQ ID NOs: 1-14; a $V_H$ CDR2 region having an amino acid sequence selected from the group consisting of SEQ ID NOs: 15-28, or an amino acid sequence having one, two, three, four or five amino acid substitutions, deletions or additions as compared to SEQ ID NOs: 15-28; a $V_H$ CDR3 region having an amino acid sequence selected from the group consisting of SEQ ID NOs: 29-42, or an amino acid sequence having one, two, three, four or five amino acid substitutions, deletions or additions as compared to SEQ ID NOs: 29-42; a $V_L$ CDR1 region having an amino acid sequence selected from the group consisting of SEQ ID NOs: 43-56, or an amino acid sequence having one, two, three, four or five amino acid substitutions, deletions or additions as compared to SEQ ID NOs: 43-56; a $V_L$ CDR2 region having an amino acid sequence selected from the group consisting of SEQ ID NOs: 52-70, or an amino acid sequence having one, two, three, four or five amino acid substitutions, deletions or additions as compared to SEQ ID NOs: 52-70; and a $V_L$ CDR3 region having an amino acid sequence selected from the group consisting of SEQ ID NOs: 71-84, or an amino acid sequence having one, two, three, four or five amino acid substitutions, deletions or additions as compared to SEQ ID NOs: 71-84.

Camelid Antibodies

Antibody proteins obtained from members of the camel and dromedary family (*Camelus bactrianus* and *Camelus dromaderius*) including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals (see WO94/04678).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody" (see U.S. Pat. No. 5,759,808; Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520). Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e. the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e. camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitate drug transport across the blood brain barrier (see US2004/0161738). These features combined with the low antigenicity to humans indicate great therapeutic potential. Further, these molecules can be fully expressed in prokaryotic cells such as *E. coli* and are expressed as fusion proteins with bacteriophage and are functional.

Accordingly, in one embodiment, the present disclosure related to composition comprising a camelid antibody or nanobody having high affinity for ActRIIB. In certain embodiments herein, the camelid antibody or nanobody is naturally produced in the camelid animal, i.e. is produced by the camelid following immunization with ActRIIB or a peptide fragment thereof, using techniques described herein for other antibodies. Alternatively, the anti-ActRIIB camelid nanobody is engineered, i.e. produced by selection for example from a library of phage displaying appropriately mutagenized camelid nanobody proteins using panning procedures with ActRIIB as a target as described in the examples herein. Engineered nanobodies can further be customized by genetic engineering to have a half-life in a recipient subject of from 45 minutes to two weeks. In a specific embodiment, the camelid antibody or nanobody is obtained by grafting the CDRs sequences of the heavy or light chain of the human antibodies of the disclosure into nanobody or single domain antibody framework sequences, as described for example in WO94/04678.

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immuno-pharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectin Scaffold

The fibronectin scaffolds are based preferably on fibronectin type III domain (e.g. the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the disclosure using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US2004/0175756; US2005/0053973; US2005/0048512; and US2006/0008844.

(vi) Protein A—Affibody

Affibody® affinity ligands are small, simple proteins composed of a three-helix bundle based on the scaffold of one of the IgG-binding domains of Protein A. Protein A is a surface protein from the bacterium Staphylococcus aureus. This scaffold domain consists of 58 amino acids, 13 of which are randomized to generate Affibody® libraries with a large number of ligand variants (See e.g. U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of Pieris brassicae has been used to develop anticalins by mutagenizing the set of four loops. One example of a patent application describing "anticalins" is WO1999/16873.

(vi) Affilin—Scil Proteins

AFFILIN™ molecules are small non-immunoglobulin proteins which are designed for specific affinities towards proteins and small molecules. New AFFILIN™ molecules can be very quickly selected from two libraries, each of which is based on a different human derived scaffold protein.

AFFILIN™ molecules do not show any structural homology to immunoglobulin proteins. Scil Proteins employs two AFFILIN™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO2001/004144 and examples of "ubiquitin-like" proteins are described in WO2004/106368.

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to ActRIIB. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the compositions of the disclosure may comprise non-immunoglobulin based antibodies using non-immunoglobulin scaffolds onto which CDRs of the disclosed antibodies can be grafted. Known or future non-immunoglobulin frameworks and scaffolds may be employed, as long as they comprise a binding region specific for the target protein of SEQ ID NO: 181 (preferably, the ligand binding domain thereof as shown in SEQ ID NO: 182). Such compounds are known herein as "polypeptides comprising a target-specific binding region". Examples of non-immunoglobulin framework are further described in the sections below (camelid antibodies and non-antibody scaffold).

Framework or Fc Engineering

Engineered antibodies comprised in the compositions of the disclosure include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies can also be comprised in the compositions of the disclosure.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in US2003/0153043.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody comprised in the compositions of the disclosure may be chemically modified (e.g. one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g. increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. No. 5,869,046 and U.S. Pat. No. 6,121,022.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. No. 5,624,821 and U.S. Pat. No. 5,648,260, both by Winter et al. In particular, residues 234 and 235 may be mutated. In particular, these mutations may be to alanine. Thus in one embodiment the antibody comprised in the compositions of the disclosure has a mutation in the Fc region at one or both of amino acids 234 and 235. In another embodiment, one or both of amino acids 234 and 235 may be substituted to alanine. Substitution of both amino acids 234 and 235 to alanine results in a reduced ADCC activity.

In another embodiment, one or more amino acids selected from amino acid residues of the described antibodies can be replaced with a different amino acid residue such that the antibody has altered C1q binding and/or reduced or abolished complement dependent cytotoxicity (CDC). This approach is described in further detail in U.S. Pat. No. 6,194,551.

In another embodiment, one or more amino acid residues of the described antibodies are altered to thereby alter the ability of the antibody to fix complement. This approach is described further in WO94/29351.

In yet another embodiment, the Fc region of the described antibodies is modified to increase the ability of the antibody to mediate antibody dependent cellular cytotoxicity (ADCC) and/or to increase the affinity of the antibody for an Fcγ receptor by modifying one or more amino acids. This approach is described further in WO00/42072. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody comprised in the compositions of the disclosure is modified. For example, an aglycoslated antibody can be made (i.e. the antibody lacks glycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be used that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express the disclosed recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies comprised in the compositions of the disclosure are produced by recombinant expression in a cell line which exhibit hypofucosylation pattern, for example, a mammalian cell line with deficient expression of the FUT8 gene encoding fucosyltransferase. WO03/035835 describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). WO99/54342 describes cell lines engineered to express glycoprotein-modifying glycosyl transferases (e.g. beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies comprised in the compositions of the disclosure can be produced in a yeast or a filamentous fungi engineered for mammalian-like glycosylation pattern, and capable of producing antibodies lacking fucose as glycosylation pattern (see for example EP1297172B1).

Another modification of the antibodies herein that is contemplated by the disclosure is pegylation. An antibody can be pegylated to, for example, increase the biological (e.g. serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the used antibody to be pegylated is an aglycosylated antibody. Methods for pegylating proteins are known in the art and can be applied to the disclosed antibodies (see for example, EP0154316 and EP0401384).

Another modification of the antibodies that is contemplated by the disclosure is a conjugate or a protein fusion of at least the antigen-binding region of the antibody comprised in the composition of the disclosure to serum protein, such as human serum albumin or a fragment thereof to increase half-life of the resulting molecule (see, for example, EP0322094).

Another possibility is a fusion of at least the antigen-binding region of the antibody comprised in the composition of the disclosure to proteins capable of binding to serum proteins, such as human serum albumin to increase half-life of the resulting molecule (see, for example, EP0486525).

Methods of Engineering Altered Antibodies

As discussed above, the anti-ActRIIB antibodies having CDR sequences, $V_H$ and $V_L$ sequences or full length heavy and light chain sequences shown herein can be used to create new anti-ActRIIB antibodies by modifying the CDR sequences full length heavy chain and/or light chain sequences, $V_H$ and/or $V_L$ sequences, or the constant region(s) attached thereto. Thus, in another aspect of the disclosure, the structural features of an anti-ActRIIB antibody comprised in the compositions of the disclosure are used to create structurally related anti-ActRIIB antibodies that retain at least one functional property of the antibodies comprised in the compositions of the disclosure, such as binding to human ActRIIB but also inhibit one or more functional properties of ActRIIB (for example, the inhibition of Smad activation).

For example, one or more CDR regions of the antibodies comprised in the compositions of the present disclosure, or mutations thereof, can be combined recombinantly with known framework regions and/or other CDRs to create additional, recombinantly-engineered, anti-ActRIIB antibodies comprised in the compositions of the disclosure, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e. express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

The altered antibody sequence can also be prepared by screening antibody libraries having fixed CDR3 sequences selected among the group consisting of SEQ ID NO: 29-42 and SEQ ID NO: 71-84 or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the anti-ActRIIB antibodies described herein, which functional properties include, but are not limited to, specifically binding to human ActRIIB and inhibition of Smad activation.

The altered antibody may exhibit one or more, two or more, or three or more of the functional properties discussed above.

The functional properties of the altered antibodies can be assessed using standard assays available in the art and/or described herein, such as those set forth in the Examples (e.g. ELISAs).

Mutations can be introduced randomly or selectively along all or part of an anti-ActRIIB antibody coding sequence and the resulting modified anti-ActRIIB antibodies can be screened for binding activity and/or other functional properties as described herein. Mutational methods have been described in the art. For example, WO02/092780 describes methods for creating and screening antibody mutations using saturation mutagenesis, synthetic ligation assembly, or a combination thereof. Alternatively, WO03/074679 describes methods of using computational screening methods to optimize physiochemical properties of antibodies.

Nucleic Acid Molecules Encoding Antibodies Comprised in the Compositions of the Disclosure Examples of full length light chain nucleotide sequences optimized for expression in a mammalian cell are shown in SEQ ID NOs: 161-165 and 171-175. Examples of full length heavy chain nucleotide sequences optimized for expression in a mammalian cell are shown in SEQ ID NOs: 166-170 and 176-180.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g. other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. Nucleic acids can be obtained using standard molecular biology techniques. For antibodies expressed by hybridomas (e.g. hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g. using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g. Kabat, E. A., et al. [supra]) and DNA fragments encompassing these regions can be obtained by standard PCR amplification. The heavy chain constant region can be an IgG1, IgG2, IgG3, IgG4, IgA, IgE, IgM or IgD constant region. The heavy chain constant region can be selected among IgG1 isotypes. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g. Kabat, E. A., et al. [supra]) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g. encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g. Bird et al., 1988 Science 242:423-426; Huston et al., 1988 Proc. Natl. Acad. Sci. USA 85:5879-5883; McCafferty et al., 1990 Nature 348:552-554).

Generation of Monoclonal Antibodies

Monoclonal antibodies (mAbs) can be produced by a variety of techniques, including conventional monoclonal antibody methodology e.g. the standard somatic cell hybridization technique of Kohler and Milstein (1975 Nature 256: 495). Many techniques for producing monoclonal antibody can be employed e.g. viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g. murine myeloma cells) and fusion procedures are also known.

Chimeric or humanized antibodies comprised in the compositions of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g. human) immunoglobulin sequences using standard molecular biology techniques. For example, to create a chimeric antibody, the murine variable regions can be linked to human constant regions using methods known in the art (see e.g. U.S. Pat. No. 4,816,567). To create a humanized antibody, the murine CDR regions can be inserted into a human framework using methods known in the art (see e.g. U.S. Pat. Nos. 5,225,539; 5,530,101; 5,585,089; 5,693,762 and 6,180,370).

In a certain embodiment, the antibodies comprised in the compositions of the disclosure are human monoclonal antibodies. Such human monoclonal antibodies directed against ActRIIB can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g. Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 [supra]; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992

Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; as well as WO92/103918, WO93/12227, WO94/25585, WO97/113852, WO98/24884; WO99/45962; and WO01/14424.

In another embodiment, human antibodies comprised in the compositions of the disclosure can be raised using a mouse that carries human immunoglobulin sequences on transgenes and transchomosomes such as a mouse that carries a human heavy chain transgene and a human light chain transchromosome. Such mice, referred to herein as "KM mice", are described in detail in WO02/43478.

Still further, alternative transgenic animal systems expressing human immunoglobulin genes are available in the art and can be used to raise anti-ActRIIB antibodies of the disclosure. For example, an alternative transgenic system referred to as the Xenomouse (Abgenix, Inc.) can be used. Such mice are described in, e.g. U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise anti-ActRIIB antibodies of the disclosure. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-ActRIIB antibodies.

Human recombinant antibodies comprised in the compositions of the disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; 5,571,698; 5,427,908; 5,580,717; 5,969,108; 6,172,197; 5,885,793; 6,521,404; 6,544,731; 6,555,313; 6,582,915 and 6,593,081.

Human monoclonal antibodies comprised in the compositions of the disclosure can also be prepared using SCID mice into which human immune cells have been reconstituted such that a human antibody response can be generated upon immunization. Such mice are described in, for example, U.S. Pat. Nos. 5,476,996 and 5,698,767.

Generation of Hybridomas Producing Human Monoclonal Antibodies

To generate hybridomas producing human monoclonal antibodies comprised in the compositions of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies comprised in the compositions of the disclosure also can be produced in a host cell transfectoma using, for example, a combination of recombinant DNA techniques and gene transfection methods as is well known in the art (e.g. Morrison, S. (1985) Science 229:1202).

For example, to express the antibodies, or antibody fragments thereof, DNAs encoding partial or full-length light and heavy chains, can be obtained by standard molecular biology techniques (e.g. PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g. ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e. a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g. the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g. electroporation, calcium-phosphate precipitation, DEAE-dextran transfection and the like. It is theoretically possible to express the antibodies of the disclosure in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies comprised in the compositions of the disclosure include Chinese Hamster Ovary (CHO cells) (including dhfr-CHO cells, described Urlaub and Chasing, 1980 Proc. Natl. Acad. Sci. USA 77:4216-4220 used with a DHFR selectable marker, e.g. as described in R. J. Kaufman and P. A. Sharp, 1982 Mol. Biol. 159:601-621), NSO myeloma cells, COS cells and SP2 cells. In one embodiment the host cells are CHO K1PD cells. In particular, for use with NSO myeloma cells, another expression system is the GS gene expression system shown in WO87/04462, WO89/01036 and EP 338,841. Mammalian host cells for expressing the recombinant antibodies comprised in the compositions of the disclosure include mammalian cell lines deficient for FUT8 gene expression, for example as described in U.S. Pat. No. 6,946,292B2. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Immunoconjugates

In another aspect, the present disclosure features compositions comprising an anti-ActRIIB antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells.

Cytotoxins can be conjugated to antibodies of the disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g. cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G. 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies comprised in the compositions of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Methods for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the disclosure.

The antibody conjugates comprised in the compositions of the disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g. Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Inmunol. Rev., 62:119-58 (1982).

Bispecific Molecules

In another aspect, the present disclosure features compositions comprising bispecific or multispecific molecules comprising an anti-ActRIIB antibody, or a fragment thereof, of the disclosure. An antibody comprised in the compositions of the disclosure, or antigen-binding regions thereof, can be derivatized or linked to another functional molecule, e.g. another peptide or protein (e.g. another antibody or ligand for a receptor) to generate a bispecific molecule that binds to at least two different binding sites or target molecules. The antibody of the disclosure may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the disclosure, an antibody of the disclosure can be functionally linked (e.g. by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes compositions comprising bispecific molecules comprising at least one first binding specificity for ActRIIB and a second binding specificity for a second target epitope. For example, the second target epitope may be another epitope of ActRIIB different from the first target epitope.

Additionally, for the compositions in which the bispecific molecule is multi-specific, the molecule can further include a third binding specificity, in addition to the first and second target epitope.

In one embodiment, the bispecific molecules of the disclosed compositions comprise as a binding specificity at least one antibody, or an antibody fragment thereof, including, e.g. an Fab, Fab', F(ab)₂, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

Other antibodies which can be employed in the bispecific molecules are murine, chimeric and humanized monoclonal antibodies.

The bispecific molecules comprised in the compositions of the present disclosure can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g. Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab)₂ or ligand×Fab fusion protein. A bispecific molecule comprised in the compositions of the disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labeled reagent (e.g. an antibody) specific for the complex of interest.

Multivalent Antibodies

In another aspect, the present disclosure relates to compositions comprising multivalent antibodies comprising at least two identical or different antigen-binding portions of the disclosed antibodies binding to ActRIIB. In one embodiment, the multivalent antibodies provide at least two, three or four antigen-binding portions of the antibodies. The antigen-binding portions can be linked together via protein fusion or covalent or non-covalent linkage. Alternatively, methods of linkage have been described for the bispecific molecules. In various embodiments, the composition can be mono-, bi- or multi-valent (e.g., capable of binding to one, two or several antigens), and/or mono-, bi- or multi-specific (e.g., having binding region(s) capable of binding to one, two or several different antigens). a composition can be any combination of these, e.g., monovalent and mono-specific (having one binding region that binds to one antigen or epitope); or bi-valent and bi-specific (having two binding regions, each of which bind to a different epitope or antigen); or bi-valent and mono-specific (having two binding regions, each of which bind to the same epitope or antigen); or multi-valent and mono-specific (having several binding regions that all bind to the same antigen or epitope); or multi-valent and multi-specific (having several binding regions that bind to several different antigens or epitopes).

Pharmaceutical Compositions

In another aspect, the present disclosure provides a composition, e.g. a pharmaceutical composition, containing one or a combination of the above described antibodies/monoclonal antibodies, or antigen-binding portion(s) thereof, formulated together with a pharmaceutically acceptable carrier. Such compositions may include one or a combination of (e.g. two or more different) the described antibodies, or immunoconjugates or bispecific molecules. For example, a pharmaceutical composition of the disclosure can comprise a combination of antibodies that bind to different epitopes on the target antigen or that have complementary activities.

Pharmaceutical compositions of the disclosure also can be administered in combination therapy, i.e. combined with other agents. For example, the combination therapy can include an anti-ActRII antibody of the present disclosure combined with at least one other muscle mass/strength increasing agent, for example, IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g. by injection or infusion), preferably for intravenous injection or infusion. Depending on the route of administration, the active compound, i.e. antibody, immunoconjuage, or bispecific molecule, may be coated in a material to protect the compound from the action of acids and other natural conditions that may inactivate the compound.

The pharmaceutical compositions of the disclosure may include one or more pharmaceutically acceptable salts. A "pharmaceutically acceptable salt" refers to a salt that retains the desired biological activity of the parent compound and does not impart any undesired toxicological effects (see e.g. Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of agents enumerated above, as required, followed by sterilization microfiltration. Generally, dispersions are prepared by incorporating the active compound into a sterile vehicle that contains a basic dispersion medium and the required other agents from those enumerated above. In the case of sterile powders for the preparation of sterile injectable solutions, the methods of preparation are vacuum drying and freeze-drying (lyophilization) that yield a powder of the active agent plus any additional desired agent from a previously sterile-filtered solution thereof.

The amount of active agent which can be combined with a carrier material to produce a single dosage form will vary depending upon the subject being treated, and the particular mode of administration. The amount of active agent which can be combined with a carrier material to produce a single dosage form will generally be that amount of the composition which produces a therapeutic effect. Generally, out of one hundred percent, this amount will range from about 0.01 percent to about ninety-nine percent of active agent, from about 0.1 percent to about 70 percent, or from about 1 percent to about 30 percent of active agent in combination with a pharmaceutically acceptable carrier.

Dosage regimens are adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of sensitivity in individuals.

For administration of the antibody comprising composition, the antibody dosage ranges from about 0.0001 to about 100 mg/kg, and more usually about 0.01 to about 30 mg/kg, of the host body weight. For example dosages are about 1 mg/kg body weight, about 3 mg/kg body weight, about 5 mg/kg body weight or about 10 mg/kg body weight within the ranges of about 1-10 mg/kg e.g., about 1, 2, 3, 4, 5, 6, 7, 8, 9, 10 mg/kg body weight, preferably once every 4 weeks. Such administration is preferably carried out intravenously. Dosage regimens for an anti-ActRII antibody of the disclosure, e.g., bimagrumab, include about 1 mg/kg body weight or about 3 mg/kg body weight or about 10 mg/kg body once every four weeks weight by intravenous administration.

Also, the dosage ranges above can be administered at corresponding fixed doses on the basis of a 70 kg adult individual average weight.

For example dosages are about 70 mg, about 210 mg, about 350 mg or about 500 mg or about 700 mg within the ranges of about 70-700 mg/kg e.g., about 70, 140, 210, 280, 350, 420, 490, 560, 630, 700 mg/kg body weight, preferably once every 4 weeks Preferably the compositions of the disclosure are for use in accelerating/improving physical recovery in a patient with disuse atrophy triggered by reduced mobility due to a hip fracture and consequent major surgery.

In some methods, two or more monoclonal antibodies with different binding specificities are comprised in the compositions of the disclosure and, thus, administered simultaneously, in which case the dosage of each antibody administered falls within the ranges indicated. An antibody is usually administered on multiple occasions. Intervals between single dosages can be, for example, weekly, monthly, every three months, every six months or yearly. Intervals can also be irregular as indicated by measuring blood levels of antibody to the target antigen in the patient. In some methods, dosage is adjusted to achieve a plasma antibody concentration of about 1- about 1000 µg/ml and in some methods about 25- about 300 µg/ml. For example, an ActRII antibody of the disclosure could be co-administered with an anti-myostatin antibody.

Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Administration of a "therapeutically effective dosage" of an anti-ActRII antibody comprised in the compositions of the disclosure can result in a decrease in severity of disease symptoms, an increase in frequency and duration of disease symptom-free periods, or a prevention of impairment or disability due to the disease affliction i.e. an increase in muscle mass and/or strength.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978.

Therapeutic compositions can be administered with medical devices known in the art.

Uses and Methods of the Disclosure

The compositions of the present disclosure and the disclosed antibodies have therapeutic utilities, because they have an impact on the treatment of sporadic inclusion body myositis or on the amelioration of the condition of patients affected by sporadic inclusion body myositis or on the reduction of symptoms associated with sporadic inclusion body myositis.

The term "subject" or "individual" as used herein is intended to include human and non-human animals. Nonhuman animals include all vertebrates, e.g. mammals and non-mammals, such as non-human primates, sheep, dogs, cats, cows, horses, chickens, amphibians, and reptiles.

Hence, the disclosure also relates to methods of treatment in which compositions of the disclosure or the disclosed myostatin antagonists, e.g., myostatin binding molecules or ActRII binding molecules, preferably ActRII binding molecules, more preferably antibodies to ActRII, e.g, bimagrumab or BYM338, inhibit, i.e. antagonize, the function of ActRII and thereby resulting in the improvement in hip fracture surgery recovery. The disclosure provides a method of accelerating/improving physical recovery in a patient with disuse atrophy triggered by reduced mobility due to a hip fracture and consequent major surgery comprising administering a therapeutically effective amount of a myostatin antagonist, e.g., myostatin binding molecule or ActRIIB binding molecule, preferably ActRIIB binding molecule, more preferably an antagonist antibody to ActRIIB, e.g, bimagrumab or BYM338 or the disclosed compositions to the patient.

Examples of myostatin antagonists, e.g., myostatin binding molecules or ActRII binding molecules, preferably ActRIIB binding molecules, more preferably antagonist antibodies to ActRIIB, e.g, bimagrumab or BYM338, that can be used in the disclosed methods of treatment are those disclosed or described in detail above. In certain embodiments, the ActRII antibodies (e.g., bimagrumab or BYM338) are comprised in the herein disclosed inventive compositions.

The disclosure also relates to the use of a myostatin anti-antagonist, e.g., myostatin binding molecule or ActRIIB binding molecule, preferably ActRIIB binding molecule, more preferably an antagonist antibody to ActRII, e.g, BYM338, in the manufacture of a medicament for accelerating/improving physical recovery in a patient with disuse atrophy triggered by reduced mobility due to a hip fracture and consequent major surgery In a further embodiment, the patient may be one who has not responded to previous treatments. For example, the patient may not have responded to treatment with IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. A simple way of measuring a patient's response to treatment may be timing how long it takes for a patient to climb a known height of stairs and comparing the results both before and after treatment.

The myostatin antagonist, e.g., myostatin binding molecule or ActRII binding molecule, preferably ActRII binding molecule, more preferably an antagonist antibody to ActRII, e.g., bimagrumab or BYM338, may be administered as the sole active agent or in conjunction with, e.g. as an adjuvant to or in combination to, other drugs e.g. IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. For example, the antagonists of the disclosure may be used in combination with an IGF-1 mimetic as disclosed in WO2007/146689.

In accordance with the foregoing the present disclosure provides in a yet further aspect: A method or use as defined above comprising co-administration, e.g. concomitantly or in sequence, of a therapeutically effective amount of a myostatin antagonist, e.g., myostatin binding molecule or ActRII binding molecule, preferably an ActRII or binding molecule, more preferably an antagonist antibody to ActRII, e.g, bimagrumab or BYM338, and at least one second drug substance, said second drug substance being IGF-1, IGF-2 or variants of IGF-1 or IGF-2, an anti-myostatin antibody, a myostatin propeptide, a myostatin decoy protein that binds ActRII but does not activate it, a beta 2 agonist, a Ghrelin agonist, a SARM, GH agonists/mimetics or follistatin.

Kits

The invention also encompasses kits which may comprise a myostatin antagonist, e.g., a myostatin binding molecule (e.g., a myostatin antibody or antigen binding fragment thereof, e.g., bimagrumab or BYM338) or myostatin receptor (i.e., ActRIIB receptor) binding molecule (e.g., anti-ActRIIB antibody or antigen binding fragment thereof) (e.g., in liquid or lyophilized form) or a pharmaceutical composition comprising the myostatin antagonist (described supra). Additionally, such kits may comprise means for administering the myostatin antagonist (e.g., a syringe and vial, a prefilled syringe, a prefilled pen) and instructions for use. These kits may contain additional therapeutic agents (described supra), e.g., for delivery in combination with the enclosed myostatin antagonist, e.g., BYM338.

The phrase "means for administering" is used to indicate any available implement for systemically administering a drug top a patient, including, but not limited to, a pre-filled syringe, a vial and syringe, an injection pen, an autoinjector, an i.v. drip and bag, a pump, etc. With such items, a patient may self-administer the drug (i.e., administer the drug on their own behalf) or a physician may administer the drug.

Each component of the kit is usually enclosed within an individual container, and all of the various containers are within a single package along with instructions for use.

Sequences

TABLE 1 sequence listing

| SEQ ID NO | Ab region | Sequence |
|---|---|---|
| SEQ ID NO 1 | HCDR1 | GYTFTSSYIN |
| SEQ ID NO 2 | HCDR1 | GYTFTSSYIN |
| SEQ ID NO 3 | HCDR1 | GYTFTSSYIN |
| SEQ ID NO 4 | HCDR1 | GYTFTSSYIN |
| SEQ ID NO 5 | HCDR1 | GYTFTSSYIN |
| SEQ ID NO 6 | HCDR1 | GYTFTSSYIN |

TABLE 1-continued sequence listing

| SEQ ID NO | Ab region | Sequence |
|---|---|---|
| SEQ ID NO 7 | HCDR1 | GYTFTSSYIN |
| SEQ ID NO 8 | HCDR1 | GYTFTSSYIN |
| SEQ ID NO 9 | HCDR1 | GYTFTSSYIN |
| SEQ ID NO 10 | HCDR1 | GYTFTSSYIN |
| SEQ ID NO 11 | HCDR1 | GYTFTSSYIN |
| SEQ ID NO 12 | HCDR1 | GYTFTSSYIN |
| SEQ ID NO 13 | HCDR1 | GYTFTSSYIN |
| SEQ ID NO 14 | HCDR1 | GYTFTSSYIN |
| SEQ ID NO 15 | HCDR2 | TINPVSGNTSYAQKFQG |
| SEQ ID NO 16 | HCDR2 | TINPVSGNTSYAQKFQG |
| SEQ ID NO 17 | HCDR2 | TINPVSGNTSYAQKFQG |
| SEQ ID NO 18 | HCDR2 | TINPVSGNTSYAQKFQG |
| SEQ ID NO 19 | HCDR2 | MINAPIGTTRYAQKFQG |
| SEQ ID NO 20 | HCDR2 | QINAASGMTRYAQKFQG |
| SEQ ID NO 21 | HCDR2 | MINAPIGTTRYAQKFQG |
| SEQ ID NO 22 | HCDR2 | TINPVSGNTRYAQKFQG |
| SEQ ID NO 23 | HCDR2 | TINPVSGSTSYAQKFQG |
| SEQ ID NO 24 | HCDR2 | QINAASGMTRYAQKFQG |
| SEQ ID NO 25 | HCDR2 | NINAAAGITLYAQKFQG |
| SEQ ID NO 26 | HCDR2 | TINPPTGGTYYAQKFQG |
| SEQ ID NO 27 | HCDR2 | GINPPAGTTSYAQKFQG |
| SEQ ID NO 28 | HCDR2 | NINPATGHADYAQKFQG |
| SEQ ID NO 29 | HCDR3 | GGWFDY |
| SEQ ID NO 30 | HCDR3 | GGWFDY |
| SEQ ID NO 31 | HCDR3 | GGWFDY |
| SEQ ID NO 32 | HCDR3 | GGWFDY |
| SEQ ID NO 33 | HCDR3 | GGWFDY |
| SEQ ID NO 34 | HCDR3 | GGWFDY |
| SEQ ID NO 35 | HCDR3 | GGWFDY |
| SEQ ID NO 36 | HCDR3 | GGWFDY |
| SEQ ID NO 37 | HCDR3 | GGWFDY |
| SEQ ID NO 38 | HCDR3 | GGWFDY |
| SEQ ID NO 39 | HCDR3 | GGWFDY |
| SEQ ID NO 40 | HCDR3 | GGWFDY |
| SEQ ID NO 41 | HCDR3 | GGWFDY |
| SEQ ID NO 42 | HCDR3 | GGWFDY |
| SEQ ID NO 43 | LCDR1 | TGTSSDVGSYNYVN |
| SEQ ID NO 44 | LCDR1 | TGTSSDVGSYNYVN |

TABLE 1-continued sequence listing

| SEQ ID NO | Ab region | Sequence |
|---|---|---|
| SEQ ID NO 45 | LCDR1 | TGTSSDVGSYNYVN |
| SEQ ID NO 46 | LCDR1 | TGTSSDVGSYNYVN |
| SEQ ID NO 47 | LCDR1 | TGTSSDVGSYNYVN |
| SEQ ID NO 48 | LCDR1 | TGTSSDVGSYNYVN |
| SEQ ID NO 49 | LCDR1 | TGTSSDVGSYNYVN |
| SEQ ID NO 50 | LCDR1 | TGTSSDVGSYNYVN |
| SEQ ID NO 51 | LCDR1 | TGTSSDVGSYNYVN |
| SEQ ID NO 52 | LCDR1 | TGTSSDVGSYNYVN |
| SEQ ID NO 53 | LCDR1 | TGTSSDVGSYNYVN |
| SEQ ID NO 54 | LCDR1 | TGTSSDVGSYNYVN |
| SEQ ID NO 55 | LCDR1 | TGTSSDVGSYNYVN |
| SEQ ID NO 56 | LCDR1 | TGTSSDVGSYNYVN |
| SEQ ID NO 57 | LDCR2 | LMIYGVSKRPS |
| SEQ ID NO 58 | LDCR2 | LMIYGVSKRPS |
| SEQ ID NO 59 | LDCR2 | LMIYGVSKRPS |
| SEQ ID NO 60 | LDCR2 | LMIYGVSKRPS |
| SEQ ID NO 61 | LDCR2 | LMIYGVSKRPS |
| SEQ ID NO 62 | LDCR2 | LMIYGVSKRPS |
| SEQ ID NO 63 | LDCR2 | LMIYGVSKRPS |
| SEQ ID NO 64 | LDCR2 | LMIYGVSKRPS |
| SEQ ID NO 65 | LDCR2 | LMIYGVSKRPS |
| SEQ ID NO 66 | LDCR2 | LMIYGVSKRPS |
| SEQ ID NO 67 | LDCR2 | LMIYGVSKRPS |
| SEQ ID NO 68 | LDCR2 | LMIYGVSKRPS |
| SEQ ID NO 69 | LDCR2 | LMIYGVSKRPS |
| SEQ ID NO 70 | LDCR2 | LMIYGVSKRPS |
| SEQ ID NO 71 | LCDR3 | QAVVTSKMAG |
| SEQ ID NO 72 | LCDR3 | SSYTRMGHP |
| SEQ ID NO 73 | LCDR3 | ATYGKGVTPP |
| SEQ ID NO 74 | LCDR3 | GTFAGGSYYG |
| SEQ ID NO 75 | LCDR3 | QAVVTSKMAG |
| SEQ ID NO 76 | LCDR3 | QAVVTSKMAG |
| SEQ ID NO 77 | LCDR3 | GTFAGGSYYG |
| SEQ ID NO 78 | LCDR3 | GTFAGGSYYG |
| SEQ ID NO 79 | LCDR3 | GTFAGGSYYG |
| SEQ ID NO 80 | LCDR3 | GTFAGGSYYG |
| SEQ ID NO 81 | LCDR3 | GTFAGGSYYG |

TABLE 1-continued sequence listing

| SEQ ID NO | Ab region | Sequence |
|---|---|---|
| SEQ ID NO 82 | LCDR3 | GTFAGGSYYG |
| SEQ ID NO 83 | LCDR3 | GTFAGGSYYG |
| SEQ ID NO 84 | LCDR3 | GTFAGGSYYG |
| SEQ ID NO 85 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCQAVVTSKMAGVFGGGTKLTVLGQ |
| SEQ ID NO 86 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCSSYTRMGHPVFGGGTKLTVLGQ |
| SEQ ID NO 87 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCATYGKGVTPPVFGGGTKLTVLGQ |
| SEQ ID NO 88 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 89 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCQAVVTSKMAGVFGGGTKLTVLGQ |
| SEQ ID NO 90 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCQAVVTSKMAGVFGGGTKLTVLGQ |
| SEQ ID NO 91 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 92 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 93 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 94 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 95 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 96 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 97 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 98 | VL | DIALTQPASVSGSPGQSITISCTGTSSDVGSYNYVNWYQQHPGKAPKLMIYGVSKRPSGV<br>SNRFSGSKSGNTASLTISGLQAEDEADYYCGTFAGGSYYGVFGGGTKLTVLGQ |
| SEQ ID NO 99 | VH | QVQLVQSGAEVKKPGASVKVSCKASGYTFTSSYINWVRQAPGQGLEVVMGTINPVSGNT<br>SYAQKFQGRVTMTRDTSISTAYMELSSLRSEDTAVYYCARGGWFDYWGQGTLVTVSS |
| SEQ ID NO 100 | VH | QVQLVQSGAEVKKPGASVKVSCKASGYTFTSSYINWVRQAPGQGLEVVMGTINPVSGNT<br>SYAQKFQGRVTMTRDTSISTAYMELSSLRSEDTAVYYCARGGWFDYWGQGTLVTVSS |
| SEQ ID NO 101 | VH | QVQLVQSGAEVKKPGASVKVSCKASGYTFTSSYINWVRQAPGQGLEVVMGTINPVSGNT<br>SYAQKFQGRVTMTRDTSISTAYMELSSLRSEDTAVYYCARGGWFDYWGQGTLVTVSS |
| SEQ ID NO 102 | VH | QVQLVQSGAEVKKPGASVKVSCKASGYTFTSSYINWVRQAPGQGLEVVMGTINPVSGNT<br>SYAQKFQGRVTMTRDTSISTAYMELSSLRSEDTAVYYCARGGWFDYWGQGTLVTVSS |
| SEQ ID NO 103 | VH | QVQLVQSGAEVKKPGASVKVSCKASGYTFTSSYINWVRQAPGQGLEVVMGMINAPIGTTR<br>YAQKFQGRVTMTRDTSISTAYMELSSLRSEDTAVYYCARGGVVFDYWGQGTLVTVSS |
| SEQ ID NO 104 | VH | QVQLVQSGAEVKKPGASVKVSCKASGYTFTSSYINWVRQAPGQGLEVVMGQINAASGMT<br>RYAQKFQGRVTMTRDTSISTAYMELSSLRSEDTAVYYCARGGVVFDYWGQGTLVTVSS |
| SEQ ID NO 105 | VH | QVQLVQSGAEVKKPGASVKVSCKASGYTFTSSYINWVRQAPGQGLEVVMGMINAPIGTTR<br>YAQKFQGRVTMTRDTSISTAYMELSSLRSEDTAVYYCARGGVVFDYWGQGTLVTVSS |
| SEQ ID NO 106 | VH | QVQLVQSGAEVKKPGASVKVSCKASGYTFTSSYINWVRQAPGQGLEVVMGTINPVSGNT<br>RYAQKFQGRVTMTRDTSISTAYMELSSLRSEDTAVYYCARGGVVFDYWGQGTLVTVSS |
| SEQ ID NO 107 | VH | QVQLVQSGAEVKKPGASVKVSCKASGYTFTSSYINWVRQAPGQGLEVVMGTINPVSGST<br>SYAQKFQGRVTMTRDTSISTAYMELSSLRSEDTAVYYCARGGWFDYWGQGTLVTVSS |

TABLE 1-continued sequence listing

| SEQ ID NO | Ab region | Sequence |
|---|---|---|
| SEQ ID NO 108 | VH | QVQLVQSGAEVKKPGASVKVSCKASGYTFTSSYINWVRQAPGQGLEVVMGQINAASGMT<br>RYAQKFQGRVTMTRDTSISTAYMELSSLRSEDTAVYYCARGGVVFDYWGQGTLVTVSS |
| SEQ ID NO 109 | VH | QVQLVQSGAEVKKPGASVKVSCKASGYTFTSSYINWVRQAPGQGLEVVMGNINAAAGITL<br>YAQKFQGRVTMTRDTSISTAYMELSSLRSEDTAVYYCARGGVVFDYWGQGTLVTVSS |
| SEQ ID NO 110 | VH | QVQLVQSGAEVKKPGASVKVSCKASGYTFTSSYINWVRQAPGQGLEVVMGTINPPTGGT<br>YYAQKFQGRVTMTRDTSISTAYMELSSLRSEDTAVYYCARGGWFDYWGQGTLVTVSS |
| SEQ ID NO 111 | VH | QVQLVQSGAEVKKPGASVKVSCKASGYTFTSSYINWVRQAPGQGLEVVMGGINPPAGTT<br>SYAQKFQGRVTMTRDTSISTAYMELSSLRSEDTAVYYCARGGWFDYWGQGTLVTVSS |
| SEQ ID NO 112 | VH | QVQLVQSGAEVKKPGASVKVSCKASGYTFTSSYINWVRQAPGQGLEVVMGNINPATGHA<br>DYAQKFQGRVTMTRDTSISTAYMELSSLRSEDTAVYYCARGGVVFDYWGQGTLVTVSS |
| SEQ ID NO 113 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCCAGGCTTGGACTTCT<br>AAGATGGCTGGTGTGTTTGGCGGCGGCACGAAGTTAACCGTTCTTGGCCAG |
| SEQ ID NO 114 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCTCTTCTTATACTCGTA<br>TGGGTCATCCTGTGTTTGGCGGCGGCACGAAGTTAACCGTTCTTGGCCAG |
| SEQ ID NO 115 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGCTACTTATGGTAAG<br>GGTGTTACTCCTCCTGTGTTTGGCGGCGGCACGAAGTTAACCGTTCTTGGCCAG |
| SEQ ID NO 116 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 117 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCCAGGCTTGGACTTCT<br>AAGATGGCTGGTGTGTTTGGCGGCGGCACGAAGTTAACCGTTCTTGGCCAG |
| SEQ ID NO 118 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCCAGGCTTGGACTTCT<br>AAGATGGCTGGTGTGTTTGGCGGCGGCACGAAGTTAACCGTTCTTGGCCAG |
| SEQ ID NO 119 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 120 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |

TABLE 1-continued sequence listing

| SEQ ID NO | Ab region | Sequence |
|---|---|---|
| SEQ ID NO 121 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 122 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 123 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 124 | DNA VL | GATATCGCACTGACCCAGCCAGCTTCAGTGAGCGGCTCACCAGGTCAGAGCATTACC<br>ATCTCGTGTACTGGTACTAGCAGCGATGTTGGTTCTTATAATTATGTGAATTGGTACCA<br>GCAGCATCCCGGGAAGGCGCCGAAACTTATGATTTATGGTGTTTCTAAGCGTCCCTC<br>AGGCGTGAGCAACCGTTTTAGCGGATCCAAAAGCGGCAACACCGCGAGCCTGACCAT<br>TAGCGGCCTGCAAGCGGAAGACGAAGCGGATTATTATTGCGGTACTTTTGCTGGTGG<br>TTCTTATTATGGTGTGTTTGGCGGCGGCACGAAGTTAACCGTTCTTGGCCAG |
| SEQ ID NO 125 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 126 | DNA VL | GATATCGCACTGACCCAGCCAGCTTCAGTGAGCGGCTCACCAGGTCAGAGCATTACC<br>ATCTCGTGTACGGGTACTAGCAGCGATGTTGGTTCTTATAATTATGTGAATTGGTACC<br>AGCAGCATCCCGGGAAGGCGCCGAAACTTATGATTTATGGTGTTTCTAAGCGTCCCT<br>CAGGCGTGAGCAACCGTTTTAGCGGATCCAAAAGCGGCAACACCGCGAGCCTGACC<br>ATTAGCGGCCTGCAAGCGGAAGACGAAGCGGATTATTATTGCGGTACTTTTGCTGGT<br>GGTTCTTATTATGGTGTGTTTGGCGGCGGCACGAAGTTAACCGTTCTTGGCCAG |
| SEQ ID NO 127 | DNA VH | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCACTATCAATCCGGTTTCTGGCAATA<br>CGTCTTACGCGCAGAAGTTTCAGGGCCGGGTGACCATGACCCGTGATACCAGCATTA<br>GCACCGCGTATATGGAACTGAGCAGCCTGCGTAGCGAAGATACGGCCGTGTATTATT<br>GCGCGCGTGGTGGTTGGTTTGATTATTGGGGCCAAGGCACCCTGGTGACGGTTAGCT<br>CA |
| SEQ ID NO 128 | DNA VH | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCACTATCAATCCGGTTTCTGGCAATA<br>CGTCTTACGCGCAGAAGTTTCAGGGCCGGGTGACCATGACCCGTGATACCAGCATTA<br>GCACCGCGTATATGGAACTGAGCAGCCTGCGTAGCGAAGATACGGCCGTGTATTATT<br>GCGCGCGTGGTGGTTGGTTTGATTATTGGGGCCAAGGCACCCTGGTGACGGTTAGCT<br>CA |
| SEQ ID NO 129 | DNA VH | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCACTATCAATCCGGTTTCTGGCAATA<br>CGTCTTACGCGCAGAAGTTTCAGGGCCGGGTGACCATGACCCGTGATACCAGCATTA<br>GCACCGCGTATATGGAACTGAGCAGCCTGCGTAGCGAAGATACGGCCGTGTATTATT<br>GCGCGCGTGGTGGTTGGTTTGATTATTGGGGCCAAGGCACCCTGGTGACGGTTAGCT<br>CA |
| SEQ ID NO 130 | DNA VH | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCACTATCAATCCGGTTTCTGGCAATA<br>CGTCTTACGCGCAGAAGTTTCAGGGCCGGGTGACCATGACCCGTGATACCAGCATTA<br>GCACCGCGTATATGGAACTGAGCAGCCTGCGTAGCGAAGATACGGCCGTGTATTATT<br>GCGCGCGTGGTGGTTGGTTTGATTATTGGGGCCAAGGCACCCTGGTGACGGTTAGCT<br>CA |

TABLE 1-continued sequence listing

| SEQ ID NO | Ab region | Sequence |
|---|---|---|
| SEQ ID NO 131 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCATGATTAATGCTCCTATTGGTACTACTCGTTATGCTCAGAAGTTTCAGGGTCGGGTGACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 132 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCCAGATTAATGCTGCTTCTGGTATGACTCGTTATGCTCAGAAGTTTCAGGGTCGGGTGACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 133 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCATGATTAATGCTCCTATTGGTACTACTCGTTATGCTCAGAAGTTTCAGGGTCGGGTGACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 134 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCACTATCAATCCGGTTTCTGGCAATACGCGTTACGCGCAGAAGTTTCAGGGCCGGGTGACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 135 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCACTATCAATCCGGTTTCTGGCTCTACGTCTTACGCGCAGAAGTTTCAGGGCCGGGTGACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 136 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCCAGATTAATGCTGCTTCTGGTATGACTCGTTATGCTCAGAAGTTTCAGGGTCGGGTCACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 137 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCAATATTAATGCTGCTGCTGGTATTACTCTTTATGCTCAGAAGTTTCAGGGTCGGGTCACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 138 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCACTATTAATCCTCCTACTGGAGGTACTTATTATGCTCAGAAGTTTCAGGGTCGGGTGACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 139 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCGGTATTAATCCTCCTGCTGGTACTACTTCTTATGCTCAGAAGTTTCAGGGTCGGGTCACCATGACCCGTGATACCAGCATTAGCACCGCGTATATGGAACTGAGCAGCCTGCGTAGCGAAGATACGGCCGTGTATTATTGCGCGCGTGGTGGTTGGTTTGATTATTGGGGCCAAGGCACCCTGGTGACGGTTAGCTCA |
| SEQ ID NO 140 | DNA VH | CAGGTGCAATTGGTTCAGAGCGGCGCGGAAGTGAAAAAACCGGGCGCGAGCGTGAAAGTGAGCTGCAAAGCCTCCGGATATACCTTTACTTCTTCTTATATTAATTGGGTCCGCCAAGCCCCTGGGCAGGGTCTCGAGTGGATGGGCAATATTAATCCTGCTACTGGTCATG |

TABLE 1-continued sequence listing

| SEQ ID NO | Ab region | Sequence |
|---|---|---|
| | | CTGATTATGCTCAGAAGTTTCAGGGTCGGGTGACCATGACCCGTGATACCAGCATTA<br>GCACCGCGTATATGGAACTGAGCAGCCTGCGTAGCGAAGATACGGCCGTGTATTAT<br>TGCGCGCGTGGTGGTTGGTTTGATTATTGGGGCCAAGGCACCCTGGTGACGGTTAGCT<br>CA |
| SEQ ID NO 141 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 142 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 143 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 144 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 145 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 146 | Heavy Chain | QVQLVQSGAEVKKPGASVKVSCKASGYTFTSSYINVVRQAPGQGLEVVMGTINPVSGST<br>SYAQKFQGRVTMTRDTSISTAYMELSRLRSDDTAVYYCARGGVVFDYWGQGTLVTVSSA<br>STKGPSVFPLAPSSKSTSGGTAALGCLVKDYFPEPVTVSVVNSGALTSGVHTFPAVLQSS<br>GLYSLSSVVTVPSSSLGTQTYICNVNHKPSNTKVDKRVEPKSCDKTHTCPPCPAPEAAGG<br>PSVFLFPPKPKDTLMISRTPEVTCVVVDVSHEDPEVKFNVVYVDGVEVHNAKTKPREEQY<br>NSTYRVVSVLTVLHQDVVLNGKEYKCKVSNKALPAPIEKTISKAKGQPREPQVYTLPPSRE<br>EMTKNQVSLTCLVKGFYPSDIAVEVVESNGQPENNYKTTPPVLDSDGSFFLYSKLTVDKSR<br>WQQGNVFSCSVMHEALHNHYTQKSLSLSPGK |
| SEQ ID NO 147 | Heavy Chain | QVQLVQSGAEVKKPGASVKVSCKASGYTFTSSYINVVRQAPGQGLEVVMGQINAASGMT<br>RYAQKFQGRVTMTRDTSISTAYMELSRLRSDDTAVYYCARGGVVFDYWGQGTLVTVSSA<br>STKGPSVFPLAPSSKSTSGGTAALGCLVKDYFPEPVTVSVVNSGALTSGVHTFPAVLQSS<br>GLYSLSSVVTVPSSSLGTQTYICNVNHKPSNTKVDKRVEPKSCDKTHTCPPCPAPEAAGG<br>PSVFLFPPKPKDTLMISRTPEVTCVVVDVSHEDPEVKFNVVYVDGVEVHNAKTKPREEQY<br>NSTYRVVSVLTVLHQDVVLNGKEYKCKVSNKALPAPIEKTISKAKGQPREPQVYTLPPSRE<br>EMTKNQVSLTCLVKGFYPSDIAVEVVESNGQPENNYKTTPPVLDSDGSFFLYSKLTVDKSR<br>WQQGNVFSCSVMHEALHNHYTQKSLSLSPGK |
| SEQ ID NO 148 | Heavy Chain | QVQLVQSGAEVKKPGASVKVSCKASGYTFTSSYINVVRQAPGQGLEVVMGNINAAAGITL<br>YAQKFQGRVTMTRDTSISTAYMELSRLRSDDTAVYYCARGGVVFDYWGQGTLVTVSSAS<br>TKGPSVFPLAPSSKSTSGGTAALGCLVKDYFPEPVTVSVVNSGALTSGVHTFPAVLQSSGL<br>YSLSSVVTVPSSSLGTQTYICNVNHKPSNTKVDKRVEPKSCDKTHTCPPCPAPEAAGGPS<br>VFLFPPKPKDTLMISRTPEVTCVVVDVSHEDPEVKFNVVYVDGVEVHNAKTKPREEQYNST<br>YRVVSVLTVLHQDWLNGKEYKCKVSNKALPAPIEKTISKAKGQPREPQVYTLPPSREEMT<br>KNQVSLTCLVKGFYPSDIAVEVVESNGQPENNYKTTPPVLDSDGSFFLYSKLTVDKSRWQ<br>QGNVFSCSVMHEALHNHYTQKSLSLSPGK |
| SEQ ID NO 149 | Heavy Chain | QVQLVQSGAEVKKPGASVKVSCKASGYTFTSSYINVVRQAPGQGLEVVMGGINPPAGTT<br>SYAQKFQGRVTMTRDTSISTAYMELSRLRSDDTAVYYCARGGVVFDYWGQGTLVTVSSA<br>STKGPSVFPLAPSSKSTSGGTAALGCLVKDYFPEPVTVSVVNSGALTSGVHTFPAVLQSS<br>GLYSLSSVVTVPSSSLGTQTYICNVNHKPSNTKVDKRVEPKSCDKTHTCPPCPAPEAAGG<br>PSVFLFPPKPKDTLMISRTPEVTCVVVDVSHEDPEVKFNVVYVDGVEVHNAKTKPREEQY<br>NSTYRVVSVLTVLHQDVVLNGKEYKCKVSNKALPAPIEKTISKAKGQPREPQVYTLPPSRE<br>EMTKNQVSLTCLVKGFYPSDIAVEVVESNGQPENNYKTTPPVLDSDGSFFLYSKLTVDKSR<br>WQQGNVFSCSVMHEALHNHYTQKSLSLSPGK |
| SEQ ID NO 150 | Heavy Chain | QVQLVQSGAEVKKPGASVKVSCKASGYTFTSSYINVVRQAPGQGLEVVMGNINPATGHA<br>DYAQKFQGRVTMTRDTSISTAYMELSRLRSDDTAVYYCARGGVVFDYWGQGTLVTVSSA<br>STKGPSVFPLAPSSKSTSGGTAALGCLVKDYFPEPVTVSVVNSGALTSGVHTFPAVLQSS<br>GLYSLSSVVTVPSSSLGTQTYICNVNHKPSNTKVDKRVEPKSCDKTHTCPPCPAPEAAGG<br>PSVFLFPPKPKDTLMISRTPEVTCVVVDVSHEDPEVKFNVVYVDGVEVHNAKTKPREEQY<br>NSTYRVVSVLTVLHQDVVLNGKEYKCKVSNKALPAPIEKTISKAKGQPREPQVYTLPPSRE<br>EMTKNQVSLTCLVKGFYPSDIAVEVVESNGQPENNYKTTPPVLDSDGSFFLYSKLTVDKSR<br>WQQGNVFSCSVMHEALHNHYTQKSLSLSPGK |

TABLE 1-continued sequence listing

| SEQ ID NO | Ab region | Sequence |
|---|---|---|
| SEQ ID NO 151 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 152 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 153 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 154 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 155 | Light Chain | QSALTQPASVSGSPGQSITISCTGTSSDVGSYNYVNVVYQQHPGKAPKLMIYGVSKRPSG<br>VSNRFSGSKSGNTASLTISGLQAEDEADYYCGTFAGGSYYGVFGGGTKLTVLGQPKAAP<br>SVTLFPPSSEELQANKATLVCLISDFYPGAVTVAVVKADSSPVKAGVETTTPSKQSNNKYA<br>ASSYLSLTPEQVVKSHRSYSCQVTHEGSTVEKTVAPTECS |
| SEQ ID NO 156 | Heavy Chain | QVQLVQSGAEVKKPGASVKVSCKASGYTFTSSYINVVRQAPGQGLEVVMGTINPVSGST<br>SYAQKFQGRVTMTRDTSISTAYMELSRLRSDDTAVYYCARGGVVFDYWGQGTLVTVSSA<br>STKGPSVFPLAPCSRSTSESTAALGCLVKDYFPEPVTVSWNSGALTSGVHTFPAVLQSSG<br>LYSLSSVVTVPSSNFGTQTYTCNVDHKPSNTKVDKTVERKCCVECPPCPAPPVAGPSVFL<br>FPPKPKDTLMISRTPEVTCVVVDVSHEDPEVQFNVVYVDGVEVHNAKTKPREEQFNSTFR<br>VVSVLTVVHQDVVLNGKEYKCKVSNKGLPAPIEKTISKTKGQPREPQVYTLPPSREEMTKN<br>QVSLTCLVKGFYPSDIAVEWESNGQPENNYKTTPPMLDSDGSFFLYSKLTVDKSRWQQG<br>NVFSCSVMHEALHNHYTQKSLSLSPGK |
| SEQ ID NO 157 | Heavy Chain | QVQLVQSGAEVKKPGASVKVSCKASGYTFTSSYINVVRQAPGQGLEVVMGQINAASGMT<br>RYAQKFQGRVTMTRDTSISTAYMELSRLRSDDTAVYYCARGGVVFDYWGQGTLVTVSSA<br>STKGPSVFPLAPCSRSTSESTAALGCLVKDYFPEPVTVSWNSGALTSGVHTFPAVLQSSG<br>LYSLSSVVTVPSSNFGTQTYTCNVDHKPSNTKVDKTVERKCCVECPPCPAPPVAGPSVFL<br>FPPKPKDTLMISRTPEVTCVVVDVSHEDPEVQFNVVYVDGVEVHNAKTKPREEQFNSTFR<br>VVSVLTVVHQDVVLNGKEYKCKVSNKGLPAPIEKTISKTKGQPREPQVYTLPPSREEMTKN<br>QVSLTCLVKGFYPSDIAVEWESNGQPENNYKTTPPMLDSDGSFFLYSKLTVDKSRWQQG<br>NVFSCSVMHEALHNHYTQKSLSLSPGK |
| SEQ ID NO 158 | Heavy Chain | QVQLVQSGAEVKKPGASVKVSCKASGYTFTSSYINVVRQAPGQGLEVVMGNINAAAGITL<br>YAQKFQGRVTMTRDTSISTAYMELSRLRSDDTAVYYCARGGVVFDYWGQGTLVTVSSAS<br>TKGPSVFPLAPCSRSTSESTAALGCLVKDYFPEPVTVSVVNSGALTSGVHTFPAVLQSSGL<br>YSLSSVVTVPSSNFGTQTYTCNVDHKPSNTKVDKTVERKCCVECPPCPAPPVAGPSVFLF<br>PPKPKDTLMISRTPEVTCVVVDVSHEDPEVQFNVVYVDGVEVHNAKTKPREEQFNSTFRV<br>VSVLTVVHQDVVLNGKEYKCKVSNKGLPAPIEKTISKTKGQPREPQVYTLPPSREEMTKNQ<br>VSLTCLVKGFYPSDIAVEWESNGQPENNYKTTPPMLDSDGSFFLYSKLTVDKSRWQQGN<br>VFSCSVMHEALHNHYTQKSLSLSPGK |
| SEQ ID NO 159 | Heavy Chain | QVQLVQSGAEVKKPGASVKVSCKASGYTFTSSYINVVRQAPGQGLEVVMGGINPAGTT<br>SYAQKFQGRVTMTRDTSISTAYMELSRLRSDDTAVYYCARGGVVFDYWGQGTLVTVSSA<br>STKGPSVFPLAPCSRSTSESTAALGCLVKDYFPEPVTVSWNSGALTSGVHTFPAVLQSSG<br>LYSLSSVVTVPSSNFGTQTYTCNVDHKPSNTKVDKTVERKCCVECPPCPAPPVAGPSVFL<br>FPPKPKDTLMISRTPEVTCVVVDVSHEDPEVQFNVVYVDGVEVHNAKTKPREEQFNSTFR<br>VVSVLTVVHQDVVLNGKEYKCKVSNKGLPAPIEKTISKTKGQPREPQVYTLPPSREEMTKN<br>QVSLTCLVKGFYPSDIAVEWESNGQPENNYKTTPPMLDSDGSFFLYSKLTVDKSRWQQG<br>NVFSCSVMHEALHNHYTQKSLSLSPGK |
| SEQ ID NO 160 | Heavy Chain | QVQLVQSGAEVKKPGASVKVSCKASGYTFTSSYINVVRQAPGQGLEVVMGNINPATGHA<br>DYAQKFQGRVTMTRDTSISTAYMELSRLRSDDTAVYYCARGGVVFDYWGQGTLVTVSSA<br>STKGPSVFPLAPCSRSTSESTAALGCLVKDYFPEPVTVSWNSGALTSGVHTFPAVLQSSG<br>LYSLSSVVTVPSSNFGTQTYTCNVDHKPSNTKVDKTVERKCCVECPPCPAPPVAGPSVFL<br>FPPKPKDTLMISRTPEVTCVVVDVSHEDPEVQFNVVYVDGVEVHNAKTKPREEQFNSTFR<br>VVSVLTVVHQDVVLNGKEYKCKVSNKGLPAPIEKTISKTKGQPREPQVYTLPPSREEMTKN<br>QVSLTCLVKGFYPSDIAVEWESNGQPENNYKTTPPMLDSDGSFFLYSKLTVDKSRWQQG<br>NVFSCSVMHEALHNHYTQKSLSLSPGK |
| SEQ ID NO 161 | DNA Light Chain | CAGAGCGCCCTGACCCAGCCCGCCAGCGTGTCCGGCAGCCCAGGCCAGTCTATCAC<br>AATCAGCTGCACCGGCACCTCCAGCGACGTGGGCAGCTACAACTACGTGAACTGGTA<br>TCAGCAGCACCCCGGCAAGGCCCCCAAGCTGATGATCTACGGCGTGAGCAAGAGGC<br>CCAGCGGCGTGTCCAACAGGTTCAGCGGCAGCAAGAGCGGCAACACCGCCAGCCTG<br>ACAATCAGTGGGCTGCAGGCTGAGGACGAGGCCGACTACTACTGCGGCACCTTTGC |

TABLE 1-continued sequence listing

| SEQ ID NO | Ab region | Sequence |
|---|---|---|
| | | CGGCGGATCATACTACGGCGTGTTCGGCGGAGGGACCAAGCTGACCGTGCTGGGCC<br>AGCCTAAGGCTGCCCCCAGCGTGACCCTGTTCCCCCCCAGCAGCGAGGAGCTGCAG<br>GCCAACAAGGCCACCCTGGTGTGCCTGATCAGCGACTTCTACCCAGGCGCCGTGAC<br>CGTGGCCTGGAAGGCCGACAGCAGCCCCGTGAAGGCCGGCGTGGAGACCACCACC<br>CCCAGCAAGCAGAGCAACAACAAGTACGCCGCCAGCAGCTACCTGAGCCTGACCCC<br>CGAGCAGTGGAAGAGCCACAGGTCCTACAGCTGCCAGGTGACCCACGAGGGCAGCA<br>CCGTGGAAAAGACCGTGGCCCCAACCGAGTGCAGC |
| SEQ ID NO 162 | DNA Light Chain | CAGAGCGCCCTGACCCAGCCCGCCAGCGTGTCCGGCAGCCCAGGCCAGTCTATCAC<br>AATCAGCTGCACCGGCACCTCCAGCGACGTGGGCAGCTACAACTACGTGAACTGGTA<br>TCAGCAGCACCCCGGCAAGGCCCCCAAGCTGATGATCTACGGCGTGAGCAAGAGGC<br>CCAGCGGCGTGTCCAACAGGTTCAGCGGCAGCAAGAGCGGCAACACCGCCAGCCTG<br>ACAATCAGTGGGCTGCAGGCTGAGGACGAGGCCGACTACTACTGCGGCACCTTTGC<br>CGGCGGATCATACTACGGCGTGTTCGGCGGAGGGACCAAGCTGACCGTGCTGGGCC<br>AGCCTAAGGCTGCCCCCAGCGTGACCCTGTTCCCCCCCAGCAGCGAGGAGCTGCAG<br>GCCAACAAGGCCACCCTGGTGTGCCTGATCAGCGACTTCTACCCAGGCGCCGTGAC<br>CGTGGCCTGGAAGGCCGACAGCAGCCCCGTGAAGGCCGGCGTGGAGACCACCACC<br>CCCAGCAAGCAGAGCAACAACAAGTACGCCGCCAGCAGCTACCTGAGCCTGACCCC<br>CGAGCAGTGGAAGAGCCACAGGTCCTACAGCTGCCAGGTGACCCACGAGGGCAGCA<br>CCGTGGAAAAGACCGTGGCCCCAACCGAGTGCAGC |
| SEQ ID NO 163 | DNA Light Chain | CAGAGCGCACTGACCCAGCCAGCTTCAGTGAGCGGCTCACCAGGTCAGAGCATTAC<br>CATCTCGTGTACGGGTACTAGCAGCGATGTTGGTTCTTATAATTATGTGAATTGGTAC<br>CAGCAGCATCCCGGGAAGGCGCCGAAACTTATGATTTATGGTGTTTCTAAGCGTCCC<br>TCAGGCGTGAGCAACCGTTTTAGCGGATCCAAAAGCGGCAACACCGCGAGCCTGAC<br>CATTAGCGGCCTGCAAGCGGAAGACGAAGCGGATTATTATTGCGGTACTTTTGCTGG<br>TGGTTCTTATTATGGTGTGTTTGGCGGCGGCACGAAGTTAACCGTCCTAGGTCAGCC<br>CAAGGCTGCCCCCTCGGTCACTCTGTTCCCGCCCTCCTCTGAGGAGCTTCAAGCCAA<br>CAAGGCCACACTGGTGTGTCTCATAAGTGACTTCTACCCGGGAGCCGTGACAGTGGC<br>CTGGAAGGCAGATAGCAGCCCCGTCAAGGCGGGAGTGGAGACCACCACACCCTCCA<br>AACAAAGCAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACCGTGGAG<br>AAGACAGTGGCCCCCTACAGAATGTTCA |
| SEQ ID NO 164 | DNA Light Chain | CAGAGCGCACTGACCCAGCCAGCTTCAGTGAGCGGCTCACCAGGTCAGAGCATTAC<br>CATCTCGTGTACGGGTACTAGCAGCGATGTTGGTTCTTATAATTATGTGAATTGGTAC<br>CAGCAGCATCCCGGGAAGGCGCCGAAACTTATGATTTATGGTGTTTCTAAGCGTCCC<br>TCAGGCGTGAGCAACCGTTTTAGCGGATCCAAAAGCGGCAACACCGCGAGCCTGAC<br>CATTAGCGGCCTGCAAGCGGAAGACGAAGCGGATTATTATTGCGGTACTTTTGCTGG<br>TGGTTCTTATTATGGTGTGTTTGGCGGCGGCACGAAGTTAACCGTCCTAGGTCAGCC<br>CAAGGCTGCCCCCTCGGTCACTCTGTTCCCGCCCTCCTCTGAGGAGCTTCAAGCCAA<br>CAAGGCCACACTGGTGTGTCTCATAAGTGACTTCTACCCGGGAGCCGTGACAGTGGC<br>CTGGAAGGCAGATAGCAGCCCCGTCAAGGCGGGAGTGGAGACCACCACACCCTCCA<br>AACAAAGCAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACCGTGGAG<br>AAGACAGTGGCCCCCTACAGAATGTTCA |
| SEQ ID NO 165 | DNA Light Chain | CAGAGCGCACTGACCCAGCCAGCTTCAGTGAGCGGCTCACCAGGTCAGAGCATTAC<br>CATCTCGTGTACGGGTACTAGCAGCGATGTTGGTTCTTATAATTATGTGAATTGGTAC<br>CAGCAGCATCCCGGGAAGGCGCCGAAACTTATGATTTATGGTGTTTCTAAGCGTCCC<br>TCAGGCGTGAGCAACCGTTTTAGCGGATCCAAAAGCGGCAACACCGCGAGCCTGAC<br>CATTAGCGGCCTGCAAGCGGAAGACGAAGCGGATTATTATTGCGGTACTTTTGCTGG<br>TGGTTCTTATTATGGTGTGTTTGGCGGCGGCACGAAGTTAACCGTCCTAGGTCAGCC<br>CAAGGCTGCCCCCTCGGTCACTCTGTTCCCGCCCTCCTCTGAGGAGCTTCAAGCCAA<br>CAAGGCCACACTGGTGTGTCTCATAAGTGACTTCTACCCGGGAGCCGTGACAGTGGC<br>CTGGAAGGCAGATAGCAGCCCCGTCAAGGCGGGAGTGGAGACCACCACACCCTCCA<br>AACAAAGCAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACCGTGGAG<br>AAGACAGTGGCCCCCTACAGAATGTTCA |
| SEQ ID NO 166 | DNA Heavy Chain | CAGGTGCAGCTGGTGCAGAGCGGAGCTGAGGTGAAGAAGCCAGGCGCCAGCGTCAA<br>GGTGTCCTGCAAGGCCAGCGGCTACACCTTCACCAGCAGCTACATCAACTGGGTCCG<br>CCAGGCTCCTGGGCAGGGACTGGAGTGGATGGGCACCATCAACCCCGTGTCCGGCA<br>GCACCAGCTACGCCCAGAAGTTCCAGGGCAGAGTCACCATGACCAGGGACACCAGC<br>ATCAGCACCGCCTACATGGAGCTGTCCAGGCTGAGAAGCGACGACACCGCCGTGTA<br>CTACTGCGCCAGGGCGGCTGGTTCGACTACTGGGGCCAGGGCACCCTGGTGACCG<br>TGTCCTCAGCTAGCACCAAGGGCCCCAGCGTGTTCCCCCTGGCCCCCAGCAGCAAG<br>AGCACCTCCGGCGGCACAGCCGCCCTGGGCTGCCTGGTGAAGGACTACTTCCCCGA<br>GCCCGTGACCGTGTCCTGGAACAGCGGAGCCCTGACCAGCGGCGTGCACACCTTCC<br>CGGCCGTGCTGCAGAGCAGCGGCCTGTACAGCCTGTCCAGCGTGGTGACAGTGCCC<br>AGCAGCAGCCTGGGCACCCAGACCTACATCTGCAACGTGAACCACAAGCCCAGCAAC<br>ACCAAGGTGGACAAGAGAGTGGAGCCCAAGAGCTGCGACAAGACCCACACCTGCCC<br>CCCCTGCCCAGCCCCCGAAGCTGCAGGCGGCCCTTCCGTGTTCCTGTTCCCCCCA<br>AGCCCAAGGACACCCTGATGATCAGCAGGACCCCCGAGGTGACCTGCGTGGTGGTG<br>GACGTGAGCCACGAGGACCCAGAGGTGAAGTTCAACTGGTACGTGGACGGCGTGGA |

TABLE 1-continued sequence listing

| SEQ ID NO | Ab region | Sequence |
|---|---|---|
| | | GGTGCACAACGCCAAGACCAAGCCCAGAGAGGAGCAGTACAACAGCACCTACAGGG<br>TGGTGTCCGTGCTGACCGTGCTGCACCAGGACTGGCTGAACGGCAAGAATACAAGT<br>GCAAGGTCTCCAACAAGGCCCTGCCTGCCCCCATCGAAAAGACCATCAGCAAGGCCA<br>AGGGCCAGCCACGGGAGCCCCAGGTGTACACCCTGCCCCCTTCTCGGGAGGAGATG<br>ACCAAGAACCAGGTGTCCCTGACCTGTCTGGTGAAGGGCTTCTACCCCAGCGACATC<br>GCCGTGGAGTGGGAGAGCAACGGCCAGCCCGAGAACAACTACAAGACCACCCCCCC<br>AGTGCTGGACAGCGACGGCAGCTTCTTCCTGTACAGCAAGCTGACCGTGGACAAGAG<br>CAGGTGGCAGCAGGGCAACGTGTTCAGCTGCAGCGTGATGCACGAGGCCCTGCACA<br>ACCACTACACCCAGAAGAGCCTGAGCCTGTCACCCGGCAAG |
| SEQ ID NO 167 | DNA Heavy Chain | CAGGTGCAGCTGGTGCAGAGCGGAGCTGAGGTGAAGAAGCCAGGCGCCAGCGTCAA<br>GGTGTCCTGCAAGGCCAGCGGCTACACCTTCACCAGCAGCTACATCAACTGGGTGCG<br>CCAGGCTCCAGGGCAGGGACTGGAGTGGATGGGCCAGATCAACGCCGCCAGCGGC<br>ATGACCAGATACGCCCAGAAGTTCCAGGGCAGAGTCACAATGACCAGGGACACCTCT<br>ATCAGCACCGCCTACATGGAGCTGTCCAGGCTGAGAAGCGACGACACCGCCGTGTA<br>CTACTGCGCAGGGCGGCTGGTTCGACTACTGGGGCCAGGGCACCCTGGTGACCG<br>TGTCCTCAGCTAGCACCAAGGGCCCCAGCGTGTTCCCCCTGGCCCCCAGCAGCAAG<br>AGCACCTCCGGCGGCACAGCCGCCCTGGGCTGCCTGGTGAAGGACTACTTCCCCGA<br>GCCCGTGACCGTGTCCTGGAACAGCGGAGCCCTGACCAGCGGCGTGCACACCTTCC<br>CCGCCGTGCTGCAGAGCAGCGGCCTGTACAGCCTGTCCAGCGTGGTGACAGTGCCC<br>AGCAGCAGCCTGGGCACCCAGACCTACATCTGCAACGTGAACCACAAGCCCAGCAAC<br>ACCAAGGTGGACAAGAGAGTGGAGCCCAAGAGCTGCGACAAGACCCACACCTGCCC<br>CCCCTGCCCAGCCCCCGAAGCTGCAGGCGGCCCTTCCGTGTTCCTGTTCCCCCCCA<br>AGCCCAAGGACACCCTGATGATCAGCAGGACCCCCGAGGTGACCTGCGTGGTGGTG<br>GACGTGAGCCACGAGGACCCAGAGGTGAAGTTCAACTGGTACGTGGACGGCGTGGA<br>GGTGCACAACGCCAAGACCAAGCCCAGAGAGGAGCAGTACAACAGCACCTACAGGG<br>TGGTGTCCGTGCTGACCGTGCTGCACCAGGACTGGCTGAACGGCAAGAATACAAGT<br>GCAAGGTCTCCAACAAGGCCCTGCCTGCCCCCATCGAAAAGACCATCAGCAAGGCCA<br>AGGGCCAGCCACGGGAGCCCCAGGTGTACACCCTGCCCCCTTCTCGGGAGGAGATG<br>ACCAAGAACCAGGTGTCCCTGACCTGTCTGGTGAAGGGCTTCTACCCCAGCGACATC<br>GCCGTGGAGTGGGAGAGCAACGGCCAGCCCGAGAACAACTACAAGACCACCCCCCC<br>AGTGCTGGACAGCGACGGCAGCTTCTTCCTGTACAGCAAGCTGACCGTGGACAAGAG<br>CAGGTGGCAGCAGGGCAACGTGTTCAGCTGCAGCGTGATGCACGAGGCCCTGCACA<br>ACCACTACACCCAGAAGAGCCTGAGCCTGTCACCCGGCAAG |
| SEQ ID NO 168 | DNA Heavy Chain | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCAATATTAATGCTGCTGCTGGTATTA<br>CTCTTTATGCTCAGAAGTTTCAGGGTCGGGTCACCATGACCCGTGATACCAGCATTAG<br>CACCGCGTATATGGAACTGAGCCGCCTGCGTAGCGATGATACGGCCGTGTATTATTG<br>CGCGCGTGGTGGTTGGTTTGATTATTGGGGCCAAGGCACCCTGGTGACGGTTAGCTC<br>AGCCTCCACCAAGGGTCCATCGGTCTTCCCCCTGGCACCCTCCTCCAAGAGCACCTC<br>TGGGGGCACAGCGGCCCTGGGCTGCCTGGTCAAGGACTACTTCCCCGAACCGGTGA<br>CGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGC<br>TTGGGCACCCAGACCTACATCTGCAACGTGAATCACAAGCCCAGCAACACCAAGGTG<br>GACAAGAGAGTTGAGCCCAAATCTTGTGACAAAACTCACACATGCCCACCGTGCCCA<br>GCACCTGAAGCAGCGGGGGGACCGTCAGTCTTCCTCTTCCCCCCAAAACCCAAGGA<br>CACCCTCATGATCTCCCGGACCCCTGAGGTCACATGCGTGGTGGTGGACGTGAGCC<br>ACGAAGACCCTGAGGTCAAGTTCAACTGGTACGTGGACGGCGTGGAGGTGCATAATG<br>CCAAGACAAAGCCGCGGGAGGAGCAGTACAACAGCACGTACCGGGTGGTCAGCGTC<br>CTCACCGTCCTGCACCAGGACTGGCTGAATGGCAAGGAGTACAAGTGCAAGGTCTCC<br>AACAAAGCCCTCCCAGCCCCCATCGAGAAAACCATCTCCAAAGCCAAAGGGCAGCCC<br>CGAGAACCACAGGTGTACACCCTGCCCCCATCCCGGGAGGAGATGACCAAGAACCA<br>GGTCAGCCTGACCTGCCTGGTCAAAGGCTTCTATCCCAGCGACATCGCCGTGGAGTG<br>GGAGAGCAATGGGCAGCCGGAGAACAACTACAAGACCACGCCTCCCGTGCTGGACT<br>CCGACGGCTCCTTCTTCCTCTACAGCAAGCTCACCGTGGACAAGAGCAGGTGGCAGC<br>AGGGGAACGTCTTCTCATGCTCCGTGATGCATGAGGCTCTGCACAACCACTACACGC<br>AGAAGAGCCTCTCCCTGTCTCCGGGTAAA |
| SEQ ID NO 169 | DNA Heavy Chain | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCCGGTATTAATCCTCCTGCTGGTACTA<br>CTCTTTATGCTCAGAAGTTTCAGGGTCGGGTCACCATGACCCGTGATACCAGCATTAG<br>CACCGCGTATATGGAACTGAGCCGCCTGCGTAGCGATGATACGGCCGTGTATTATTG<br>CGCGCGTGGTGGTTGGTTTGATTATTGGGGCCAAGGCACCCTGGTGACGGTTAGCTC<br>AGCCTCCACCAAGGGTCCATCGGTCTTCCCCCTGGCACCCTCCTCCAAGAGCACCTC<br>TGGGGGCACAGCGGCCCTGGGCTGCCTGGTCAAGGACTACTTCCCCGAACCGGTGA<br>CGGTGTCGTGGAACTCAGGCGCCCTGACCAGCGGCGTGCACACCTTCCCGGCTGTC<br>CTACAGTCCTCAGGACTCTACTCCCTCAGCAGCGTGGTGACCGTGCCCTCCAGCAGC<br>TTGGGCACCCAGACCTACATCTGCAACGTGAATCACAAGCCCAGCAACACCAAGGTG<br>GACAAGAGAGTTGAGCCCAAATCTTGTGACAAAACTCACACATGCCCACCGTGCCCA<br>GCACCTGAAGCAGCGGGGGGACCGTCAGTCTTCCTCTTCCCCCCAAAACCCAAGGA<br>CACCCTCATGATCTCCCGGACCCCTGAGGTCACATGCGTGGTGGTGGACGTGAGCC<br>ACGAAGACCCTGAGGTCAAGTTCAACTGGTACGTGGACGGCGTGGAGGTGCATAATG |

TABLE 1-continued sequence listing

| SEQ ID NO | Ab region | Sequence |
|---|---|---|
| | | CCAAGACAAAGCCGCGGGAGGAGCAGTACAACAGCACGTACCGGGTGGTCAGCGTC<br>CTCACCGTCCTGCACCAGGACTGGCTGAATGGCAAGGAGTACAAGTGCAAGGTCTCC<br>AACAAAGCCCTCCCAGCCCCCATCGAGAAAACCATCTCCAAAGCCAAAGGGCAGCCC<br>CGAGAACCACAGGTGTACACCCTGCCCCCATCCCGGGAGGAGATGACCAAGAACCA<br>GGTCAGCCTGACCTGCCTGGTCAAAGGCTTCTATCCCAGCGACATCGCCGTGGAGTG<br>GGAGAGCAATGGGCAGCCGGAGAACAACTACAAGACCACGCCTCCCGTGCTGGACT<br>CCGACGGCTCCTTCTTCCTCTACAGCAAGCTCACCGTGGACAAGAGCAGGTGGCAGC<br>AGGGGAACGTCTTCTCATGCTCCGTGATGCATGAGGCTCTGCACAACCACTACACGC<br>AGAAGAGCCTCTCCCTGTCTCCGGGTAAA |
| SEQ ID NO 170 | DNA Heavy Chain | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTTATATTAATTGGGTCCGCC<br>AAGCCCCTGGGCAGGGTCTCGAGTGGATGGGCAATATTAATCCTGCTACTGGTCATG<br>CTGATTATGCTCAGAAGTTTCAGGGTCGGGTGACCATGACCCGTGATACCAGCATTA<br>GCACCGCGTATATGGAACTGAGCCGCCTGCGTAGCGATGATACGGCCGTGTATTATT<br>GCGCGCGTGGTGGTTGGTTTGATTATTGGGGCCAAGGCACCCTGGTGACGGTTAGCT<br>CAGCCTCCACCAAGGGTCCATCGGTCTTCCCCCTGGCACCCTCCTCCAAGAGCACCT<br>CTGGGGGCACAGCGGCCCTGGGCTGCCTGGTCAAGGACTACTTCCCCGAACCGGTG<br>ACGGTGTCGTGGAACTCAGGCGCCCTGACCAGCGGCGTGCACACCTTCCCGGCTGT<br>CCTACAGTCCTCAGGACTCTACTCCCTCAGCAGCGTGGTGACCGTGCCCTCCAGCAG<br>CTTGGGCACCCAGACCTACATCTGCAACGTGAATCACAAGCCCAGCAACACCAAGGT<br>GGACAAGAGAGTTGAGCCCAAATCTTGTGACAAAACTCACACATGCCCACCGTGCCC<br>AGCACCTGAAGCAGCGGGGGGACCGTCAGTCTTCCTCTTCCCCCCAAAACCCAAGGA<br>CACCCTCATGATCTCCCGGACCCCTGAGGTCACATGCGTGGTGGTGGACGTGAGCC<br>ACGAAGACCCTGAGGTCAAGTTCAACTGGTACGTGGACGGCGTGGAGGTGCATAATG<br>CCAAGACAAAGCCGCGGGAGGAGCAGTACAACAGCACGTACCGGGTGGTCAGCGTC<br>CTCACCGTCCTGCACCAGGACTGGCTGAATGGCAAGGAGTACAAGTGCAAGGTCTCC<br>AACAAAGCCCTCCCAGCCCCCATCGAGAAAACCATCTCCAAAGCCAAAGGGCAGCCC<br>CGAGAACCACAGGTGTACACCCTGCCCCCATCCCGGGAGGAGATGACCAAGAACCA<br>GGTCAGCCTGACCTGCCTGGTCAAAGGCTTCTATCCCAGCGACATCGCCGTGGAGTG<br>GGAGAGCAATGGGCAGCCGGAGAACAACTACAAGACCACGCCTCCCGTGCTGGACT<br>CCGACGGCTCCTTCTTCCTCTACAGCAAGCTCACCGTGGACAAGAGCAGGTGGCAGC<br>AGGGGAACGTCTTCTCATGCTCCGTGATGCATGAGGCTCTGCACAACCACTACACGC<br>AGAAGAGCCTCTCCCTGTCTCCGGGTAAA |
| SEQ ID NO 171 | DNA Light Chain | CAGAGCGCCCTGACCCAGCCCGCCAGCGTGTCCGGCAGCCCAGGCCAGTCTATCAC<br>AATCAGCTGCACCGGCACCTCCAGCGACGTGGGCAGCTACAACTACGTGAACTGGTA<br>TCAGCAGCACCCCGGCAAGGCCCCCAAGCTGATGATCTACGGCGTGAGCAAGAGGC<br>CCAGCGGCGTGTCCAACAGGTTCAGCGGCAGCAAGAGCGGCAACACCGCCAGCCTG<br>ACAATCAGTGGGCTGCAGGCTGAGGACGAGGCCGACTACTACTGCGGCACCTTTGC<br>CGGCGGATCATACTACGGCGTGTTCGGCGGAGGGACCAAGCTGACCGTGCTGGGCC<br>AGCCTAAGGCTGCCCCCAGCGTGACCCTGTTCCCCCCCAGCAGCGAGGAGCTGCAG<br>GCCAACAAGGCCACCCTGGTGTGCCTGATCAGCGACTTCTACCCAGGCGCCGTGAC<br>CGTGGCCTGGAAGGCCGACAGCAGCCCCGTGAAGGCCGGCGTGGAGACCACCACC<br>CCCAGCAAGCAGAGCAACAACAAGTACGCCGCCAGCAGCTACCTGAGCCTGACCCC<br>CGAGCAGTGGAAGAGCCACAGGTCCTACAGCTGCCAGGTGACCCACGAGGGCAGCA<br>CCGTGGAAAAGACCGTGGCCCCAACCGAGTGCAGC |
| SEQ ID NO 172 | DNA Light Chain | CAGAGCGCCCTGACCCAGCCCGCCAGCGTGTCCGGCAGCCCAGGCCAGTCTATCAC<br>AATCAGCTGCACCGGCACCTCCAGCGACGTGGGCAGCTACAACTACGTGAACTGGTA<br>TCAGCAGCACCCCGGCAAGGCCCCCAAGCTGATGATCTACGGCGTGAGCAAGAGGC<br>CCAGCGGCGTGTCCAACAGGTTCAGCGGCAGCAAGAGCGGCAACACCGCCAGCCTG<br>ACAATCAGTGGGCTGCAGGCTGAGGACGAGGCCGACTACTACTGCGGCACCTTTGC<br>CGGCGGATCATACTACGGCGTGTTCGGCGGAGGGACCAAGCTGACCGTGCTGGGCC<br>AGCCTAAGGCTGCCCCCAGCGTGACCCTGTTCCCCCCCAGCAGCGAGGAGCTGCAG<br>GCCAACAAGGCCACCCTGGTGTGCCTGATCAGCGACTTCTACCCAGGCGCCGTGAC<br>CGTGGCCTGGAAGGCCGACAGCAGCCCCGTGAAGGCCGGCGTGGAGACCACCACC<br>CCCAGCAAGCAGAGCAACAACAAGTACGCCGCCAGCAGCTACCTGAGCCTGACCCC<br>CGAGCAGTGGAAGAGCCACAGGTCCTACAGCTGCCAGGTGACCCACGAGGGCAGCA<br>CCGTGGAAAAGACCGTGGCCCCAACCGAGTGCAGC |
| SEQ ID NO 173 | DNA Light Chain | CAGAGCGCACTGACCCAGCCAGCTTCAGTGAGCGGCTCACCAGGTCAGAGCATTAC<br>CATCTCGTGTACGGGTACTAGCAGCGATGTTGGTTCTTATAATTATGTGAATTGGTAC<br>CAGCAGCATCCCGGGAAGGCGCCGAAACTTATGATTTATGGTGTTTCTAAGCGTCCC<br>TCAGGCGTGAGCAACCGTTTTAGCGGATCCAAAAGCGGCAACACCGCGAGCCTGAC<br>CATTAGCGGCCTGCAAGCGGAAGACGAAGCGGATTATTATTGCGGTACTTTTGCTGG<br>TGGTTCTTATTATGGTGTGTTTGGCGGCGGCACGAAGTTAACCGTCCTAGGTCAGCC<br>CAAGGCTGCCCCCTCGGTCACTCTGTTCCCGCCCTCCTCTGAGGAGCTTCAAGCCAA<br>CAAGGCCACACTGGTGTGTCTCATAAGTGACTTCTACCCGGGAGCCGTGACAGTGGC<br>CTGGAAGGCAGATAGCAGCCCCGTCAAGGCGGGAGTGGAGACCACCACACCCTCCA<br>AACAAAGCAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACCGTGGAG<br>AAGACAGTGGCCCCTACAGAATGTTCA |

TABLE 1-continued sequence listing

| SEQ ID NO | Ab region | Sequence |
|---|---|---|
| SEQ ID NO 174 | DNA Light Chain | CAGAGCGCACTGACCCAGCCAGCTTCAGTGAGCGGCTCACCAGGTCAGAGCATTAC<br>CATCTCGTGTACGGGTACTAGCAGCGATGTTGGTTCTTATAATTATGTGAATTGGTAC<br>CAGCAGCATCCCGGGAAGGCGCCGAAACTTATGATTTATGGTGTTTCTAAGCGTCCC<br>TCAGGCGTGAGCAACCGTTTTAGCGGATCCAAAAGCGGCAACACCGCGAGCCTGAC<br>CATTAGCGGCCTGCAAGCGGAAGACGAAGCGGATTATTATTGCGGTACTTTTGCTGG<br>TGGTTCTTATTATGGTGTGTTTGGCGGCGGCACGAAGTTAACCGTCCTAGGTCAGCC<br>CAAGGCTGCCCCCTCGGTCACTCTGTTCCCGCCCTCCTCTGAGGAGCTTCAAGCCAA<br>CAAGGCCACACTGGTGTGTCTCATAAGTGACTTCTACCCGGGAGCCGTGACAGTGGC<br>CTGGAAGGCAGATAGCAGCCCCGTCAAGGCGGGAGTGGAGACCACCACACCCTCCA<br>AACAAAGCAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACCGTGGAG<br>AAGACAGTGGCCCCTACAGAATGTTCA |
| SEQ ID NO 175 | DNA Light Chain | CAGAGCGCACTGACCCAGCCAGCTTCAGTGAGCGGCTCACCAGGTCAGAGCATTAC<br>CATCTCGTGTACGGGTACTAGCAGCGATGTTGGTTCTTATAATTATGTGAATTGGTAC<br>CAGCAGCATCCCGGGAAGGCGCGAAACTTATGATTTATGGTGTTTCTAAGCGTCCC<br>TCAGGCGTGAGCAACCGTTTTAGCGGATCCAAAAGCGGCAACACCGCGAGCCTGAC<br>CATTAGCGGCCTGCAAGCGGAAGACGAAGCGGATTATTATTGCGGTACTTTTGCTGG<br>TGGTTCTTATTATGGTGTGTTTGGCGGCGGCACGAAGTTAACCGTCCTAGGTCAGCC<br>CAAGGCTGCCCCCTCGGTCACTCTGTTCCCGCCCTCCTCTGAGGAGCTTCAAGCCAA<br>CAAGGCCACACTGGTGTGTCTCATAAGTGACTTCTACCCGGGAGCCGTGACAGTGGC<br>CTGGAAGGCAGATAGCAGCCCCGTCAAGGCGGGAGTGGAGACCACCACACCCTCCA<br>AACAAAGCAACAACAAGTACGCGGCCAGCAGCTATCTGAGCCTGACGCCTGAGCAGT<br>GGAAGTCCCACAGAAGCTACAGCTGCCAGGTCACGCATGAAGGGAGCACCGTGGAG<br>AAGACAGTGGCCCCTACAGAATGTTCA |
| SEQ ID NO 176 | DNA Heavy Chain | CAGGTGCAGCTGGTGCAGAGCGGAGCTGAGGTGAAGAAGCCAGGCGCCAGCGTCAA<br>GGTGTCCTGCAAGGCCAGCGGCTACACCTTCACCAGCAGCTACATCAACTGGGTCCG<br>CCAGGCTCCTGGGCAGGGACTGGAGTGGATGGCACCATCAACCCCGTGTCCGGCA<br>GCACCAGCTACGCCCAGAAGTTCCAGGGCAGAGTCACCATGACCAGGGACACCAGC<br>ATCAGCACCGCCTACATGGAGCTGTCCAGGCTGAGAAGCGACGACACCGCCGTGTA<br>CTACTGCGCCAGGGGCGGCTGGTTCGACTACTGGGGCCAGGGCACCCTGGTGACCG<br>TGTCCTCAGCTAGCACCAAGGGCCCCAGCGTGTTCCCCCTGGCCCCCTGCAGCAGA<br>AGCACCAGCGAGAGCACAGCCGCCCTGGGCTGCCTGGTGAAGGACTACTTCCCCGA<br>GCCAGTGACCGTGTCCTGGAACAGCGGAGCCCTGACCAGCGGCGTGCACACCTTCC<br>CCGCCGTGCTGCAGAGCAGCGGCCTGTACAGCCTGTCCAGCGTGGTGACCGTGCCC<br>AGCAGCAACTTCGGCACCCAGACCTACACCTGCAACGTGGACCACAAGCCCAGCAAC<br>ACCAAGGTGGACAAGACCGTGGAGAGGAAGTGCTGCGTGGAGTGCCCCCCCTGCCC<br>AGCCCCCCCAGTGGCCGGACCCTCCGTGTTCCTGTTCCCCCCCAAGCCCAAGGACA<br>CCCTGATGATCAGCAGGACCCCCGAGGTGACCTGCGTGGTGGTGGACGTGAGCCAC<br>GAGGACCCAGAGGTGCAGTTCAACTGGTACGTGGACGGCGTGGAGGTGCACAACGC<br>CAAGACCAAGCCCAGAGAGGAACAGTTTAACAGCACCTTCAGGGTGGTGTCCGTGCT<br>GACCGTGGTGCACCAGGACTGGCTGAACGGCAAAGAGTACAAGTGCAAGGTCTCCA<br>ACAAGGGCCTGCCAGCCCCCATCGAGAAAACCATCAGCAAGACCAAGGGCCAGCCA<br>CGGGAGCCCCAGGTGTACACCCTGCCCCCCAGCCGGGAGGAAATGACCAAGAACCA<br>GGTGTCCCTGACCTGTCTGGTGAAGGGCTTCTACCCCAGCGACATCGCCGTGGAGT<br>GGGAGAGCAACGGCCAGCCCGAGAACAACTACAAGACCACCCCCCCCATGCTGGAC<br>AGCGACGGCAGCTTCTTCCTGTACAGCAAGCTGACAGTGGACAAGAGCAGGTGGCA<br>GCAGGGCAACGTGTTCAGCTGCAGCGTGATGCACGAGGCCCTGCACAACCACTACA<br>CCCAGAAGAGCCTGAGCCTGTCCCCCGGCAAG |
| SEQ ID NO 177 | DNA Heavy Chain | CAGGTGCAGCTGGTGCAGAGCGGAGCTGAGGTGAAGAAGCCAGGCGCCAGCGTCAA<br>GGTGTCCTGCAAGGCCAGCGGCTACACCTTCACCAGCAGCTACATCAACTGGGTGCG<br>CCAGGCTCCAGGGCAGGGACTGGAGTGGATGGGCCAGATCAACGCCGCCAGCGGC<br>ATGACCAGATACGCCCAGAAGTTCCAGGGCAGAGTCACAATGACCAGGGACACCTCT<br>ATCAGCACCGCCTACATGGAGCTGTCCAGGCTGAGAAGCGACGACACCGCCGTGTA<br>CTACTGCGCCAGGGGCGGCTGGTTCGACTACTGGGGCCAGGGCACCCTGGTGACCG<br>TGTCCTCAGCTAGCACCAAGGGCCCCAGCGTGTTCCCCCTGGCCCCCTGCAGCAGA<br>AGCACCAGCGAGAGCACAGCCGCCCTGGGCTGCCTGGTGAAGGACTACTTCCCCGA<br>GCCAGTGACCGTGTCCTGGAACAGCGGAGCCCTGACCAGCGGCGTGCACACCTTCC<br>CCGCCGTGCTGCAGAGCAGCGGCCTGTACAGCCTGTCCAGCGTGGTGACCGTGCCC<br>AGCAGCAACTTCGGCACCCAGACCTACACCTGCAACGTGGACCACAAGCCCAGCAAC<br>ACCAAGGTGGACAAGACCGTGGAGAGGAAGTGCTGCGTGGAGTGCCCCCCCTGCCC<br>AGCCCCCCCAGTGGCCGGACCCTCCGTGTTCCTGTTCCCCCCCAAGCCCAAGGACA<br>CCCTGATGATCAGCAGGACCCCCGAGGTGACCTGCGTGGTGGTGGACGTGAGCCAC<br>GAGGACCCAGAGGTGCAGTTCAACTGGTACGTGGACGGCGTGGAGGTGCACAACGC<br>CAAGACCAAGCCCAGAGAGGAACAGTTTAACAGCACCTTCAGGGTGGTGTCCGTGCT<br>GACCGTGGTGCACCAGGACTGGCTGAACGGCAAAGAGTACAAGTGCAAGGTCTCCA<br>ACAAGGGCCTGCCAGCCCCCATCGAGAAAACCATCAGCAAGACCAAGGGCCAGCCA<br>CGGGAGCCCCAGGTGTACACCCTGCCCCCCAGCCGGGAGGAAATGACCAAGAACCA<br>GGTGTCCCTGACCTGTCTGGTGAAGGGCTTCTACCCCAGCGACATCGCCGTGGAGT<br>GGGAGAGCAACGGCCAGCCCGAGAACAACTACAAGACCACCCCCCCCATGCTGGAC<br>AGCGACGGCAGCTTCTTCCTGTACAGCAAGCTGACAGTGGACAAGAGCAGGTGGCA<br>GCAGGGCAACGTGTTCAGCTGCAGCGTGATGCACGAGGCCCTGCACAACCACTACA<br>CCCAGAAGAGCCTGAGCCTGTCCCCCGGCAAG |

TABLE 1-continued sequence listing

| SEQ ID NO | Ab region | Sequence |
|---|---|---|
| SEQ ID NO 178 | DNA Heavy Chain | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCAATATTAATGCTGCTGCTGGTATTA<br>CTCTTTATGCTCAGAAGTTTCAGGGTCGGGTCACCATGACCCGTGATACCAGCATTAG<br>CACCGCGTATATGGAACTGAGCCGCCTGCGTAGCGATGATACGGCCGTGTATTATTG<br>CGCGCGTGGTGGTTGGTTTGATTATTGGGGCCAAGGCACCCTGGTGACGGTTAGCTC<br>AGCTTCCACCAAGGGCCCCAGCGTGTTCCCCCTGGCCCCCTGCAGCAGAAGCACCA<br>GCGAGAGCACAGCCGCCCTGGGCTGCCTGGTGAAGGACTACTTCCCCGAGCCCGTG<br>ACCGTGAGCTGGAACAGCGGAGCCCTGACCAGCGGCGTGCACACCTTCCCCGCCGT<br>GCTGCAGAGCAGCGGCCTGTACAGCCTGAGCAGCGTGGTGACCGTGCCCAGCAGCA<br>ACTTCGGCACCCAGACCTACACCTGCAACGTGGACCACAAGCCCAGCAACACCAAGG<br>TGGACAAGACCGTGGAGCGGAAGTGCTGCGTGGAGTGCCCCCCCTGCCCTGCCCCT<br>CCTGTGGCCGGACCCTCCGTGTTCCTGTTCCCCCCCAAGCCCAAGGACACCCTGATG<br>ATCAGCCGGACCCCCGAGGTGACCTGCGTGGTGGTGGACGTGAGCCACGAGGACCC<br>CGAGGTGCAGTTCAACTGGTACGTGGACGGCGTGGAGGTGCACAACGCCAAGACCA<br>AGCCCCGGGAGGAACAGTTCAACAGCACCTTCCGGGTGGTGTCCGTGCTGACCGTG<br>GTGCACCAGGACTGGCTGAACGGCAAAGAATACAAGTGCAAGGTGTCCAACAAGGG<br>CCTGCCTGCCCCCATCGAGAAACCATCAGCAAGACAAAGGGCCAGCCCAGGGAAC<br>CCCAGGTGTACACCCTGCCCCCCAGCCGGGAGGAAATGACCAAGAACCAGGTGTCC<br>CTGACCTGTCTGGTGAAGGGCTTCTACCCCAGCGACATCGCCGTGGAGTGGGAGAG<br>CAACGGCCAGCCCGAGAACAACTACAAGACCACCCCCCCCATGCTGGACAGCGACG<br>GCAGCTTCTTCCTGTACAGCAAGCTGACAGTGGACAAGAGCCGGTGGCAGCAGGGC<br>AACGTGTTCAGCTGCAGCGTGATGCACGAGGCCCTGCACAACCACTACACCCAGAAG<br>AGCCTGAGCCTGTCCCCCGGCAAA |
| SEQ ID NO 179 | DNA Heavy Chain | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCGGTATTAATCCTCCTGCTGGTACTA<br>CTCTTTATGCTCAGAAGTTTCAGGGTCGGGTCACCATGACCCGTGATACCAGCATTAG<br>CACCGCGTATATGGAACTGAGCCGCCTGCGTAGCGATGATACGGCCGTGTATTATTG<br>CGCGCGTGGTGGTTGGTTTGATTATTGGGGCCAAGGCACCCTGGTGACGGTTAGCTC<br>AGCTTCCACCAAGGGCCCCAGCGTGTTCCCCCTGGCCCCCTGCAGCAGAAGCACCA<br>GCGAGAGCACAGCCGCCCTGGGCTGCCTGGTGAAGGACTACTTCCCCGAGCCCGTG<br>ACCGTGAGCTGGAACAGCGGAGCCCTGACCAGCGGCGTGCACACCTTCCCCGCCGT<br>GCTGCAGAGCAGCGGCCTGTACAGCCTGAGCAGCGTGGTGACCGTGCCCAGCAGCA<br>ACTTCGGCACCCAGACCTACACCTGCAACGTGGACCACAAGCCCAGCAACACCAAGG<br>TGGACAAGACCGTGGAGCGGAAGTGCTGCGTGGAGTGCCCCCCCTGCCCTGCCCCT<br>CCTGTGGCCGGACCCTCCGTGTTCCTGTTCCCCCCCAAGCCCAAGGACACCCTGATG<br>ATCAGCCGGACCCCCGAGGTGACCTGCGTGGTGGTGGACGTGAGCCACGAGGACCC<br>CGAGGTGCAGTTCAACTGGTACGTGGACGGCGTGGAGGTGCACAACGCCAAGACCA<br>AGCCCCGGGAGGAACAGTTCAACAGCACCTTCCGGGTGGTGTCCGTGCTGACCGTG<br>GTGCACCAGGACTGGCTGAACGGCAAAGAATACAAGTGCAAGGTGTCCAACAAGGG<br>CCTGCCTGCCCCCATCGAGAAACCATCAGCAAGACAAAGGGCCAGCCCAGGGAAC<br>CCCAGGTGTACACCCTGCCCCCCAGCCGGGAGGAAATGACCAAGAACCAGGTGTCC<br>CTGACCTGTCTGGTGAAGGGCTTCTACCCCAGCGACATCGCCGTGGAGTGGGAGAG<br>CAACGGCCAGCCCGAGAACAACTACAAGACCACCCCCCCCATGCTGGACAGCGACG<br>GCAGCTTCTTCCTGTACAGCAAGCTGACAGTGGACAAGAGCCGGTGGCAGCAGGGC<br>AACGTGTTCAGCTGCAGCGTGATGCACGAGGCCCTGCACAACCACTACACCCAGAAG<br>AGCCTGAGCCTGTCCCCCGGCAAA |
| SEQ ID NO 180 | DNA Heavy Chain | CAGGTGCAATTGGTTCAGAGCGGCGCGGAAGTGAAAAAACCGGGCGCGAGCGTGAA<br>AGTGAGCTGCAAAGCCTCCGGATATACCTTTACTTCTTCTTATATTAATTGGGTCCGCC<br>AAGCCCCTGGGCAGGGTCTCGAGTGGATGGGCAATATTAATCCTGCTACTGGTCATG<br>CTGATTATGCTCAGAAGTTTCAGGGTCGGGTGACCATGACCCGTGATACCAGCATTA<br>GCACCGCGTATATGGAACTGAGCCGCCTGCGTAGCGATGATACGGCCGTGTATTATT<br>GCGCGCGTGGTGGTTGGTTTGATTATTGGGGCCAAGGCACCCTGGTGACGGTTAGCT<br>CAGCTTCCACCAAGGGCCCCAGCGTGTTCCCCCTGGCCCCCTGCAGCAGAAGCACC<br>AGCGAGAGCACAGCCGCCCTGGGCTGCCTGGTGAAGGACTACTTCCCCGAGCCCGT<br>GACCGTGAGCTGGAACAGCGGAGCCCTGACCAGCGGCGTGCACACCTTCCCCGCC<br>GTGCTGCAGAGCAGCGGCCTGTACAGCCTGAGCAGCGTGGTGACCGTGCCCAGCAGC<br>AACTTCGGCACCCAGACCTACACCTGCAACGTGGACCACAAGCCCAGCAACACCAAG<br>GTGGACAAGACCGTGGAGCGGAAGTGCTGCGTGGAGTGCCCCCCCTGCCCTGCCCC<br>TCCTGTGGCCGGACCCTCCGTGTTCCTGTTCCCCCCCAAGCCCAAGGACACCCTGAT<br>GATCAGCCGGACCCCCGAGGTGACCTGCGTGGTGGTGGACGTGAGCCACGAGGAC<br>CCCGAGGTGCAGTTCAACTGGTACGTGGACGGCGTGGAGGTGCACAACGCCAAGAC<br>CAAGCCCCGGGAGGAACAGTTCAACAGCACCTTCCGGGTGGTGTCCGTGCTGACCG<br>TGGTGCACCAGGACTGGCTGAACGGCAAAGAATACAAGTGCAAGGTGTCCAACAAGG<br>GCCTGCCTGCCCCCATCGAGAAACCATCAGCAAGACAAAGGGCCAGCCCAGGGAA<br>CCCCAGGTGTACACCCTGCCCCCCAGCCGGGAGGAAATGACCAAGAACCAGGTGTC<br>CCTGACCTGTCTGGTGAAGGGCTTCTACCCCAGCGACATCGCCGTGGAGTGGGAGA<br>GCAACGGCCAGCCCGAGAACAACTACAAGACCACCCCCCCCATGCTGGACAGCGAC<br>GGCAGCTTCTTCCTGTACAGCAAGCTGACAGTGGACAAGAGCCGGTGGCAGCAGGG<br>CAACGTGTTCAGCTGCAGCGTGATGCACGAGGCCCTGCACAACCACTACACCCAGAA<br>GAGCCTGAGCCTGTCCCCCGGCAAA |

TABLE 1-continued sequence listing

| SEQ ID NO | Ab region | Sequence |
|---|---|---|
| SEQ ID NO 181 | ActRIIB | MTAPVVVALALLWGSLCAGSGRGEAETRECIYYNANVVELERTNQSGLERCEGEQDKRLH CYASVVRNSSGTIELVKKGCWLDDFNCYDRQECVATEENPQVYFCCCEGNFCNERFTHL PEAGGPEVTYEPPPTAPTLLTVLAYSLLPIGGLSLIVLLAFVVMYRHRKPPYGHVDIHEDPG PPPPSPLVGLKPLQLLEIKARGRFGCVVVKAQLMNDFVAVKIFPLQDKQSWQSEREIFSTP GMKHENLLQFIAAEKRGSNLEVELVVLITAPHDKGSLTDYLKGNIITVVNELCHVAETMSRGL SYLHEDVPWCRGEGHKPSIAHRDFKSKNVLLKSDLTAVLADFGLAVRFEPGKPPGDTHG QVGTRRYMAPEVLEGAINFQRDAFLRIDMYAMGLVLWELVSRCKAADGPVDEYMLPFEE EIGQHPSLEELQEVVVHKKMRPTIKDHWLKHPGLAQLCVTIEACVVDHDAEARLSAGCVEE RVSLIRRSVNGTTSDCLVSLVTSVTNVDLPPKESSI |
| SEQ ID NO 182 | ActRIIB ligand binding domain (aa19-134) | SGRGEAETRECIYYNANWELERTNQSGLERCEGEQDKRLHCYASVVRNSSGTIELVKKGC VVLDDFNCYDRQECVATEENPQVYFCCCEGNFCNERFTHLPEAGGPEVTYEPPPTAPT |
| SEQ ID NO 183 | Antibody binding region | IELVKKGSWLDDFNS |
| SEQ ID NO 184 | Antibody binding region | VKKGSWLDDFNSYDR |
| SEQ ID NO 185 | Antibody binding region | GSWLDDFNSYDRQES |
| SEQ ID NO 186 | Antibody binding region | GCWLDDFNC |
| SEQ ID NO 187 | Antibody binding region | CEGEQDKRLHCYASW |
| SEQ ID NO 188 | Antibody binding region | WLDDFN |
| SEQ ID NO 189 | Antibody binding region | EQDKR |
| SEQ ID NO 190 | Antibody binding region | KGCWLDDFNCY |
| SEQ ID NO 191 | Antibody binding region | CIYYNANWELERT |
| SEQ ID NO 192 | Antibody binding region | YFCCCEGNFCN |
| SEQ ID NO 193 | Light-h/mIgG2 aLALA Chain | DIALTQPASVSGSPGQSITISCTGTSSDVGSYNYVNVVYQQHPGKAPKLMIYGVSKRPSGV SNRFSGSKSGNTASLTISGLQAEDEADYYCGTFAGGSYYGVFGGGTKLTVLGQPKSTPTL TVFPPSSEELKENKATLVCLISNFSPGVTVAWKANGTPITQGVDTSNPTKEGNKFMASS FLHLTSDQVVRSHNSFTCQVTHEGDTVEKSLSPAECL |
| SEQ ID NO 194 | Heavy-h/mIgG2 aLALA chain | QVQLVQSGAEVKKPGASVKVSCKASGYTFTSSYINVVRQAPGQGLEWM GTINPVSGSTSYAQKFQGRVTMTRDTSISTAYMELSSLRSEDTAVYYCARGGVVFDYWGQ GTLVTVSSAKTTAPSVYPLAPVCGDTTGSSVTLGCLVKGYFPEPVTLTVVNSGSLSSGVHT FPAVLQSDLYTLSSSVTVTSSTVVPSQSITCNVAHPASSTKVDKKIEPRGPTIKPCPPCKCP APNAAGGPSVFIFPPKIKDVLMISLSPIVTCVVVDVSEDDPDVQISVVFVNNVEVHTAQTQT HREDYNSTLRVVSALPIQHQDVVMSGKEFKCKVNNKDLPAPIERTISKPKGSVRAPQVYVL PPPEEEMTKKQVTLTCMVTDFMPEDIYVEVVTNNGKTELNYKNTEPVLDSDGSYFMYSKL RVEKKNVVVERNSYSCSVVHEGLHNHHTTKSFSRTPGK |

Some embodiments of the disclosed methods, treatments, regimens, uses and kits employ a myostatin antagonist, e.g., a myostatin binding molecule or an ActRIIB binding molecule. In further embodiments, the ActRIIB binding molecule is an antagonist antibody to ActRIIB.

In some embodiments of the disclosed methods, treatments, regimens, uses and kits, the anti-ActRIIB antibody is selected from the group consisting of: a) an anti-ActRIIB antibody that binds to an epitope of ActRIIB comprising SEQ ID NO: amino acids 78-83 of SEQ ID NO: 181 (WLDDFN—SEQ ID NO:188);
(b) amino acids 76-84 of SEQ ID NO: 181 (GCWLDD-FNC—SEQ ID NO:186);
(c) amino acids 75-85 of SEQ ID NO: 181 (KGCWL-DDFNCY—SEQ ID NO:190);
(d) amino acids 52-56 of SEQ ID NO: 181 (EQDKR—SEQ ID NO:189);
(e) amino acids 49-63 of SEQ ID NO: 181 (CEGEQD-KRLHCYASW—SEQ ID NO:187);
(f) amino acids 29-41 of SEQ ID NO: 181 (CIYYNAN-WELERT—SEQ ID NO:191);
(g) amino acids 100-110 of SEQ ID NO: 181 (YFC-CCEGNFCN—SEQ ID NO:192); or
(h) amino acids 78-83 of SEQ ID NO: 181 (WLDDFN) and amino acids 52-56 of SEQ ID NO: 181 (EQDKR).
b) an antagonist antibody to ActRIIB that binds to an epitope of ActRIIB comprising amino acids 78-83 of SEQ ID NO: 181 (WLDDFN—SEQ ID NO:188);
(b) amino acids 76-84 of SEQ ID NO: 181 (GCWLDD-FNC—SEQ ID NO:186);
(c) amino acids 75-85 of SEQ ID NO: 181 (KGCWL-DDFNCY—SEQ ID NO:190);
(d) amino acids 52-56 of SEQ ID NO: 181 (EQDKR—SEQ ID NO:189);
(e) amino acids 49-63 of SEQ ID NO: 181 (CEGEQD-KRLHCYASW—SEQ ID NO:187);
(f) amino acids 29-41 of SEQ ID NO: 181 (CIYYNAN-WELERT—SEQ ID NO:191);
(g) amino acids 100-110 of SEQ ID NO: 181 (YFC-CCEGNFCN—SEQ ID NO:192); or
(h) amino acids 78-83 of SEQ ID NO: 181 (WLDDFN) and amino acids 52-56 of SEQ ID NO: 181 (EQDKR), wherein the antibody has a $K_D$ of about 2 pM.

In some embodiments of the disclosed methods, treatments, regimens, uses and kits, the antagonist antibody to ActRIIB is a human antibody.

In some embodiments of the disclosed methods, treatments, regimens, uses and kits, the antibody is bimagrumab or BYM338.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

General Methodology

ActRIIB antibodies, their characterization and methods related thereto like (i) Functional Assays, (ii) REPORTER GENE ASSAYs (RGA), (iii) Cultivation of HEK293T/17 Cell Lines, (iv) Myostatin-Induced Luciferase Reporter Gene Assays, (v) SPECIFICITY ELISAs, (vi) ActRIIB/Fc-Myostatin Binding Interaction ELISA, (vii) FACS titration on hActRIIB- and hActRIIA-Expressing Cells, (viii) Binding to primary human skeletal muscle cells, (ix) affinity Determination of Selected Anti-Human ActRIIB Fabs Using Surface Plasmon Resonance (Biacore), (x) CK ASSAY, (xi) Animal Models, (xii) TREATMENT PROTOCOLs, (xiii) Statistical Analysis, (xiiii) Pannings, (xv) antibody identification and characterization, (xvi) Optimization of antibodies derived from first affinity maturation, (xvii) IgG2 Conversion of Affinity Matured Fabs (1st Maturation), (xviiii) Second Affinity Maturation, (xx) IgG2 Conversion and Characterization of IgG2 (2nd Maturation), (xxi) Characterization of anti-ActRIIB antibodies in in vivo murine studies, (xxii) Confirmation of affinity by SET, (xxiii) Cross Blocking Studies and (xxiv) Epitope mapping details and technologies have been disclosed in the WO 2010/125003.

Study Design

This is a Phase IIa/IIb, 56-week, 4-treatment arm, parallel-group, randomized, double-blind, placebo-controlled, multi-center clinical study (FIG. 8). A screening epoch of up to 5 weeks postoperatively will be used to assess eligibility. At baseline visit, 245 eligible patients will be randomized 2:1:2:2 to either placebo, bimagrumab 70 mg, bimagrumab 210 mg, or bimagrumab 700 mg. Randomized patients will be treated for 12 months and will receive investigational treatment every 4 weeks for a total of 13 doses. When all patients have completed 24 weeks of treatment, an endpoint analysis will be conducted to assess the primary and secondary endpoints together with key safety measures. After completing the treatment epoch, patients will enter a 4-week post-treatment follow up. The end of study visit (EOS) will be 8 weeks after receiving the last dose of investigational treatment.

There are 3 study epochs:

Screening epoch: Informed consent will be obtained prior to implementing any study specific procedures. The screening epoch will start immediately once the patient starts to walk (defined as the subject completing a 4 meter gait speed test) and is able to enter a rehabilitation program, which depending on the individual patient's functional recovery is expected to start approximately 7 days after surgery. The screening epoch may last for a maximum of 4 weeks thereafter (up to 35 days postoperatively); however, it should be completed as soon as possible to ensure that patients enter the trial at the beginning of their functional recovery.

Successful surgical intervention for fracture repair, evaluated by the investigator as 1) surgical fixation or arthroplasty according to manufacturer's instruction as confirmed by X-ray AND 2) completed surgical wound healing, must be confirmed prior to patient randomization.

After confirming that all inclusion criteria and none of the exclusion criteria have been met, the patient will be randomized.

Randomization must occur as soon as possible after the initiation of the screening so that treatment with study medication can start shortly after the patient's individual "functional baseline".

The randomization date will be the 'Day 1' study visit (baseline/randomization) and used as reference for visit scheduling throughout the study period.

Treatment Epoch:

First dose of investigational treatment will be administered on the day of randomization (Day 1). At every visit, all evaluations will be performed prior to the administration of investigational treatment except for post-dose PK sampling. Patients will receive 13 doses, one every 4 weeks. Final dose will be administered at the Week 48 visit and the treatment epoch will end 4 weeks later at Week 52 visit (End of Treatment).

Investigational treatment will be administered in addition to the local standard of care for hip fracture and combined with the local rehabilitation program (including resistance training) that needs to comply with the protocol-mandated minimum requirements.

Post treatment Follow-up epoch: After completing the End of Treatment visit, patients will enter a post-treatment follow-up epoch and complete the study 4 weeks later at week 56 (or 8 weeks after receiving last dose of investigational treatment).

Rationale of Study Design

There is no published Health Authority guidance to provide considerations for this study population or for the treatment of postsurgical disuse atrophy. The working hypothesis is that drug-induced increases in muscle mass combined with standard rehabilitation will lead to enhanced recovery of muscle strength and endurance with subsequent improvements of functional performance compared with patients receiving standard of care only. As a result of improved physical performance, a decrease in the incidence of falls and related injuries/fractures can be expected.

Rationale of Dose/Regimen, Route of Administration and Duration of Treatment

The choice of doses, frequency, route of administration, and duration of treatment is based on results of three Phase I studies: the First in Human (FIH) study (CBYM338X2101 Part A), casting study in healthy male volunteers (CBYM338X2101 Part B) and the multi-dose study (CBYM338X2102) in healthy volunteers.

Dose and Frequency

In the Phase I trials, 3 mg/kg and 10 mg/kg doses were effective in increasing the TMV in healthy volunteers thus they are expected to be effective in patients after hip fracture. Results in healthy volunteers (CBYM338X2101 and CBYM338X2102) indicated that thigh muscle volume, as assessed by MRI, increased comparably for single doses of 10 mg/kg and 30 mg/kg, but the effect of 30 mg/kg lasted longer. With 3 repeated monthly doses of bimagrumab, there was a comparable increase in TMV in healthy adults at 3 mg/kg and 10 mg/kg, even though it is thought that 3 mg/kg causes complete receptor occupancy for approximately half the duration of 10 mg/kg over a dosing interval. In healthy volunteers (CBYM338X2101), a limited and transient effect on the TMV was observed after infusion of a single dose of 1 mg/kg bimagrumab. The 1 mg/kg dose is therefore expected to be a non-effective or a minimally effective dose in this study.

This study will evaluate fixed i.v. doses of bimagrumab 70, 210, or 700 mg administered every 4 weeks. The fixed dose equivalent of the mg/kg doses used in previous studies was calculated based on the mean patients' weight and similar calculation was used for the current study based on the mean patients' weight rounded to 70 kg reported in literature for hip fracture patients (66±12 kg) (Mak et al 2014). Therefore, this study will evaluate fixed i.v. doses of bimagrumab 70 (initially 1 mg/kg), 210 (initially 3 mg/kg), or 700 mg (initially 10 mg/kg).

Weight-based dosing was initially chosen to ensure consistent exposure across all patient's body weight in the respective treatment arms. Nonetheless, with either fixed- or weight-based dosing, it is not expected that randomized patients will be exposed to bimagrumab at Cmax levels exceeding those experienced with the highest tested dose in previous studies, i.e. 30 mg/kg.

Dosing frequency every 4 weeks is based on observations from PK/PD studies where the efficacy reached the same plateau with both the 10 mg/kg every 4 weeks dosing and the 30 mg every 8 weeks i.v. dosing.

Route of Administration

Study medication will be administered via intravenous infusion over 30 minutes, which was tested in study BYM338X2107 and documented to be well tolerated.

Treatment Duration

A recent study in hip fracture patients treated with an anabolic agent (ibutamoren mesylate) showed that a 6-month (but not a 3-month) treatment was effective in improving physical function as measured by the Short Physical Performance Battery and its component gait speed score (Adunsky et al 2011). Since increases in LBM are expected to reach their maximum after 2-3 months of the treatment and functional benefits are expected to be observed with a delay, it seems reasonable to hypothesize that 6 months duration of therapy is sufficient for increasing the functional recovery of hip fracture patients.

However, since hip fracture recovery takes about 1 year, there could be an added benefit of longer treatment up to 12 months (secondary objective), especially if the number of falls can be reduced over a 12-month period. The primary risk factor for a secondary hip fracture is a fall, and over 90% of all fractures occur after a fall. Using Medicare and Medicaid data from hip fracture patients 65 years of age and older, Bischoff-Ferrari et al (2010) reported that 10.3% suffered a second hip fracture within 3 years—51% of second hip fractures occurred within 6 months of the first fracture and 75% occurred within a year.

Timing of First Dose

The efficacy of bimagrumab is expected to be optimal when coupled with physical activity, therefore the timing of the first dose is aligned to be close to the start of physical therapy (i.e., 7 days-4 weeks and up to 6 weeks post-surgery). A number of studies reviewed by Chudyk et al 2009 and English and Paddon-Jones D 2010 indicate that early ambulation following surgical fixation of a hip fracture may improve patient outcomes such as early physical function, rate of discharge to home, complications and hospital readmissions. Recent reviews also argue that early (and preferably more intensive) initiation of physiotherapy is critical for overcoming the early loss of muscle strength after hip fracture surgery (Bandholm and Kehlet 2012), which is an important predictor of the course of recovery.

Rationale for Choice of Comparator

The choice of placebo as a control agent is necessary to obtain information concerning the specific versus non-specific effects of the active treatment and provides the best way of evaluating the efficacy and assessing the safety and tolerability of bimagrumab.

In the absence of any approved pharmacological comparator (i.e., a 'gold standard' or 'standard of care') in disuse atrophy, placebo will be used in addition to vitamin D (minimum 800 IU per day) and physical rehabilitation.

Expected Benefits

It is expected that as seen in healthy volunteers and patients with sIBM, the hip fracture patients will have an increase in muscle mass that may translate to better function and faster return to mobility. Over study duration, the number of falls might be reduced leading to a reduction in secondary hip fractures.

Population

Inclusion Criteria

Patients eligible for inclusion in this study have to fulfill all of the following criteria:
1. Males and post-menopausal females≥65 years at randomization;
2. Patient must have had surgical treatment of the hip fracture (medial, lateral and pertrochanteric proximal femoral fracture, AO Classification 31 A-C (AO Foundation 2013);
3. Patient must be mentally competent at randomization, to have scored at least≥21 on the Folstein Mini Mental State Examination (MMSE);
4. Patient must be able to complete a 4 m gait speed test. Patients who regain mobility/i.e. weight-bearing walking ability) during the first 7 days after surgery are not eligible.
5. Patient must be able to understand and follow the requirements and procedures for the study, be committed to participate in rehabilitation training and be willing to participate for approximately 56 weeks;
6. Patients must weigh at least 35 kg and must have a body mass index (BMI) within the range of 15-35 kg/m$^2$ at screening;

Exclusion Criteria

Patients fulfilling any of the following criteria are not eligible for inclusion in this study. No additional exclusions may be applied by the investigator, in order to ensure that the study population will be representative of all eligible patients:

Orthopedic history, medical conditions associated with muscle loss, medical conditions interfering with physical assessment (SPPB and gait speed), clinically significant cardiovascular co-morbidities, liver related conditions, or other medical conditions posing concerns.

Treatment

1. Investigational Treatment

Novartis will supply the following investigational drugs:

Bimagrumab: BYM338 150 mg/1 ml liquid in vial—colorless glass vials with rubber stopper and aluminum flip-off caps.

Placebo: BYM338 placebo/1 ml liquid in vial—colorless glass vials with rubber stopper and aluminum flip-off caps.

2. Additional Study Treatment

Local Standard of Care Therapy After Hip Fracture

Local standard of care therapy to manage patients peri/post operatively (such as for thrombosis prophylaxis, pain management, calcium supplementation, secondary osteoporosis prevention) is acceptable and may be used according to the national or local guidelines.

Protocol-Mandated Additional Study Treatment

This protocol requires adherence to:

Rehabilitation (minimum requirements are defined below)

Vitamin D supplementation (minimum 800 international units (IU) daily)

Minimum Rehabilitation Requirements

Rehabilitation after hip fracture is assumed to be a prerequisite to maximize the effect of bimagrumab in this indication. Especially resistance and strength training in the course of rehabilitation may work synergistically with an anabolic compound that induces muscle hypertrophy. Ideally, a standard rehabilitation program would be performed by all patients, to avoid variability in assessing the efficacy of various bimagrumab dose regimens.

In this study, however, no detailed single rehabilitation protocol will be defined for two reasons:

The compound should work in different scenarios including different rehabilitation programs and Harmonization across multiple sites with different rehabilitation approaches does not seem feasible. There is general agreement in the medical community about the principal phases of rehabilitation including the beneficial impact of a resistance exercise program. This protocol will ensure that each patient enrolled receives the minimum required rehabilitation elements as a basis for the synergistic action of exercise training with bimagrumab (Table 1). Adherence to the program will be monitored by the use of an electronic exercise adherence diary completed by the patient in conjunction with the investigative team.

TABLE 1

Minimal required rehabilitation training, 3 sessions/week for 10 weeks

| Phase | Study Week (approx) | Location | Goals | Mandatory elements | Repetition/Sets |
|---|---|---|---|---|---|
| Mobility/Gait/ Activity of Daily Living (ADL) training; Early resistance training | 1-6 | Inpatient rehab center, or home with outpatient/ home therapy | Safe transfers & ambulation Improve hip range of motion (ROM) | Transfer, Gait/Balance and ADL training; Hip ROM (within constraints of hip precautions) Resistance Exercise Program (e.g., resistance band, free weight, resistance exercise machine, etc) for: Hip Flexion Knee Extension Hip Extension Hip Abduction | 8-15 repetitions (1 set) of each of the 4 exercises 2-3 sets required (1 session) |

TABLE 1-continued

Minimal required rehabilitation training, 3 sessions/week for 10 weeks

| Phase | Study Week (approx) | Location | Goals | Mandatory elements | Repetition/Sets |
|---|---|---|---|---|---|
| Advanced resistance training | 7-10 | Outpatient therapy or home | Return to baseline ambulation/ADL function or better. Improve lower extremity strength | Progression of hip group and knee extension resistance exercise program Continue gait/balance training | 8-15 repetitions (1 set) of resistance exercises; progressive intensity 2-3 sets required (1 session) |

Sites must be willing and able to comply with the minimal rehabilitation measures to participate in the study. Patients may perform additional exercise if this is required at a particular site.

Key Efficacy Assessments

Total LBM and aLBM by DXA

Figure 1:
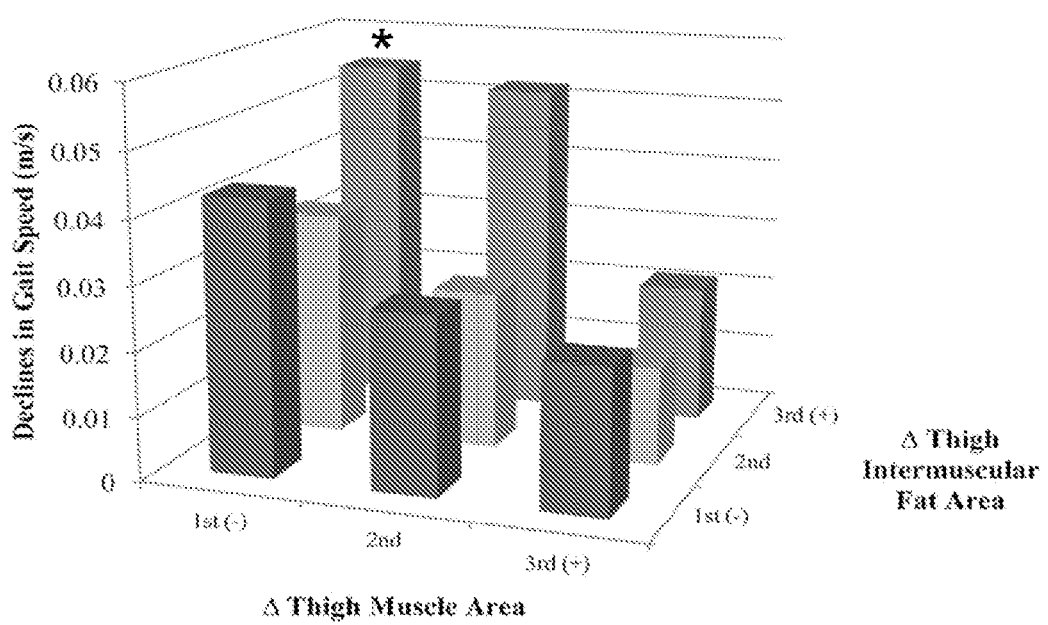
FIG. 1. Association between the change in gait speed and changes in thigh intermuscular adipose tissue area and thigh muscle area.

The clinical relevance of monitoring the changes of LBM (Lean Body Mass) lies in the fact that the drug-induced increase in muscle mass is a prerequisite of the subsequent functional improvement. Previous work on testosterone supplements have already highlighted this by documenting that in order to enhance muscle strength and physical function threshold improvements in LBM and appendicular skeletal muscle mass are necessary (Sattler et al 2011). In line with this previous observation, preliminary data on sIBM patients receiving a single dose of bimagrumab (30 mg/kg) showed that drug-induced increases in LBM (plateau at 8-12 weeks) were followed by significant increases in physical performance as quantified by the 6-minute walk distance (6 MWD) at Week 24 (FIG. 6-1). Moreover, when LBM declined upon drug withdrawal and returned to baseline, the functional benefits also vanished. Thus, increases in LBM are clinically relevant reflections of the expected functional benefits.

Dual-energy X-ray absorptiometry provides a recommended alternative method for estimating skeletal muscle mass with advantages of inexpensiveness, short scan-time, much lower radiation exposure to patients and more widespread availability in clinical and research settings as compared with the gold-standard methods, e.g. computerized tomography (CT) and MRI.

Studies document that the DXA approach gives mean total body skeletal muscle estimates that agree closely with muscle measured by CT or MRI, although DXA tends to systematically overestimate total body skeletal muscle by about 5% (Wang et al 1996, Chen et al 2007). This is due to the fact that DXA may also take into account organ lean mass of the trunk, the skin, and non-fat components in the adipose tissue when measuring total LBM (Wang et al 1976).

Focusing lean mass measurement on aLBM (legs plus arms) or leg LBM may only slightly improve the estimation of skeletal muscle mass (Chen et al 2007). However, when used in a monitoring setting, the advantages of eliminating the torso for higher accuracy may be overcome by variations arising from differences between different scans in the use of anatomical landmarks to define the extremities (Covey et al 2010, Wang et al 1996). This latter variation is of particular relevance in the context of multi-center Phase 2 clinical trials aiming to establish the dose-response relationship between the drug and the induced changes of skeletal muscle mass.

Furthermore, the relative inaccuracy of total LBM to estimate total skeletal muscle mass is of less concern in the monitoring setting, because the drug has no known effect on organ lean mass, skin, or the non-fat components of fat mass. In support, our observations in the BYM338X2102 study indicated a high degree of correlation (r=0.94) between the percent changes of total LBM (DXA) and percent changes of thigh muscle volume (MRI).

While total LBM is the preferred choice to quantify the primary pharmacodynamics effect of the drug and establish the dose-response relationship, the measurement and monitoring of the changes of aLBM—which will also be the subject of postoperative rehabilitation (physical exercise)—will be of increased interest for the exploration of how drug-induced changes in skeletal muscle mass predict/reflect the anticipated functional benefits of the treatment.

Short Physical Performance Battery (SPPB)

The Short Physical Performance Battery (SPPB) has been shown to be highly predictive of subsequent disability, hospitalization, institutionalization, and mortality in community-dwelling elders in epidemiological studies and outpatient clinics (Guralnik et al 2000; Studenski et al 2003). The disability remains even after adjustment for level and severity of comorbidity and self-report functional status.

Recently, it has been demonstrated that the SPPB can be feasibly and safely used to evaluate the functional status of acutely ill geriatric patients admitted to the hospital for serious medical conditions and that the SPPB score can provide important short-term prognostic information (Volpato et al 2008). Patients with a SPPB score below 10 are more likely to present with several other diseases than those patients with a score of 10 or higher. In multiple regression analysis, the authors found that the significant independent predictors of poor lower extremity function were age, diabetes, stroke, and osteoporosis.

Moreover, sequential assessment of physical performance by SPPB during hospital stay and in the first weeks after discharge can provide additional information on future health risk in older acutely ill patients. Collectively, SPPB might be considered as a nonspecific but highly sensitive indicator of global health status reflecting several underlying physiological impairments.

Gait Speed

Gait speed will be measured as a component of SPPB to assess functional improvement. Usual gait speed represents one of the most suitable physical performance measures to be implemented into the standard clinical evaluation of older persons. Gait speed is associated with physical activity levels, changes in the isometric force of lower extremity muscles, frailty and falls (Newman et al 2005, Chandler et al 1998, Cesari et al 2005).

Gait speed is not only a well-established measure of physical function but it may also predict future disability in diverse community-dwelling elderly populations and is sensitive to reflect changes in physical status in response to changes in physical activity, including short-term rehabilitation (Barthuly et al 2012). Poor functional performance as measured by slow or declining gait speed is related to risk of disability, hospitalization and mortality (Studenski et al 2011), whereas improvements in gait speed are related to reductions in mortality risk (Hardy et al 2007). For these reasons, gait speed has often been quoted as a global indicator of health in the geriatric population.

Falls and Fractures

Hip fracture patients experience a substantial reduction of mobility following fracture, with most patients never returning to the pre-fracture level of mobility. Many of these patients also experience mobility-related events in the period post-fracture, notably falls (Bischoff-Ferrari et al 2010). In such fragile individuals, falls often cause injuries, including recurrent fractures. Treatment with bimagrumab in the period after fracture is likely to accelerate muscle volume gain, and may improve strength and mobility, which is likely to result in improved physical function and potentially a reduction in mobility-related adverse events.

Key Safety Assessments

Safety assessments in this study will include:
Evaluation of all AEs and SAEs including infusion site and hypersensitivity reactions
Physical examination
Vital signs, height and weight
Laboratory evaluations
Electrocardiogram (ECG)
2D Echocardiographic monitoring of cardiac dimensions, wall thickness and contractility
X-ray assessment of surgical complications (if applicable) and hip fracture healing
Immunogenicity
Nutritional status
DEXA for monitoring BMD of the contralateral (non-affected) hip

LIST OF REFERENCES

Abrahamsen B, van Staa T, Ariely R, Olson M, Cooper C (2009). Excess mortality following hip fracture: a systematic epidemiological review. Osteoporos Int; 20(10): 1633-50.

Adunsky A, Chandler J, Heyden N, et al (2011) MK-0677 (ibutamoren mesylate) for the treatment of patients recovering from hip fracture: a multicenter, randomized, placebo-controlled phase IIb study. Arch Gerontol Geriatr; 53:183-9.

Auais M A, Eilayyan O, Mayo N E (2012) Extended exercise rehabilitation after hip fracture improves patients' physical function: a systematic review and meta-analysis. Phys Ther; 92:1437-1451.

Bandholm T and Kehlet H (2012) Physiotherapy exercise after fast-track total hip and knee arthroplasty: time for reconsideration? Arch Phys Med Rehabil; 93:1292-4.

Barthuly A M, Bohannon R W, Gorack W (2012) Gait speed is a responsive measure of physical performance for patients undergoing short-term rehabilitation. Gait Posture; 36(1):61-4.

Bischoff-Ferrari H A, Dawson-Hughes B, Platz A, et al (2010) Effect of high-dosage cholecalciferol and extended physiotherapy on complications after hip fracture: a randomized controlled trial. Arch Intern Med; 170:813-20.

Beavers K M, Beavers D P, Houston D K, Harris T B, Hue T F, Koster A, Newman A B, Simonsick E M, Studenski S A, Nicklas B J, Kritchevsky S B. Associations between body composition and gait-speed decline: results from the Health, Aging, and Body Composition study. Am J Clin Nutr. 2013; 97(3):552-60.

Brooks S V, Faulkner J A. Skeletal muscle weakness in old age: underlying mechanisms. Med Sci Sports Exerc. 1994; 26(4):432-9.

Campbell C, Escolar D, Mah J, et al. A Phase 2, randomized, placebo-controlled, multiple ascending-dose study of ACE-031, a soluble activin receptor Type IIB, in boys with Duchenne muscular dystrophy (DMD). Neurology 2012; 78:PO4.088.

Cesari M, Kritchevsky S B, Penninx B W, et al (2005) Prognostic value of usual gait speed in well-functioning older people—results from the Health, Aging and Body Composition Study. J Am Geriatr Soc; 53:1675-80.

Chandler J M, Duncan P W, Kochersberger G, Studenski S (1998) Is lower extremity strength gain associated with improvement in physical performance and disability in frail, community-dwelling elders? Arch Phys Med Rehabil; 79(1):24-30.

Chen Z, Wang Z, Lohman T, et al (2007) Dual-energy X-ray absorptiometry is a valid tool for assessing skeletal muscle mass in older women. J Nutr; 137(12):2775-80.

Chevalier S, Gougeon R, Choong N, Lamarche M, Morais J A. Influence of adiposity in the blunted whole-body protein anabolic response to insulin with aging. J Gerontol A Biol Sci Med Sci 2006; 61:156-64.

Chudyk A M, Jutai J W, Petrella R J, Speechley M (2009) Systematic review of hip fracture rehabilitation practices in the elderly. Arch Phys Med Rehabil; 90:246-62.

Covey M K, Berry J K, Hacker E D (2010) Regional body composition: cross-calibration of DXA scanners—QDR4500W and Discovery Wi. Obesity (Silver Spring); 18(3):632-7.

D'Adamo C R, Hawkes W G, Miller R R, Jones M, Hochberg M, Yu-Yahiro J, Hebel J R, Magaziner J. Short-term changes in body composition after surgical repair of hip fracture. Age Ageing. 2014; 43(2):275-80.

Daguet E1, Jolivet E, Bousson V, Boutron C, Dahmen N, Bergot C, Vicaut E, Laredo J D. Fat content of hip muscles: an anteroposterior gradient. J Bone Joint Surg Am. 2011; 93(20):1897-905.

English K L, Paddon-Jones D (2010) Protecting muscle mass and function in older adults during bed rest. Curr Opin Clin Nutr Metab Care; 13(1): 34-39.

Frontera W R, Hughes V A, Fielding R A, Fiatarone M A, Evans W J, Roubenoff R. Aging of skeletal muscle: a 12-yr longitudinal study. J Appl Physiol. 2000; 88(4): 1321-6.

Fox K M1, Magaziner J, Hawkes W G, Yu-Yahiro J, Hebel J R, Zimmerman S I, Holder L, Michael R. Loss of bone density and lean body mass after hip fracture. Osteoporos Int. 2000; 11(1):31-5.

Goodpaster B H, Park S W, Harris T B, et al. The loss of skeletal muscle strength, mass, and quality in older adults: the health, aging and body composition study. J Gerontol A Biol Sci Med Sci. 2006; 61(10):1059-64.

Goodpaster B H, Carlson C L, Visser M, et al. Attenuation of skeletal muscle and strength in the elderly: The Health ABC Study. J Appl Physiol. 2001; 90(6):2157-65.

Guralnik J M, Ferrucci L, Pieper C F, et al (2000) Lower extremity function and subsequent disability: consistency across studies, predictive models, and value of gait speed alone compared with the short physical performance battery. J Gerontol A Biol Sci Med Sci; 55(4):M221-31.

Hardy S E, Perera S, Roumani Y F, et al (2007) Improvement in usual gait speed predicts better survival in older adults. J Am Geriatr Soc; 55(11):1727-34.

Lach-Trifilieff E1, Minetti G C, Sheppard K, Ibebunjo C, Feige J N, Hartmann S, Brachat S, Rivet H, Koelbing C, Morvan F, Hatakeyama S, Glass D J. An antibody blocking activin type II receptors induces strong skeletal muscle hypertrophy and protects from atrophy. Mol Cell Biol. 2014; 34(4):606-18.

Lang T, Cauley J A, Tylaysky F, Bauer D, Cummings S, Harris T B; Health ABC Study. Computed tomographic measurements of thigh muscle cross-sectional area and attenuation coefficient predict hip fracture: the health, aging, and body composition study. J Bone Miner Res. 2010; 25(3):513-9.

Lee S J, McPherron A C. Regulation of myostatin activity and muscle growth. Proc Natl Acad Sci USA. 2001 Jul. 31; 98(16):9306-11.

Lee S J, Reed L A, Davies M V, Girgenrath S, Goad M E, Tomkinson K N, Wright J F, Barker C, Ehrmantraut G, Holmstrom J, Trowell B, Gertz B, Jiang M S, Sebald S M, Matzuk M, Li E, Liang L F, Quattlebaum E, Stotish R L, Wolfman N M. Regulation of muscle growth by multiple ligands signaling through activin type II receptors. Proc Natl Acad Sci USA. 2005 Dec. 13; 102(50):18117-22.

Newman A B, Haggerty C L, Kritchevsky S B, Nevitt M C, Simonsick E M; Health ABC Collaborative Research Group (2003) Walking performance and cardiovascular response: associations with age and morbidity—the Health, Aging and Body Composition Study. J Gerontol A Biol Sci Med Sci; 58(8):715-20.

Pahor M, Kritchevsky S. Research hypotheses on muscle wasting, aging, loss of function and disability. J Nutr Health Aging 1998; 2: 97-100.

Sattler F, Bhasin S, He J, et al (2011) Testosterone threshold levels and lean tissue mass targets needed to enhance skeletal muscle strength and function: the HORMA trial. J Gerontol A Biol Sci Med Sci; 66:122-9.

Schaap L A, Pluijm S M, Smit J H, van Schoor N M, Visser M, Gooren L J, Lips P. The association of sex hormone levels with poor mobility, low muscle strength and incidence of falls among older men and women. Clin Endocrinol (Oxf) 2005; 63:152-60.

Smith R C, Lin B K. Myostatin inhibitors as therapies for muscle wasting associated with cancer and other disorders. Curr Opin Support Palliat Care. 2013; 7(4): 352-360.

Studenski S, Perera S, Wallace D, et al (2003) Physical performance measures in the clinical setting. J Am Geriatr Soc; 51(3):314-22.

Studenski S, Perera S, Patel K, et al (2011) Gait speed and survival in older adults. JAMA; 305(1):50-8.

Trendelenburg A U, Meyer A, Rohner D, Boyle J, Hatakeyama S, Glass D J. Myostatin reduces Akt/TORC1/p70S6K signaling, inhibiting myoblast differentiation and myotube size. Am. J. Physiol. Cell Physiol. 2009; 296: C1258-C1270.

Vandervoort A A. Aging of the human neuromuscular system. Muscle Nerve. 2002; 25(1):17-25.

Verghese J, Holtzer R, Oh-Park M, Derby C A, Lipton R B, Wang C. Inflammatory markers and gait speed decline in older adults. J Gerontol A Biol Sci Med Sci 2011; 66:1083-9. 31.

Visser M, Kritchevsky S B, Goodpaster B H, et al. Leg muscle mass and composition in relation to lower extremity performance in men and women aged 70 to 79: the health, aging and body composition study. J Am Geriatr Soc. 2002; 50(5):897-904.

Visser M, Goodpaster B H, Kritchevsky S B, et al. Muscle mass, muscle strength, and muscle fat infiltration as predictors of incident mobility limitations in well-functioning older persons. J Gerontol A Biol Sci Med Sci. 2005; 60(3):324-33.

Visser M, Pahor M, Taaffe D R, Goodpaster B H, Simonsick E M, Newman A B, Nevitt M, Harris T B. Relationship of interleukin-6 and tumor necrosis factor-alpha with muscle mass and muscle strength in elderly men and women: the Health ABC Study. J Gerontol A Biol Sci Med Sci 2002; 57:M326-32.

Volpato S, Cavalieri M, Guerra G, et al (2008) Performance-based functional assessment in older hospitalized patients: feasibility and clinical correlates. J Gerontol A Biol Sci Med Sci; 63(12):1393-8.

Wang J, Pierson R N Jr (1976) Disparate hydration of adipose and lean tissue require a new model for body water distribution in man. J Nutr; 106:1687-93.

Wang Z M, Visser M, Ma R, et al (1996) Skeletal muscle mass: evaluation of neutron activation and dual-energy X-ray absorptiometry methods. J Appl Physiol; 80:824-31.

Waters D L, Qualls C R, Dorin R I, Veldhuis J D, Baumgartner R N. Altered growth hormone, cortisol, and leptin secretion in healthy elderly persons with sarcopenia and mixed body composition phenotypes. J Gerontol A Biol Sci Med Sci 2008; 63:536-41.

Wehren L E1, Hawkes W G, Hebel J R, Orwig D L, Magaziner J. Bone mineral density, soft tissue body composition, strength, and functioning after hip fracture. J Gerontol A Biol Sci Med Sci. 2005; 60(1):80-4.

Whittemore L A, Song K, Li X, Aghajanian J, Davies M, Girgenrath S, Hill J J, Jalenak M, Kelley P, Knight A, Maylor R, O'Hara D, Pearson A, Quazi A, Ryerson S, Tan X Y, Tomkinson K N, Veldman G M, Widom A, Wright J F, Wudyka S, Zhao L, Wolfman N M. Inhibition of myostatin in adult mice increases skeletal muscle mass and strength. Biochem Biophys Res Commun. 2003 Jan. 24; 300(4):965-71

The invention claimed is:

1. A method of improving muscle mass and function in a patient with disuse atrophy triggered by reduced mobility due to a hip fracture and consequent major surgery for hip fracture repair comprising administering an effective amount of bimagrumab to the patient.

2. The method according to claim 1, comprising administering bimagrumab after confirmation of successful surgical hip fracture repair and wound healing in the patient.

3. The method according to claim 2, comprising starting the administration of bimagrumab at about 7-42 days or about 1 to 6 weeks after confirmation of successful surgical hip fracture repair and wound healing in the patient.

4. The method according to claim 2, comprising starting the administration of bimagrumab when the patient is able to sustain weight-bearing walk with or without a walking aid and is able to initiate physical rehabilitation.

5. The method according to claim 3, wherein bimagrumab is administered to the patient at a dose of about 70-700 mg.

6. The method according to claim 5, wherein bimagrumab is administered to the patient at a dose of about 70 mg or about 210 mg or about 700 mg.

7. The method according to claim 6, comprising administering bimagrumab to the patient intravenously.

8. The method according to claim 7, comprising administering bimagrumab to the patient every four weeks.

9. The method according to claim 8, comprising administering bimagrumab to the patient for at least 3 months.

10. The method according to claim 8, comprising administering bimagrumab to the patient for about 6 months.

11. The method according to claim 8, comprising administering bimagrumab to the patient for up to 12 months.

* * * * *